US010577399B2

(12) United States Patent
Smith et al.

(10) Patent No.: US 10,577,399 B2
(45) Date of Patent: Mar. 3, 2020

(54) MODIFIED LANTIBIOTICS AND METHODS OF MAKING AND USING THE MODIFIED LANTIBIOTICS

(71) Applicant: THE TEXAS A&M UNIVERSITY SYSTEM, College Station, TX (US)

(72) Inventors: James L. Smith, College Station, TX (US); Jerome Escano, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 15/797,001

(22) Filed: Oct. 30, 2017

(65) Prior Publication Data

US 2018/0118791 A1    May 3, 2018

Related U.S. Application Data

(60) Provisional application No. 62/414,334, filed on Oct. 28, 2016.

(51) Int. Cl.
  *C07K 14/315*    (2006.01)
  *C12N 15/74*     (2006.01)
  *A61K 38/00*     (2006.01)

(52) U.S. Cl.
  CPC .......... *C07K 14/315* (2013.01); *C12N 15/746* (2013.01); *A61K 38/00* (2013.01)

(58) Field of Classification Search
  None
  See application file for complete search history.

(56) References Cited

U.S. PATENT DOCUMENTS

| 9,260,488 B2 | 2/2016 | Hillman et al. |
| 9,963,488 B2 | 5/2018 | Hillman et al. |

FOREIGN PATENT DOCUMENTS

WO    WO-2018013967 A1 * 1/2018    ............... A61K 8/64

OTHER PUBLICATIONS

Kupke et al. ("Purification and Characterization of EpiD, a Flavoprotein Involved in the Biosynthesis of the Lantibiotic Epiderm," Journal of Bacteriology, Aug. 1992, vol. 174, No. 16, p. 5354-5361) (Year: 1992).*

Bierbaum, G. et al. "Lantibiotics: Mode of Action, Biosynthesis and Bioengineering" *Current Pharmaceutical Biotechnology*, 2009, pp. 2-18, vol. 10, No. 1.
Chen, S. et al. "Site-Directed Mutations in the Lanthipeptide Mutacin 1140" *Applied and Environmental Microbiology*, Jul. 2013, pp. 4015-4023, vol. 79, No. 13.
Craik, D. J. et al. "The Future of Peptide-based Drugs" *Chemical Biology Drug Design*, 2013, pp. 136-147, vol. 81.
Escano, J. et al, "Multipronged approach for engineering novel peptide analogues of existing lantibiotics" *Expert Opinion and Drug Discovery*, May 25, 2015, pp. 857-870, vol. 10, No. 8.
Levengood, M. R. et al. "In Vitro Mutasynthesis of Lantibiotic Analogues Containing Nonproteinogenic Amino Acids" *Journal of American Chemical Society*, Aug. 5, 2009, pp. 12024-12025, vol. 131, No. 34.
Maher, S. et al. "Chemical Modification of the Carboxyl Terminal of Nisin A with Biotin does not Abolish Antimicrobial Activity Against the Indicator Organism, *Kocuria rhizophila*" *International Journal of Peptide Research Therapeutics*, 2009, pp. 219-226, vol. 15.
Molloy, E. M. et al. "Saturation Mutagenesis of Lysine 12 Leads to the Identification of Derivatives of Nisin a with Enhanced Antimicrobial Activity" *PLOS One*, Mar. 11, 2013, pp. 1-10, vol. 8, No. 3.
Tabor, A. B. "Recent advances in synthetic analogues of lantibiotics: What can we learn from these?" *Bioorganic Chemistry*, 2014, pp. 39-50, vol. 55.
Escano, J. et al. "Importance of Decarboxylation in the Biosynthesis of the Lantibiotic, Mutacin 1140" *4th Annual Fall Meeting of the Texas Branch American Society for Microbiology*, Oct. 29-31, 2015, p. 1, Abstract Only.

* cited by examiner

*Primary Examiner* — Christina Bradley
(74) *Attorney, Agent, or Firm* — Saliwanchik, Lloyd & Eisenschenk

(57) ABSTRACT

The subject invention pertains to a modified lantibiotic containing an intact cysteine at the C-terminus, particularly, a cysteine that is not decarboxylated and that contains a free carboxyl group. Derivatives of the modified lantibiotic comprising a moiety conjugated to the carboxyl group of the terminal cysteine are also provided. A bacterium that produces a modified lantibiotic having an intact cysteine at the C-terminus are also provided, wherein the bacterium is genetically modified to inactivate a gene that encodes a decarboxylase enzyme that decarboxylates the cysteine at the C-terminus of a precursor lantibiotic. Methods of producing a modified lantibiotic having an intact cysteine at the C-terminus by culturing a bacterium that synthesizes the modified lantibiotic and purifying the lantibiotic are also provided. Mutants of lantibiotics, particularly, mutacin 1140 having higher anti-bacterial activity or higher bacterial expression compared to mutacin 1140 are also provided.

20 Claims, 16 Drawing Sheets
(8 of 16 Drawing Sheet(s) Filed in Color)
Specification includes a Sequence Listing.

Lichenicidin A2

Lactocin S

Mutacin II

Epidermin

Gallidermin

Salivaricin

Lacticin 3147 - A2

Actagardine

Mersacidin

MODIFIED LANTIBIOTICS AND METHODS OF MAKING AND USING THE MODIFIED LANTIBIOTICS

CROSS-REFERENCE TO RELATED APPLICATION

This application claims the benefit of U.S. Provisional Application Ser. No. 62/414,334, filed Oct. 28, 2016, the disclosure of which is hereby incorporated by reference in its entirety, including all figures, tables and amino acid or nucleic acid sequences.

The Sequence Listing for this application is labeled "Seq-List-replace.txt" which was created on Oct. 2, 2019 and is 25 KB. The entire content of the sequence listing is incorporated herein by reference in its entirety.

BACKGROUND OF THE INVENTION

Lantibiotics are characterized by their post-translational modifications (PTMs). Dehydrations of serine and threonine residues into dehydroalanine and dehydrobutyrine residues, respectively, are common modifications found in lantibiotics. These dehydrated residues are cyclized with cysteines to form thioether bridges, which are called lanthionines[1-2]. Lantibiotics can contain other post-translational modifications, such as D-alanines in lacticin 3147, β-hydroxy aspartate in cinnamycin, 2-oxopropionyl in lactocin S, and an oxidized lanthionine in actagardine[3-6].

The epidermin group of lantibiotics and other lantibiotic peptides have a S—[(Z)-2-aminovinyl]-D-cysteine (AviCys) residue at the C-terminal end of the peptide (FIG. 1a). This residue consists of a decarboxylated cysteine which forms a lanthionine ring. Several of these modifications are important for lantibiotic activity; however, the importance of the AviCys for the lantibiotic activity in the epidermin group of lantibiotics is not known.

Mutacin 1140, produced by *Streptococcus mutans* JH1140, is a lantibiotic that has shown promise as a potential therapeutic (FIG. 1b)[7-9]. It has a broad spectrum of activity against Gram-positive bacteria[10]. Further, mutacin 1140 has been shown to clear *Staphylococcus aureus* infections in rodent models with little toxicity[11]. The bacterium producing mutacin 1140 has been engineered into a therapy for preventing dental caries[12].

Mutacin 1140 belongs to the class I epidermin group of lantibiotics and is structurally related to epidermin and gallidermin[13-14]. The first two lanthionine rings, rings A and B, of the epidermin group are referred to as the lipid II binding domain. The lantibiotic nisin shares structural homology to the lanthionine rings A&B. The latter half of the epidermin and nisin peptide is referred to as the lateral assembly domain, which presumably abducts lipid II into large lipid II/lantibiotic complexes[15-16].

Decarboxylation of a C-terminal cysteine to form an AviCys residue occurs in several metabolites[17]. AviCys is present in the class II lantibiotics mersacidin and microbisporicin[17-18]. It is also found in non-lantibiotics, such as cypemycin. Cypemycin contains many of the lantibiotic PTM modifications; however, it does not form lanthionine rings[19]. The AviCys residue has also been found in the nonribosomal peptide synthetases (NRPS) produced metabolite thiovideramide. The mechanism of AviCys formation for the NRPS peptide maybe different due the nature of its biosynthesis[20].

In certain lantibiotics, decarboxylation of cysteine at the C-terminus is performed by the flavoprotein LanD. This decarboxylase has been shown to be specific for C-terminal cysteines. Furthermore, LanD could not decarboxylate an ethyl-thioether mimic, suggesting decarboxylation occurs before ring D formation[21]. Crystal structures for both EpiD, the decarboxylase for epidermin, and MrsD, the decarboxylase for mersacidin, indicate that these enzymes form a homo-dodecamer[22-23]. Studies on the mechanism of activity suggest that decarboxylation produces an ene-thiol intermediate that promotes terminal ring formation[24]. There have been no reports of an isolated carboxylated analog of an AviCys containing lantibiotic, even in an EpiD deletion mutant of epidermin biosynthesis[25].

HOAt/EDC coupling has been achieved for lantibiotics that contain a C-terminal carboxyl group. NVB302, an analog of actagardine which has undergone phase 1 clinical trials, has a diaminoheptane tail attached to the C-terminus of the lantibiotic[27]. Additionally, lantibiotics can be produced through solid-phase peptide synthesis using orthogonally protected lanthionine rings[26, 28].

BRIEF SUMMARY OF THE INVENTION

Chemical modification of lantibiotics offers a novel avenue for the development of new therapeutics[26]. The lack of a C-terminal carboxyl group complicates the further development of the lantibiotics containing a C-terminal cysteine, for example, epidermin group of lantibiotics, using C-terminal modifications. A free carboxyl group analog of the lantibiotics containing a C-terminal cysteine would promote studies aimed at understanding the functional basis for AviCys residues within the lantibiotic and promote the synthesis of lantibiotics having improved therapeutic efficacy.

Accordingly, an embodiment of the invention provides a modified lantibiotic containing an intact cysteine at the C-terminus, particularly, a cysteine that is not decarboxylated and that contains a free carboxyl group. Derivatives of the modified lantibiotic comprising a moiety conjugated to the carboxyl group of the terminal cysteine are also provided. In certain embodiments, the moiety conjugated to the carboxyl group of the modified lantibiotic having an intact C-terminal cysteine is a functional group or a detectable label.

A bacterium that produces a modified lantibiotic having an intact cysteine at the C-terminus is also provided, wherein the bacterium is genetically modified to inactivate a gene that encodes a decarboxylase enzyme that decarboxylates the cysteine at the C-terminus of a precursor lantibiotic.

Methods of producing a modified lantibiotic having an intact cysteine at the C-terminus by culturing a bacterium that synthesizes the modified lantibiotic and purifying the lantibiotic are also provided.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

BRIEF DESCRIPTION OF THE SEQUENCES

Figure 1A:
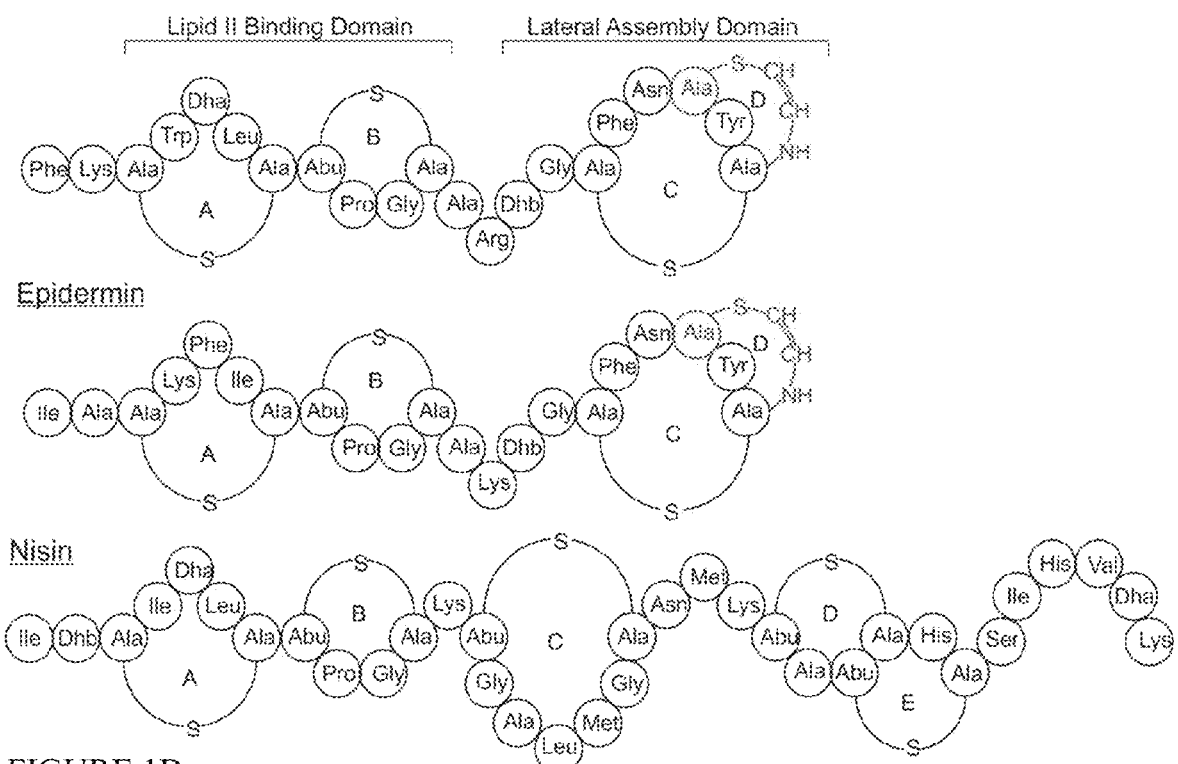
FIGS. 1A-1B. Structures of class I and class II lantibiotics. (A) Structures of class I lantibiotics: mutacin 1140 (SEQ ID NO: 33), epidermin (SEQ ID NO: 34), and nisin (SEQ ID NO: 35). Dehydrated residues are either Dha or Dhb. The lipid II binding domain of class I lantibiotics consist of the first two lanthionine rings A and B, while the lateral assembly domain consist of the terminal rings. (B) Structure of the class II lantibiotic, mersacidin (SEQ ID NO: 36), which contains an AviCys. Residues involved in AviCys formation are labeled in red for both classes.
Figure 1B:
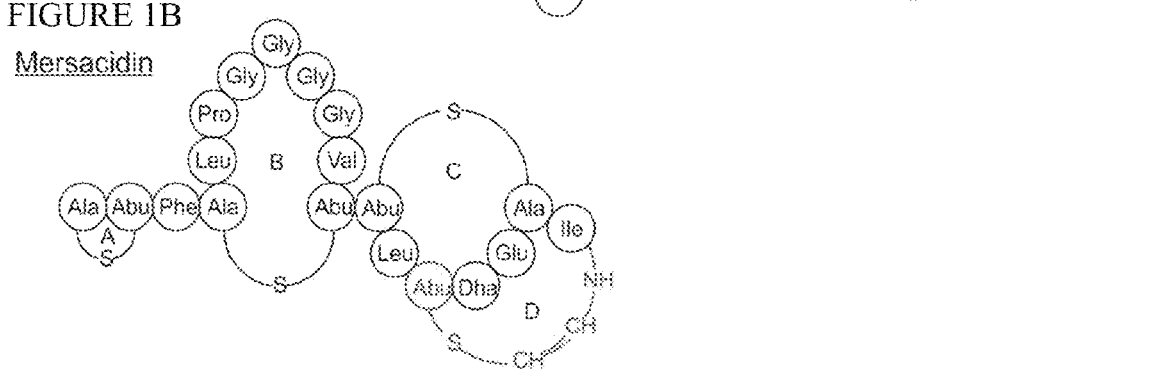

SEQ ID NO: 1-13: Sequences of exemplary lantibiotic propeptides.
SEQ ID NO: 14-26: Sequences of exemplary mature lantibiotics.
SEQ ID NO: 27: Forward primer for mutD replacement.
SEQ ID NO: 28: Reverse primer for mutD replacement.
SEQ ID NO: 29: Forward primer for mutD replacement.
SEQ ID NO: 30: Reverse primer for mutD replacement.
SEQ ID NO: 31: Forward primer for mutD clean deletion.
SEQ ID NO: 32: Reverse primer for mutD clean deletion.

DETAILED DISCLOSURE OF THE INVENTION

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the modified lantibiotics described herein, its use in the pharmaceutical compositions of the invention is contemplated.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disorder such that an improvement is observed in the patient, notwithstanding that the patient may still be afflicted with the underlying disorder, for example, a bacterial infection.

The term "effective amount" or "therapeutically effective amount" refers to that amount of an inhibitor described herein that is sufficient to effect the intended application including but not limited to disease treatment, for example, clearing a bacterial infection. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on the particular lantibiotic chosen, the dosing regimen to be followed, whether it is administered in combination with other compounds, timing of administration, the tissue to which it is administered, and the physical delivery system in which it is carried.

"Subject" refers to an animal, such as a mammal, for example a human. The methods described herein can be useful in both humans and non-human animals. In some embodiments, the subject is a mammal.

As used herein, "a lantibiotic" is a protein produced by a bacterium that is active against another bacterium and that contains one or more thioether bridges called lanthionines. A lantibiotics contains one or more amino acids having PTMs, for example, dehydrations of serine and threonine residues into dehydroalanine and dehydrobutyrine residues, respectively. In addition, these dehydrated residues are cyclized with cysteines to form thioether bridges called lanthionines.

The epidermin group of lantibiotics and certain other lantibiotics have S—[(Z)-2-aminovinyl]-D-cysteine (AviCys) residue at the C-terminal end of the lantibiotic (FIG. 1a). This residue is produced by decarboxylation of the cysteine at the C-terminus of precursor lantibiotic peptide. AviCys forms a lanthionine ring with other post-translationally modified amino acids of the lantibiotic peptide.

As used herein, "a lantibiotic peptide" refers to a peptide that does not contain any PTMs. Post-translational modification of the lantibiotic peptide produces a lantibiotic.

As used herein, a "precursor lantibiotic" refers to a peptide that contains an intact cysteine at the C-terminus of the lantibiotic, i.e., a cysteine at the C-terminus of the precursor lantibiotic that is not decarboxylated and that contains a free carboxyl group. A "precursor lantibiotic" may or may not contain the other PTMs present in the corresponding lantibiotic.

The term "modified lantibiotic" refers to a lantibiotic that contains all the other PTMs present in a lantibiotic, except the PTMs to the cysteine at the C-terminus of the lantibiotic. Accordingly, in a modified lantibiotic, the cysteine at the C-terminus is not decarboxylated and contains a free carboxyl group and the modified lantibiotic contains all the other PTMs present in the corresponding lantibiotic.

The term "parent lantibiotic" is used herein to distinguish a "modified lantibiotic" or a "functionalized lantibiotic" from the corresponding "lantibiotic". For example, a "modified mutacin" contains all the other PTMs present in mutacin, except the PTMs to the cysteine at the C-terminus of mutacin. Similarly, a "functionalized mutacin" contains all the other PTMs present in mutacin, except the PTMs to the cysteine at the C-terminus of mutacin and wherein the carboxyl group of the cysteine at the C-terminus is conjugated to a moiety.

A "native gene" or "an endogenous gene" is a gene that is naturally found in a bacterium; whereas, an "exogenous gene" is a gene introduced into a bacterium and which was obtained from an organism other the bacterium.

The invention relates to the importance of the C-terminal S—[(Z)-2-aminovinyl]-D-cysteine (AviCys) residue for antibacterial activity of lantibiotics. The PTM for making the AviCys residue is essential for the lateral assembly mechanism of activity that traps lipid II into a large complex.

Accordingly, one embodiment of the invention provides a modified lantibiotic having an intact cysteine at the C-terminus. Non-limiting examples of parent lantibiotics that correspond to the modified lantibiotics described herein include lichenicidin (e.g., SEQ ID NO: 1), lactocin-S (e.g., SEQ ID NO: 2), salivaricin (e.g., SEQ ID NO: 3), mutacin (e.g., SEQ ID NOs: 4, 10 and 11), lacticin (e.g., SEQ ID NO: 5), actagardine (e.g., SEQ ID NO: 6), mersacidin (e.g., SEQ ID NO: 7), epidermin (e.g., SEQ ID NO: 8), gallidermin (e.g., SEQ ID NO: 9), ruminococcin (e.g., SEQ ID NO: 12) or microbisporicin (SEQ ID NO: 13).

The modified lantibiotics having an intact cysteine at the C-terminus can be further conjugated to moieties through the free carboxyl group of the cysteine at the C-terminus. Accordingly, functionalized lantibiotic is provided, wherein the carboxyl group of the cysteine at the C-terminus is conjugated to a moiety.

The moiety can be a functional group or a detectable label. Non-limiting examples of the functional groups that can be conjugated to the carboxyl group of the cysteine at the C-terminus of the modified lantibiotic include substituted or unsubstituted chemical groups, such as alkane, alkene, alkyne, haloalkyl, alcohol, ether, amine, aldehyde, ketone, acyl halide, carboxylate, ester, amide, aryl or heteroaryl. Specific embodiments within the genus of chemical groups recited herein are well known in the art and such embodiments are within the purview of the invention.

The carboxyl group of the cysteine at the C-terminus of the modified lantibiotic can be covalently joined to a carbon or a heteroatom of the functional group.

In one embodiment, the carboxyl group of the cysteine at the C-terminus of the modified lantibiotic is covalently joined to a carbon or the nitrogen atom of an amine. The amine can be a primary or secondary amine. Non-limiting examples of amines include substituted or unsubstituted forms of alkyl-amines, for example, methylamine or diaminoheptane, or substituted or unsubstituted forms of aryl-amines or heteroaryl amines, for example, chlorophenylalanine or di-chlorophenylalanine.

In specific embodiments, the functional group is substituted halo-aryl, for example, chlorophenylalanine or di-chlorophenylalanine.

In another embodiment of the functionalized lantibiotic, the moiety is a detectable label. The detectable label can be a fluorescent label, radiolabel or bioluminescent label.

Numerous commercially available fluorescent labels are suitable for conjugation to the modified lantibiotic described herein, for example, fluorescein, dR110, 5-FAM™ 6-FAM™, dR6G, JOE™, HEX™, VIC®, TET™, dTAMRA™, TAMRA™, NED™, dROX™, ROX™, PET® and LIZ®. Additional examples of fluorescent labels suitable for the invention described herein are known to a skilled artisan and such embodiments are within the purview of the invention.

Non-limiting examples of parent lantibiotics that correspond to the functionalized lantibiotics described herein include lichenicidin (e.g., SEQ ID NO: 1), lactocin-S (e.g., SEQ ID NO: 2), salivaricin (e.g., SEQ ID NO: 3), mutacin (e.g., SEQ ID NOs: 4, 10 (mutacin ny266) and 11 (mutacin 1140/mutacin III)), lacticin (e.g., SEQ ID NO: 5), actagardine (e.g., SEQ ID NO: 6), mersacidin (e.g., SEQ ID NO: 7), epidermin (e.g., SEQ ID NO: 8), gallidermin (e.g., SEQ ID NO: 9), ruminococcin (e.g., SEQ ID NO: 12) or microbisporicin (SEQ ID NO: 13).

In certain embodiments, a parent lantibiotic that corresponds to the functionalized lantibiotics described herein comprises a sequence that is homologous to the sequence of a known lantibiotic, for example, lichenicidin (e.g., SEQ ID NO: 1), lactocin-S (e.g., SEQ ID NO: 2), salivaricin (e.g., SEQ ID NO: 3), mutacin (e.g., SEQ ID NOs: 4, 10 and 11), lacticin (e.g., SEQ ID NO: 5), actagardine (e.g., SEQ ID NO: 6), mersacidin (e.g., SEQ ID NO: 7), epidermin (e.g., SEQ ID NO: 8), gallidermin (e.g., SEQ ID NO: 9), ruminococcin (e.g., SEQ ID NO: 12) or microbisporicin (SEQ ID NO: 13). A lantibiotic that is homologous to known lantibiotic shares at least about 90%, 91%, 92%, 93%, 94%, 95%, 96%, 97%, 98% or 99% sequence identity with the sequences of the corresponding known lantibiotic, for example, lichenicidin (e.g., SEQ ID NO: 1), lactocin-S (e.g., SEQ ID NO: 2), salivaricin (e.g., SEQ ID NO: 3), mutacin (e.g., SEQ ID NOs: 4, 10 and 11), lacticin (e.g., SEQ ID NO: 5), actagardine (e.g., SEQ ID NO: 6), mersacidin (e.g., SEQ ID NO: 7), epidermin (e.g., SEQ ID NO: 8), gallidermin (e.g., SEQ ID NO: 9), ruminococcin (e.g., SEQ ID NO: 12) or microbisporicin (SEQ ID NO: 13).

For the purpose of this invention, when a sequence of lantibiotic is represented by a sequence identifier, the sequence in the sequence identifier provides the amino acids sequence of the lantibiotic prior to any PTMs. The amino acids provided in a sequence that corresponds to a lantibiotic are post-translationally modified to produce a lantibiotic having antibacterial activity. Such PTMs include, for example, dehydrations of serine and threonine residues into dehydroalanine and dehydrobutyrine residues, respectively; cyclization of the dehydrated residues with cysteines to form thioether bridges called lanthionines; formation of D-alanines (e.g., in lacticin 3147); formation of β-hydroxy aspartate (e.g., in cinnamycin); formation of 2-oxopropionyl (e.g., in lactocin S); and oxidation of lanthionine (e.g., in actagardine); formation of AviCys at the C-terminal end of the peptide (e.g., in mutacin).

A person of ordinary skill in the art can design homologs of a given lantibiotic by substituting the amino acids within a lantibiotic sequence that are not likely to affect the activity of the lantibiotic having an amino acid substitution. For example, a person of ordinary skill in the art can substitute amino acids that are not modified via PTMs in a lantibiotic, particularly, with other amino acids that have similar chemical properties via conservative amino acid substitutions.

Conservative amino acid substitutions are changes in a protein sequence that change an amino acid to a different amino acid with similar biochemical properties, e.g. charge, hydrophobicity and size. Certain examples of conservative substitutions are provided in Table 1 below:

TABLE 1

Conservative amino acid substitutions to produce homologs of a lantibiotic

| Original residue | Substitution |
| --- | --- |
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (Y) |
| Tyr (Y) | Trp (W), Phe (F), Thr (T), Ser (S) |
| Val (V) | Ile (I), Leu (L), Met (M), Phe (F), Ala (A). |

In certain embodiments, the invention provides mutant lantibiotics having one or more mutations in the core peptide. Such mutants are called core peptide mutants. Certain of the core peptide mutants of the invention exhibit higher activity, improved pharmacokinetics, higher stability, or a combination thereof, compared to the corresponding unmodified lantibiotic.

In specific embodiments, the invention provides core peptide mutants of mutacin, particularly, mutacin 1140 comprising the sequence of SEQ ID NO: 24 or mutacin B-Ny266 comprising the sequence of SEQ ID NO: 23. In other embodiments, a core peptide mutant of mutacin 1140 or mutacin B-Ny266 comprises or consists of a mutation provided in the Table 2 below.

TABLE 2

Examples of core peptide mutants of mutacin 1140 comprising SEQ ID NO: 24 or mutacin B-Ny266 comprising the sequence of SEQ ID NO: 23 containing a single amino acid mutation/substitution. For mutacin 1140, the amino acid positions are indicated with respect to SEQ ID NO: 24 and for mutacin B-Ny266, the amino acid positions are indicated with respect to SEQ ID NO: 23. Mutations in the corresponding positions of mutacin 1140 or mutacin B-Ny266 prior to post-translational modification comprising SEQ ID NO: 10 or 11, respectively, are also envisioned.

| Amino acid position | Original amino acid | Replacement amino acid |
| --- | --- | --- |
| 5 | Serine | Glycine |
| 5 | Serine | Threonine |
| 5 | Serine | Glutamate |
| 5 | Serine | Alanine |
| 13 | Arginine | Alanine |
| 14 | Threonine | Glycine |
| 14 | Threonine | Alanine |
| 15 | Glycine | Alanine |
| 12 | Alanine | Threonine |
| 4 | Tryptophan | Serine |
| 6 | Leucine | Serine |

In other embodiments, a core peptide mutant of mutacin 1140 comprises or consists of a combination of mutations described in the Table 3 below.

TABLE 3

Examples of core peptide mutants of mutacin 1140 comprising SEQ ID NO: 24 or mutacin B-Ny266 comprising the sequence of SEQ ID NO: 23. For mutacin 1140, the amino acid positions are indicated with respect to SEQ ID NO: 24 and for mutacin B-Ny266, the amino acid positions are indicated with respect to SEQ ID NO: 23. Mutations in the corresponding positions of mutacin 1140 or mutacin B-Ny266 prior to post-translational modification comprising SEQ ID NO: 10 or 11, respectively, are also envisioned.

| Amino acid positions | Original amino acids (respectively) | Replacement amino acid (respectively) |
|---|---|---|
| 12, 14 | Alanine and Threonine | Threonine and Glycine |
| 13, 14 | Arginine and Threonine | Alanine and Alanine |
| 14, 15 | Threonine and Glycine | Alanine and Alanine |
| 5, 14 | Serine and Threonine | Glycine and Glycine |
| 5, 14 | Serine and Threonine | Alanine and Glycine |
| 5, 14 | Serine and Threonine | Threonine and Glycine |
| 5, 14 | Serine and Threonine | Alanine and Serine |
| 5, 14 | Serine and Threonine | Alanine and Alanine |
| 5, 14 | Serine and Threonine | Glycine and Alanine |
| 5, 14 | Serine and Threonine | Glutamate and Alanine |
| 5, 14 | Serine and Threonine | Threonine and Alanine |
| 5, 12 | Serine and Alanine | Alanine and Serine |
| 5, 13 | Serine and Arginine | Alanine and Serine |
| 13, 14 and 15 | Arginine, Threonine and Glycine | Alanine, Alanine and Alanine |
| 5, 13 and 14 | Serine, Arginine and Threonine | Glcyine, Alanine and Alanine |
| 4, 5 and 14 | Tryptophan, Serine and Threonine | Serine, Alanine and Alanine |
| 5, 6 and 14 | Serine, Leucine and Threonine | Alanine, Serine and Alanine |
| 5, 12 and 14 | Serine, Alanine and Threonine | Alanine, Serine and Alanine |
| 5, 13 and 14 | Serine, Arginine and Threonine | Alanine, Serine and Alanine |
| 12, 13 and 14 | Alanine, Arginine and Threonine | Glycine, Glycine and Glycine |

In further embodiments, the invention provides a core peptide mutant of mutacin 1140 comprising SEQ ID NO: 24 or mutacin B-Ny266 comprising the sequence of SEQ ID NO: 23, with the proviso that the core peptide mutant does not contain:

i) amino acid mutations of one or any combination of the second, sixth or thirteenth amino acid residue of SEQ ID NO: 23 or 24 (i.e., the second alone, the sixth alone, the thirteenth alone, the combination of the second and sixth, the combination of the second and thirteenth, the combination of the sixth and thirteenth, or the combination of the second, sixth and thirteenth amino acid residues of SEQ ID NO: 23 or 24);

ii) mutation of one or more of Leu6 and Arg13 to an amino acid selected from alanine, glycine, valine, leucine or isoleucine;

iii) mutation of one or more of Leu6 and Arg13 to alanine; or iv) mutation of Lys2 to an amino acid selected from alanine, glycine, valine, leucine or isoleucine.

A further embodiment of the invention provides a pharmaceutical composition comprising a modified lantibiotic or a functionalized lantibiotic described herein and a pharmaceutically acceptable carrier or excipient. Further embodiments of the invention provide a method of treating a bacterial infection in a subject by administering to the subject a modified lantibiotic or a functionalized lantibiotic described herein. The modified lantibiotic or a functionalized lantibiotic administered to a subject can be in the form of pharmaceutical compositions of the invention.

Decarboxylation of the terminal cysteine in a lantibiotic is typically performed by a decarboxylase, which is typically a flavoprotein. This decarboxylase is specific for C-terminal cysteines from a lantibiotic peptide. Decarboxylation of the C-terminal cysteine produces an ene-thiol intermediate that promotes terminal ring formation. Accordingly, a further embodiment of the invention provides a bacterium that synthesizes a modified lantibiotic. Such bacterium is produced by a genetic modification to a wild-type or a parent bacterium that synthesizes a parent lantibiotic that corresponds to the modified lantibiotic.

Accordingly, certain embodiments of the invention provide a bacterium that synthesizes a modified lantibiotic, wherein the modified lantibiotic has an intact cysteine at the C-terminus, and wherein the bacterium is genetically modified to inactivate a gene that encodes a decarboxylase enzyme that decarboxylates the cysteine at the C-terminus of a precursor lantibiotic.

Several bacteria are known to produce a lantibiotic, for example, Bacillus licheniformis (strain ATCC 14580), Streptomyces sp., Lactobacillus sakei, Streptococcus salivarius, Streptococcus mutans, Lactococcus lactis, Actinoplanes liguriensis, Bacillus sp., Staphylococcus epidermidis, Staphylococcus gallinarum, Streptococcus mutans or Ruminococcus gnavus. Accordingly, certain embodiments of the invention provide a bacterium that synthesizes a modified lantibiotic, wherein the bacterium is Bacillus licheniformis (strain ATCC 14580), Streptomyces sp., Lactobacillus sakei, Streptococcus salivarius, Streptococcus mutans, Lactococcus lactis, Actinoplanes liguriensis, Bacillus sp., Staphylococcus epidermidis, Staphylococcus gallinarum, Streptococcus mutans or Ruminococcus gnavus.

Non-limiting examples of bacterial strains, corresponding lantibiotics and their peptide sequences before the PTMs are provided in Table 4 below.

TABLE 4

Examples of organisms producing lantibiotic and the sequences of unmodified peptides corresponding to mature forms of lantibiotics.

| Name of the organism | Name of the lantibiotic | Sequences in mature form (SEQ ID) | Sequences of propeptide (SEQ ID) |
|---|---|---|---|
| Bacillus licheniformis (strain ATCC 14580) | lichenicidin A2 | 1 | 14 |
| Lactobacillus sakei L45 | lactocin-S | 2 | 15 |
| Streptococcus salivarius | Salivaricin | 3 | 16 |
| Streptococcus mutans | Mutacin-2 | 4 | 17 |
| Lactococcus lactis subsp. lactis (Streptococcus lactis) | lacticin 3147 A2 | 5 | 18 |
| Actinoplanes liguriensis | actagardine | 6 | 19 |
| Bacillus sp. (strain HIL-Y85/54728) | mersacidin | 7 | 20 |
| Staphylococcus epidermidis | Epidermin | 8 | 21 |
| Staphylococcus gallinarum | Gallidermin | 9 | 22 |
| Streptococcus mutans | mutacin B-Ny266 | 10 | 23 |
| Streptococcus mutans | mutacin-1140 | 11 | 24 |
| Ruminococcus gnavus | Ruminococcin-A | 12 | 25 |
| Microbispora corallina | Microbisporicin | 13 | 26 |

For a given bacterium that produces a lantibiotic, a person of ordinary skill in the art can determine which gene encodes a decarboxylase enzyme that decarboxylates the cysteine at the C-terminus of a precursor lantibiotic. For example, EpiD gene from S. epidermidis encodes for a decarboxylase enzyme that decarboxylates the cysteine at the C-terminus of a precursor epidermin. Similarly, MrsD gene from Bacullus sp. encodes for a decarboxylase enzyme that decarboxylates the cysteine at the C-terminus of a precursor mersacidin.

Additional examples of decarboxylase enzymes that decarboxylate the cysteine at the C-terminus of a precursor lantibiotic in other lantibiotic producing bacteria are known in the art and such embodiments are within the purview of the invention.

A gene that encodes the decarboxylase enzyme can be inactivated in a number of genetic modification techniques. For example, a gene that encodes the decarboxylase enzyme can be inactivated by deletion, frameshift mutation(s), point mutation(s), antisense RNA, the insertion of stop codon(s), or combinations thereof. For example, target genes can be inactivated by the introduction of insertions, deletions, or random mutations into the gene that encodes the decarboxylase enzyme. Thus, certain embodiments of the invention provide for the insertion of at least one stop codon (e.g., one to ten or more stop codons) into the gene that encodes the decarboxylase enzyme. Some embodiments of the invention provide for the insertion or deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more bases in order to introduce a frameshift mutation in a gene that encodes the decarboxylase enzyme gene. Other embodiments of the invention provide for the insertion or deletion of 1, 2, 4, 5, 7, 8, 10, 11, 13, 14, 16, 17, 19, 20, 22, 23, 25, 26, 28, 29 or more bases in order to introduce a frameshift mutation in a gene that encodes the decarboxylase enzyme. Yet other embodiments of the subject application provide for the introduction of one or more point mutations (e.g., 1 to 30 or more) within a gene that encodes the decarboxylase enzyme while other embodiments of the invention provide for the partial, total or complete deletion of a gene that encodes the decarboxylase enzyme.

In one embodiment, a gene that encodes the decarboxylase enzyme that decarboxylates the cysteine at the C-terminus of a precursor lantibiotic in a bacterium is inactivated by introducing into the bacterium an inhibitory RNA specifically directed to the gene. In certain embodiments, the inhibitory RNA is an antisense RNA that has an appropriate sequence to inhibit the expression of an mRNA that encodes the decarboxylase enzyme.

Various techniques for carrying out the genetic modifications to inactivate a gene that encodes the decarboxylase enzyme in a bacterium are well known in the art and such embodiments are within the purview of the invention.

In one embodiment, a bacterium that produces a lantibiotic contains endogenous gene cluster that encodes the lantibiotic, i.e., the bacterium naturally produces the lantibiotic. Such bacterium can be genetically modified to inactivate the gene that encodes the decarboxylase enzyme that decarboxylates the cysteine at the C-terminus of a precursor lantibiotic.

In another embodiment, a bacterium that produces a lantibiotic contains exogenous gene cluster that encodes the lantibiotic, i.e., the bacterium is genetically engineered to express the gene cluster that encodes the lantibiotic. Such bacterium can be further genetically modified to inactivate the gene that encodes the decarboxylase enzyme that decarboxylates the cysteine at the C-terminus of a precursor lantibiotic.

In a further embodiment, a bacterium that produces a lantibiotic through exogenous genes that encode the lantibiotic, i.e., the bacterium is genetically engineered to express the genes that encode the lantibiotic does not contain an endogenous gene that encodes the decarboxylase enzyme that decarboxylates the cysteine at the C-terminus of a precursor lantibiotic. In such bacterium, genetic modification to inactivate the gene that encodes the decarboxylase enzyme that decarboxylates the cysteine at the C-terminus of a precursor lantibiotic is not necessary. As such, an embodiment of the invention provides a bacterium that does not contain an endogenous gene that encodes the decarboxylase enzyme that decarboxylates the cysteine at the C-terminus of a precursor lantibiotic and that contains exogenous genes that encode the lantibiotic, i.e., the bacterium is genetically engineered to express the genes that encode the lantibiotic.

A further embodiment of the invention provides a method of producing a modified lantibiotic, wherein the modified lantibiotic has an intact cysteine at the C-terminus. The method comprises the steps of:

a) culturing a bacterium that synthesizes the modified lantibiotic, wherein the bacterium is genetically modified to inactivate a gene that encodes a decarboxylase enzyme that decarboxylates the cysteine at the C-terminus of a precursor lantibiotic, b) purifying the modified lantibiotic from the culture.

The embodiments of the invention discussed above with respect to a bacterium that produces a modified lantibiotic as described herein are applicable to the methods of producing the modified lantibiotic as well.

In certain embodiments, the bacterium is cultured under appropriate conditions for appropriate period of time. A skilled artisan is well-versed with the methods of culturing bacteria and such embodiments are within the purview of the invention.

A step of producing a modified lantibiotic comprises purifying the modified lantibiotic from the culture of the bacterium. Non-limiting examples of such purification methods include liquid chromatography, particularly, fast protein liquid chromatography (FPLC), high-performance liquid chromatography (HPLC), ion exchange chromatography, size-exclusion chromatography, or affinity chromatography. Additional examples of purifying a modified lantibiotic from bacterial culture are known to a skilled artisan and such embodiments are within the purview of the invention.

A further embodiment of the invention provides a method of producing a functionalized lantibiotic by reacting, under appropriate conditions, a modified lantibiotic described herein with a moiety to conjugate the moiety to the carboxyl group of the terminal cysteine. Various moieties described above in connection with the functionalized lantibiotic are also applicable to the methods of making the functionalized lantibiotics described herein.

In one embodiment, a functionalized lantibiotic is produced by 1-Hydroxy-7-azabenzotriazole/1-Ethyl-3-(3-dimethylaminopropyl)carbodiimide (HOAt/EDC) coupling method. Additional techniques for conjugating a modified lantibiotic described herein with a moiety are known to a skilled artisan and such embodiments are within the purview of the invention.

An embodiment of the invention provides a lantibiotic containing one or more amino acid mutations, wherein the lantibiotic containing the one or more amino acid mutations exhibits higher anti-bacterial activity compared to the activity of the lantibiotic being mutagenized. In one embodiment, the invention provides a mutant of a lantibiotic belonging to the epidermin group of lantibiotics, for example, mutacin (e.g., SEQ ID NOs: 4, 10 and 11), epidermin (e.g., SEQ ID NO: 9), gallidermin (e.g., SEQ ID NO: 10), that contains one or more amino acid mutations, wherein the mutant lantibiotic exhibits higher anti-bacterial activity compared to lantibiotic being mutagenized.

Non-limiting examples of a mutant of mutacin 1140 that exhibit higher antibacterial activity compared to mutacin 1140 includes mutations to one or more of Leu6 and Arg13. In one embodiment, a mutant mutacin 1140 contains mutations of one or more of Leu6 and Arg13 to an amino acid selected from alanine, glycine, valine, leucine or isoleucine. In certain embodiment, a mutant mutacin 1140 contains mutations of one or more of Leu6 and Arg13 to alanine.

Non-limiting examples of a mutant of epidermin that exhibit higher antibacterial activity compared to epidermin includes mutations to one or more of Ile6 and Lys13. In one embodiment, a mutant epidermin contains mutations of one or more of Ile6 and Lys13 to an amino acid selected from alanine, glycine, valine, leucine or isoleucine. In certain embodiment, a mutant epidermin contains mutations of one or more of Ile6 and Lys13 to alanine.

Non-limiting examples of a mutant of gallidermin that exhibit higher antibacterial activity compared to gallidermin include mutations to one or more of Lue6 and Lys13. In one embodiment, a mutant gallidermin contains mutations of one or more of Leu6 and Lys13 to an amino acid selected from alanine, glycine, valine, leucine or isoleucine. In certain embodiment, a mutant gallidermin contains mutations of one or more of Leu6 and Lys13 to alanine.

Non-limiting examples of a mutant of mutacin B-Ny266 that exhibit higher antibacterial activity compared to mutacin B-Ny266 includes mutations to one or more of Phe6 and Lys13. In one embodiment, a mutant mutacin B-Ny266 contains mutations of one or more of Phe6 and Lys13 to an amino acid selected from alanine, glycine, valine, leucine or isoleucine. In certain embodiment, a mutant mutacin B-Ny266 contains mutations of one or more of Phe6 and Lys13 to alanine.

A further embodiment of the invention provides a lantibiotic containing one or more amino acid mutations, wherein the lantibiotic containing the one or more amino acid mutations is expressed in higher amounts by the bacterium producing the mutant lantibiotic compared to the bacterium producing the lantibiotic being mutagenized.

In one embodiment, the invention provides a mutant of a lantibiotic belonging to the epidermin group of lantibiotics, for example, mutacin (e.g., SEQ ID NOs: 4, 10 and 11), epidermin (e.g., SEQ ID NO: 9), gallidermin (e.g., SEQ ID NO: 10), that contains one or more amino acid mutations, wherein the mutant lantibiotic is expressed in higher amounts by the bacterium producing the mutant lantibiotic compared to the bacterium producing the lantibiotic being mutagenized.

In one embodiment, the invention provides a bacterium producing a mutant of mutacin 1140 (SEQ ID NO: 11) containing one or more amino acid mutations, wherein the mutant of mutacin 1140 is expressed in higher amounts by the bacterium producing the mutant mutacin 1140 compared to the bacterium producing mutacin 1140.

Non-limiting examples of a mutant mutacin 1140 that are expressed in higher amounts include a mutation of Lys2. In one embodiment, a mutant mutacin 1140 contains mutations of Lys2 to an amino acid selected from alanine, glycine, valine, leucine or isoleucine. In certain embodiment, a mutant mutacin 1140 contains a mutation of Lys2 to alanine.

Non-limiting examples of a mutant mutacin B-Ny266 that are expressed in higher amounts include a mutation of Lys2. In one embodiment, a mutant mutacin B-Ny266 contains mutations of Lys2 to an amino acid selected from alanine, glycine, valine, leucine or isoleucine. In certain embodiment, a mutant mutacin B-Ny266 contains a mutation of Lys2 to alanine.

Certain embodiment of the invention provides a pharmaceutical composition comprising a mutant lantibiotic described herein and a pharmaceutically acceptable carrier or excipient. Further embodiments of the invention provide a method of treating a bacterial infection in a subject by administering to the subject a mutant lantibiotic described herein. The mutant lantibiotic administered to a subject can be in the form of pharmaceutical compositions of the invention.

Further embodiments of the invention provide a bacterium expressing a mutant lantibiotic, particularly, a mutant mutacin 1140 that exhibits higher activity compared to mutacin 1140 or a mutant mutacin 1140 that exhibits higher expression by a bacterium compared to mutacin 1140. Various embodiments discussed above with respect to mutants of mutacin 1140 are also applicable to a bacterium expressing a mutant mutacin 1140. A skilled artisan can readily design a bacterium expressing a mutant mutacin 1140 by transforming a bacterium with a gene or a gene cluster encoding a mutant mutacin 1140 and such embodiments are within the purview of the invention.

Materials and Methods

Bacterial Strains and Media

The bacterial strains and plasmids used in this study are outlined in Table 5. *Streptococcus mutans* strains, *Bacillus subtilis* PY79, *Streptococcus pneumoniae*, and *Micrococcus luteus* ATCC 10240 were grown in either THyex media agar (30 g/L Todd Hewitt Broth, 3 g/L yeast extract, 15 g/L agar; Bacto, Sparks, Md.), THyex broth (30 g/L Todd Hewitt Broth, 3 g/L yeast extract), or THyex top agar (30 g/L Todd Hewitt Broth, 3 g/L yeast extract, 7.5 g/L agar; Bacto, Sparks, Md.). *E. coli* was grown in LB medium (10 g/L tryptone, 5 g/L yeast extract, and 10 g/L NaCl, pH adjusted with NaOH to pH 7.5), Terrific Broth (12 g/L tryptone, 24 g/L yeast extract, 4 mL/L glycerol, and 2.2 g/L $KH_2PO_4$ and 9.4 g/L $K_2HPO_4$), or LB plates (10 g/L tryptone, 5 g/L yeast extract, and 10 g/L NaCl, 15 g/L agar, and pH adjusted with NaOH to pH 7.5).

TABLE 5

Strains used in this study.

| Strain | Plasmid intermediate | Relevant characteristic | Reference or Source |
|---|---|---|---|
| S. mutans JH1140 (ATCC 55676) | | WT bacteriocin producing strain | Strain 1, ATCC |
| S. mutans ΔmutA | | mutA deletion strain | 2 |
| S. mutans IFDC2:mutD | | mutD gene replacement with IFDC2 cassette | This study |
| S. mutans ΔmutD | pΔmutD | Clean deletion of mutD | This study |
| M. luteus ATCC 10240 | | Indicator strain for activity | 3 |
| B. subtilis PY79 | | Indicator strain for activity | 4 |
| S. pneumoniae ATCC 27336 | | Indicator strain for activity | ATCC |
| E. coli DH5α | pCR2.1 and pET28B(+) | Intermediate cloning host | Invitrogen |
| E. coli BL21 | | Protein overexpression host | Invitrogen |

TABLE 5-continued

Strains used in this study.

| Strain | Plasmid intermediate | Relevant characteristic | Reference or Source |
|---|---|---|---|
| E. coli pmutD-kan | pmutD-kan | Codon optimized mutD | This study |
| E. coli pet28B:mutD | pet28B:mutD | MutD overexpression strain | This study |

Gene Deletion of MutD

Primers used for both sequencing and mutagenesis were designed using the S. mutans genome and lan cluster (GenBank/EMBL accession number AF051560) (Table 6). The IFDC2 gene replacement system was used, as previously described, to mutate or delete MutD[30]. In-frame deletion cassette (IFDC2) is a gene replacement cassette containing both a positive selection marker (ermAM) and a negative selection marker (-pheS*). Approximately 500 bp upstream of mutD was amplified and to prevent polar effects of downstream genes of mutD, a 500 bp fragment was amplified starting at 100 bp upstream of the stop codon and 400 bp downstream of mutD. The fragments were attached to the 5' and 3' end of the IFDC2 cassette, respectively, by PCR. The final 3 kb fragment was transformed into S. mutans ATCC 55676 by competent stimulating peptide (CSP) protocol[57]. An overnight culture of S. mutans ATCC 55676 was diluted to 0.1 $OD^{600}$ and incubated at 37° C. to 0.25 $OD^{600}$. Two μl of 10 μg/mL solution of CSP was then added to 200 μl of the 0.25 OD culture. After a 30 minute incubation time at 37° C., 1 μl of the PCR amplified product was added to the culture. The transformation was incubated at 37° C. for 5 hours before plating 50 μl of a 1000-fold dilution onto a THyex plate containing 15 μg/mL of erythromycin. Transformants were confirmed by PCR. The PCR products were inserted into a Topo PCR2.1® plasmid and were sent for sequencing. Both upstream and downstream regions were joined together and amplified to create the ΔmutD fragment. The ΔmutD fragment was transformed into S. mutans IFDC2:mutD, and selected on THyex plates (containing 4 mg/mL of P-Chloro-phenylalanine).

TABLE 6

Primers used in this study.

| Primer | Sequence (5' to 3') | Characteristic |
|---|---|---|
| MutD-UpF | GAT TTG TTT CGT AAA GAG GGT TC (SEQ ID NO: 27) | mutD gene replacement |
| MutD-DnR | CTA CAT CAA TCC CAG AAT CAA C (SEQ ID NO: 28) | mutD gene replacement |
| MutD-UpR-IDH | GAGTGTTATTGTTGCTCGGAAATATTTCTC CGTTCAG TTAA (SEQ ID NO: 29) | mutD gene replacement |
| MutD-DnF-erm | GGTATACTACTGACAGCTTCGGTAATTGTT GGACAAGAATC (SEQ ID NO: 30) | mutD gene replacement |
| DelMutD-F | TTAACTGAACGGAGAAATAATTGGTAATTG TTGGACAAGAATC (SEQ ID NO: 31) | mutD clean deletion |
| DelMutD-R | GATTCTTGTCCAACAATTACCAATTATTTCT CC GTTCAGTTAA (SEQ ID NO: 32) | mutD clean deletion |

Bioactivity Assays

The deferred antagonism assay was performed as previously described[39]. S. mutans strains were grown overnight in THyex broth at 37° C. The cultures were diluted to 0.1 OD $OD_{600}$ and grown to mid-logarithmic phase before diluting to 0.05 $OD_{600}$. Then, 2 μl of the cultures were spotted on THyex plates in duplicates of triplicates. The wild-type S. mutans JH1140 and S. mutans ΔmutA were used as positive and negative controls for activity, respectively. The plates were incubated for 18 hours in a candle jar at 37° C. After incubation, the strains were heat killed at 65° C. for 90 minutes. Fresh M. luteus grown overnight at 37° C. on THyex plates were used to inoculate pre-warmed THyex broth. The culture was grown to 0.6 to 0.8 OD before diluting to 0.2 $OD_{600}$. The culture was further diluted 25-fold in melted (42° C.) THyex top agar. Approximately 5 mL of the top agar solution was spread on the heat killed bioassay plates and allowed to cool for 10 minutes. The plates were then placed in the incubator (at 37° C.) for 18 hours.

Minimum Inhibitory Concentrations (MICs) were determined according to previously published protocol[31]. A stock solution of the antibiotics tested was first suspended in 50% acetonitrile (ACN) at a concentration 640 μg/mL. This stock was subsequently diluted 2-fold until a final concentration 0.156 μg/mL was reached. Subsequently, 10 μl of each dilution was placed into a well on a 96 well microtiter plate. M. luteus ATCC 10240, S. pneumoniae, and B. subtilis PY79 were grown overnight in THyex at 37° C. Cultures were diluted in the morning to 0.1 $OD_{600}$ and allowed to grow to 0.6 $OD_{600}$. This culture was diluted a 100-fold in fresh THyex media and then 400 μl of this culture was added to 10 mL of fresh THyex. The suspension contains approximately $10^5$ colony forming units (CFUs). The bacterial suspension (190 μL) was added to each well containing 10 μL of antibiotic suspension or solvent blank. This resulted in another 20-fold dilution of the antibiotic suspension. For the competition assays, $10^5$ CFU bacterial suspension was initially mixed with mu1140-COOH for 15 minutes at the 1×MIC of either mutacin 1140 (0.25 μg/mL and 0.125 μg/mL for B. subtilis and M. luteus, respectively) or nisin (0.5 μg/mL for B. subtilis and M. luteus). Following the 15 minute pretreatment, 190 μL was added to each well as described above. The MIC is described as the highest concentration of antibiotic that prevented visible growth after 24 hours.

Production and Purification of Mutacin 1140 and mu1140-COOH

Lanthipeptides isolated in this study were cultured as stated previously[58]. S. mutans strains were grown in a modified THyex media. The media contained 30 g/L Todd Hewitt, 3 g/L yeast extract, 1 g/L $NaH_2PO_4$, 0.2 g/L $Na_2HPO_4$, 0.7 g/L $MgSO_4$, 0.005 g/L $FeSO_4$, 0.005 g/L $MnSO_4$, and 0.3% agar. The semi-solid agar (1 L) was inoculated with various strains of S. mutans and incubated at 37° C. for 72 hours. After incubation, the inoculum was frozen at −80° C. overnight and thawed for 1 hour in a 65° C. water bath. The inoculum was then centrifuged at 20,000 g for 30 minutes and the supernatant was collected. The supernatant was mixed with chloroform at 1:1 ratio and mixed vigorously. This mixture was again centrifuged at 20,000 g for 30 minutes. The precipitate between both the aqueous and chloroform phases was collected and dried overnight. The dried product was resuspended in 35% ACN containing 0.1% trifluoroacetic acid (TFA) and ran on either a semi-prep C18 column (Agilent® ZORBAX, ODS, C18, 5 μm, 4.6×250 mm) or analytical column. Peaks collected were confirmed by mass on a Shimadzu® MALDI-MS on both linear and reflectron modes.

Chemical Modification of mu1140-COOH and Nisin

Labeling of C-terminal carboxyl group with methylamine (33% in EtOH) (Sigma-Aldrich), diaminoheptane (Sigma-Aldrich), chlorophenylalanine (Sigma-Aldrich), di-chlorophenylalanine (Sigma-Aldrich), or 5-(aminoacetamido)fluorescein (Sigma-Aldrich) was done by 1-Hydroxy-7-azabenzotriazole/1-Ethyl-3-(3-dimethylaminopropyl) carbodiimide (HOAt/EDC) coupling. The labeling was done in according to a previously described method[16, 39]. The reaction mixture was suspended in 100 µl of Dimethyl Formamide (DMF) with 50 nmols of either nisin, or Mu1140-COOH, 50 nmols AAA-fluorescein or 200 nmols of the primary amine, 60 nmols of 1-Ethyl-3-(3-dimethylaminopropyl)carbodiimide (EDC), and 60 nmols of 1-Hydroxy-7-azabenzotriazole (HOAt). The reaction was covered in foil and incubated at room temperature for approximately 16 hours. The reaction was subsequently diluted 10-fold with 35% ACN containing 0.1% TFA and ran on an analytical C-18 column. The labeled peptides were confirmed by MALDI-MS as described above. The amount of chemically conjugated product was determined by Bradford Assay using manufacturer recommended protocol (Sigma-Aldrich). The purified labeled peptides were then dried down and resuspended in 35% ACN containing 0.1% TFA at a concentration of 100 ug/mL and stored at −20° C.

Microscopy

B. subtilis PY79 was grown and treated with fluorescein labeled peptide as previously described[39]. A fresh plate of B. subtilis was used to inoculate THyex broth and incubated approximately 16 hours at 37° C. The culture was diluted 20-fold and placed back in the incubator for 3 hours at 37° C. Then, 100 µl of the culture was incubated with the antibiotic (10 µg/mL) for 15 minutes. The cells were pelleted and resuspended in 100 µl of phosphate buffer solution (PBS). The wash step was repeated three times before fixing with 1.6% formaldehyde in PBS. After fixation the cells were washed with PBS three more times and the remaining pellet was suspended in 50 µL of PBS. The sample (30 µL) was added to a slide and observed using an Olympus confocal microscope with a 100×/0.90 dry objective. A 488 nm argon laser was used to excite the fluorophore. For the competition assay, the bacterial culture was initially incubated with mu1140-COOH or native mutacin 1140 at a concentration of 10 µg/mL for 15 minutes, washed, and resuspended in fresh media. 10 µg/mL of fluorescein labeled nisin was then added for 15 minutes, before following the wash protocol previously stated.

Mu1140 Double Labeling and Edman Sequencing

Edman sequencing has been frequently used to determine the sequence of small peptides, such as lantibiotics[59-60]. Mu1140-COOH was doubly labeled as previously described for mutacin 1140[32]. A 200 µM solution of Mu1140-COOH in 5 µl of water was added to a reaction tube containing 2 mg of sodium borohydride. Then, 94 µL of solution B (570 mg guanidine HCl, 100 mL N-ethylmorpholine and water to a final volume of 1 mL; the pH of the mixture was adjusted to 8.5 with glacial acetic acid) was added to the reaction mixture and placed into a glass vial. The reaction vial was purged with nitrogen and stored at 37° C. for three days. The peptide was then loaded onto a prosorb column (Applied Biosystems) and absorbed onto a PVDF membrane. After drying the PVDF membrane, 15 µl of solution A (280 µL methanol, 200 µL water, 65 µL 5 M sodium hydroxide, 60 ethanethiol) was added to the membrane. The reaction was sealed tightly and incubated at 50° C. for 1 hour. After the reaction, the sample was sent out for Edman sequencing. The glass fiber filter used in the Edman sequencing was pretreated with polybrene to reduce the loss of peptide per cycle. After drying in nitrogen, the PVDF membrane was excised and loaded onto a sequencer (Applied Biosystems 492 Protein P.E. Biosystems, Foster City, Calif., USA). The sequence was analyzed by the ABI 610A data software. D,L-2-aminobutyric acid was commercially purchased from Sigma Aldrich and used as a standard.

MutD Cloning and Purification

A codon optimized sequence of mutD for E. coli was purchased from Integrated DNA Technologies (IDT, Coralville, Iowa). According to manufacturer's specifications, mutD gene was cloned into the XhoI site within the pET28B (+) expression vector (EMD Millipore, Billerica Mass.) providing an N-terminal His-tag. The ligation was transformed into E. coli DH5α and confirmed by sequencing. The plasmid was then transformed into the E. coli BL21 expression strain. A fresh plate of E. coli BL21 pET28B(+):mutD was restreaked onto LB plate containing 50 µg/mL kanamycin (kan) prior to induction. One colony from the plate was suspended in 1 L of Terrific broth containing 50 µg/mL kan. Before the addition of IPTG (250 µl of a 1M solution), the culture was shaken at 37° C. until an $OD_{600}$ of 0.8 was reached. Following induction, the culture was incubated with shaking at 18° C. for approximately 16 hours. The culture was then spun at 4000 g for 30 minutes at 4° C. The pellets were resuspended in 25 mL of lysis buffer (500 mM NaCl, 50 mM Tris-HCl, 15 mM imidazole, 1 mM PMSF, 10% glycerol, at pH 7.5), before adding 500 µl of the lysozyme solution (50 mg/mL). The solution was mixed and stored on ice for 30 min. The suspension was lysed using a sonicator at medium setting for 10 minutes with 1 minute intervals, taking care to not overheat the solution. The lysate was then centrifuged at 16,000 g and the supernatant was collected. 500 µl of Ni-NTA beads were added to the supernatant and placed on a shaker for approximately 16 hours at 4° C. The Ni-NTA beads were collected by centrifugation at 3,000 RPM for 10 minutes at 4° C. The beads were washed three times with 10× bead volume of lysis wash buffer (500 mM NaCl, 50 mM Tris-HCl, 30 mM imidazole, 1 mM PMSF, at pH 7.5). After washing, the beads were eluted by resuspending in 500 µL of lysis buffer containing 0.5 M Imidazole. The suspension was place on a shaker for 1 hour at 4° C. and the elution was repeated three times. The elutions were run on an SDS Page gel to determine purity of the MutD. The decarboxylase was further run on an FPLC. Protein concentrations were determined by Bradford assay (Sigma-Aldrich).

In vitro Decarboxylation

In vivo decarboxylation was performed as previously described[21]. A control substrate, SFNSYTC was purchased from Peptide&Elephants. 1 mg/mL solution of either SFNSYTC or mu1140-COOH in Tris-HCl buffer (pH 8.0) containing 3 mM DTT was prepared. The peptide solution (100 µL) was incubated with MutD (30 µg/mL) for 1 to 10 hours at 37° C. The sample was diluted 10-fold in 35% ACN containing 0.1% TFA before being loaded on the RP-HPLC as previously described[31]. The masses of the isolated fractions were determined by MALDI-TOF.

Lipid II Binding Assay

Lipid II was a kind gift from Eefjan Breukink and was resuspended in a 1:1 Methanol:Chloroform solution. The lipid II binding assay using thin layer chromatography (TLC) was done as previously described[39]. The mobile solvent consisted of consisted of butanol:acetic acid:water:pyridine (15:3:12:10 [vol/vol/vol/vol]). A 0.2 mM solution of mutacin 1140 or mu1140-COOH in 10 µL of solution A was mixed with lipid II (final 6.8 mM) for 1 hour in a sealed glass vial. This corresponded to a ratio 3:10 peptide:lipid II ratio. All of the reaction mixtures and the appropriate controls were spotted (5 μL) 2 cm from the bottom of the plate. These spots define the origin of the plate. Lipid II and peptide alone were used as a control to demonstrate that the origins do not stain unless peptide and lipid II are added together. The mobile phase was allowed to climb up the plate until it reached a centimeter from the top. The plate was allowed to dry before staining with iodine.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Figure 5A:
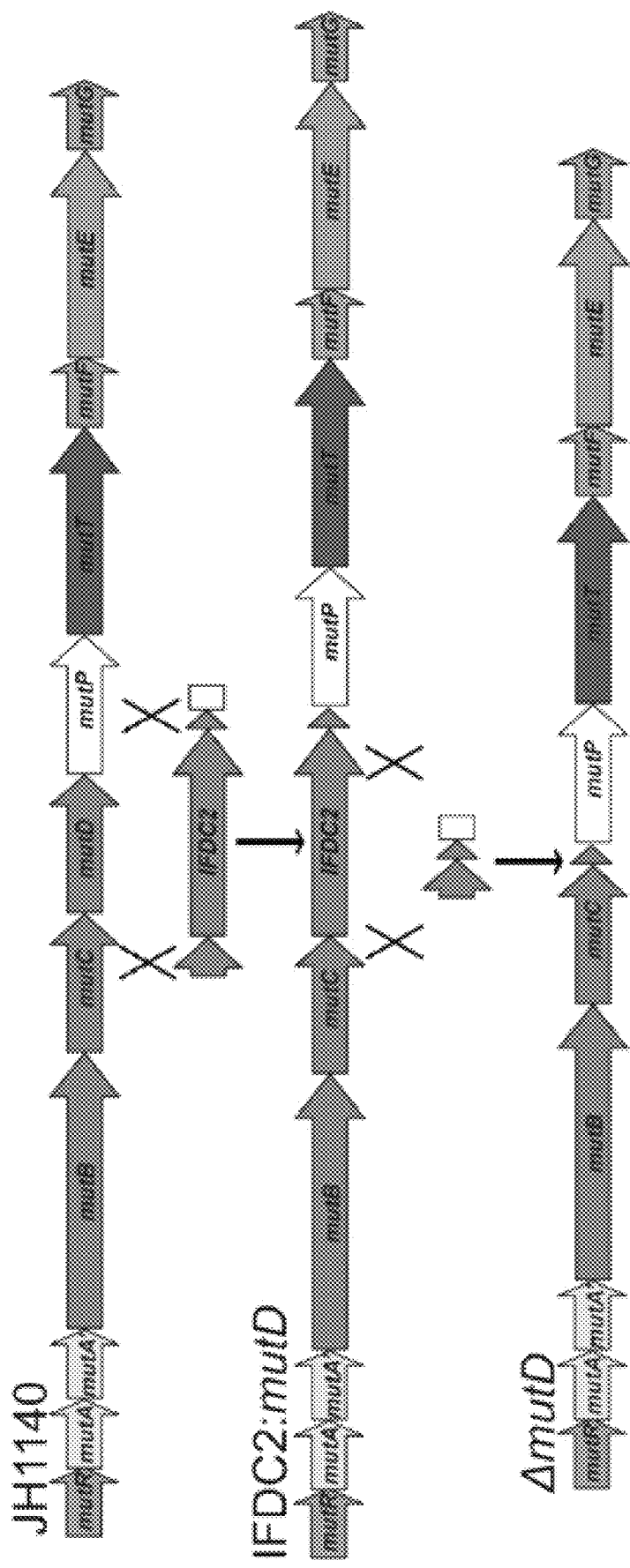
FIGS. 5A-5C. Deletion of mutD in *S. mutans* JH1140. (A) Scheme for the deletion of mutD by IFDC2 gene replacement. (B) Deferred antagonism assay against *M. luteus* ATCC 10240 shows no zone of inhibition for either *S mutans* IFDC2:mutD or *S. mutans* ΔmutD. *S. mutans* JH1140 and *S. mutans* ΔmutA were used as a positive and negative controls, respectively. (C) Purification of *S mutans* IFDC2:mutD extracts (green) show a single peak, while there was no observable peak for *S. mutans* ΔmutA and ΔmutD.
Figure 5B:
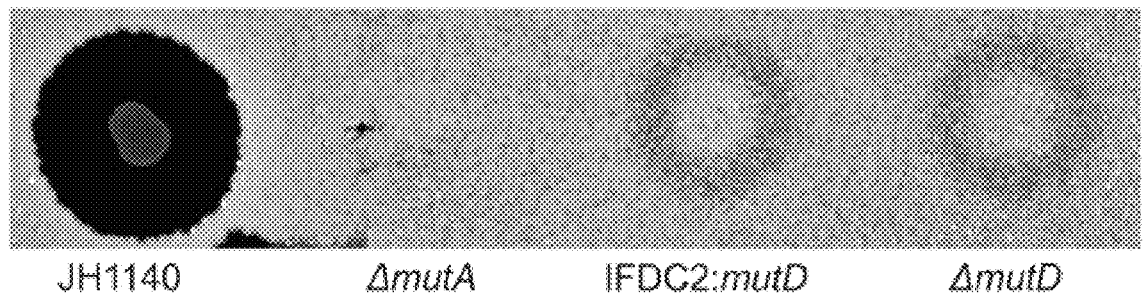
Figure 5C:
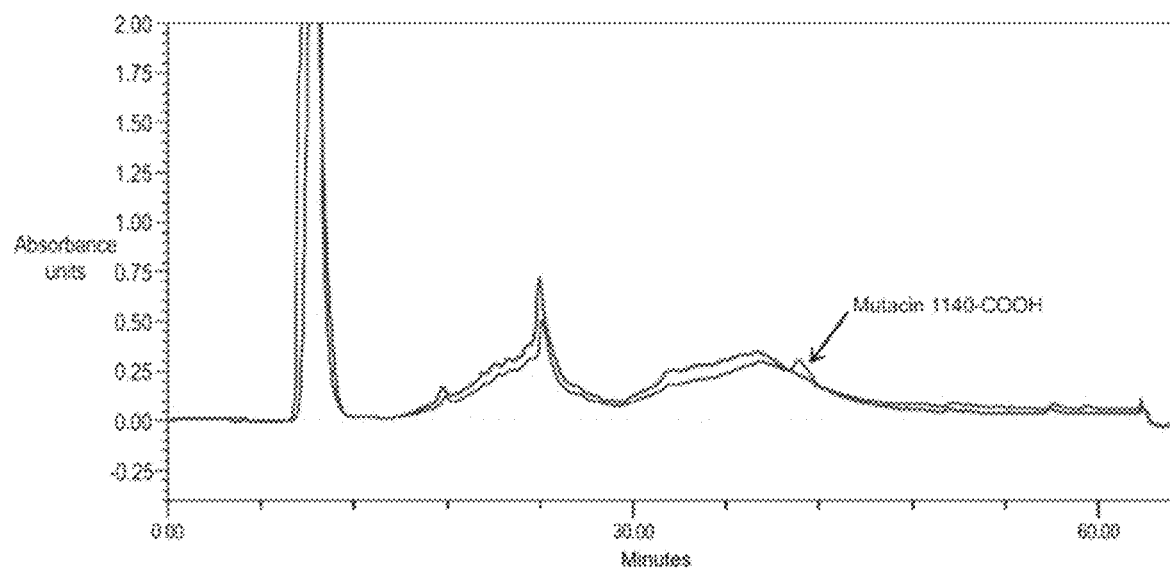

Example 1—Engineering a C-terminal Carboxyl Analog of an Epidermin Group Lantibiotic A C-terminal carboxyl analog for the epidermin group of lantibiotics has not yet been characterized. Several structural analogs of mutacin 1140 were identified when the formation of ring B was disrupted by a C(11)A mutation. The mutation interfered with the formation of the PTMs normally found within mutacin 1140 and one of the peptide analogs had not undergone a C-terminal decarboxylation[29]. This observation supported the basis for engineering S. mutans JH1140 to produce a mutacin 1140 C-terminal carboxyl analog (mu1140-COOH). Deletion or insertional mutagenesis of mutD was done using the IFDC2 gene replacement system (FIG. 5a)[30]. A deferred antagonism assay, using the indicator strain Micrococcus luteus ATCC 10240, was performed on the S. mutans insertional IFDC2:mutD and S. mutans ΔmutD mutant strains. Neither mutant strains had a clear zone of inhibition (FIG. 5b), suggesting that the mutants did not produce a product or that the product was inactive. The culture broth of each mutant was extracted using the same extraction method for wild-type mutacin 1140. These extracts were run on an HPLC, as previously described[31]. There was no observable product for the ΔmutD strain. The ribosomal binding site (RBS) for mutP protease is within the 3' end of the mutD gene. Careful consideration was made to leave the RBS site in the deletion strain. However, there may be other elements important for the synthesis of downstream products that are not readily apparent. Nevertheless, a single HPLC peak for IFDC2:mutD strain was isolated and further characterized (FIG. 5c). The IFDC2 cassette is under the control of a constitutive lactose dehydrogenase (ldh) promoter and this promoter may facilitate the expression of the downstream genes. The purified product from this mutant was analyzed by MALDI-TOF mass spectrometry and had a mass of 2310 Da. This mass corresponded to the expected mass of a C-terminal carboxyl analog of mutacin 1140. A minimum inhibitory concentration (MIC) assay performed using mu1140-COOH analog against M. luteus revealed a 256-fold reduction in activity compared to wild type mutacin 1140. Furthermore, the activity of mu1140-COOH against Streptococcus pneumoniae ATCC 27336 was greater than 64 μg/mL, which is more than a 128-fold reduction in activity (Table 7). The loss in activity in the MIC assays further corroborates the lack of activity seen in the deferred antagonism assays. The reason for the lack of activity may be attributed to the presence of the carboxyl group or it could indicate that the presence of the carboxyl group has disrupted the occurrence of other PTMs found in mutacin 1140.

TABLE 7

Mass and activity of chemically modified analogs of mutacin 1140 against select bacteria.

| Mutacin 1140 analog | Expected Mass (Da) | Observed Mass (Da) | MIC (μg/mL) M. luteus | MIC (μg/mL) S. pneumoniae |
|---|---|---|---|---|
| Mutacin 1140 | 2264.63 | 2264.63 | 0.125 | 0.5 |
| Mu1140 - COOH | 2310.65 | 2310.63 | 32 | >64 |
| Mutacin 1140 - methylamine | 2325.72 | 2325.42 | 0.125 | 0.5 |
| Mutacin 1140 - diaminoheptane | 2422.88 | 2421.97 | 0.25 | 2 |
| Mutacin 1140 - chlorophenylalanine | 2436.25 | 2435.80 | 1 | 8 |
| Mutacin 1140 - di-chlorophenylalanine | 2470.69 | 2468.26 | 4 | 8 |

Figure 6A:
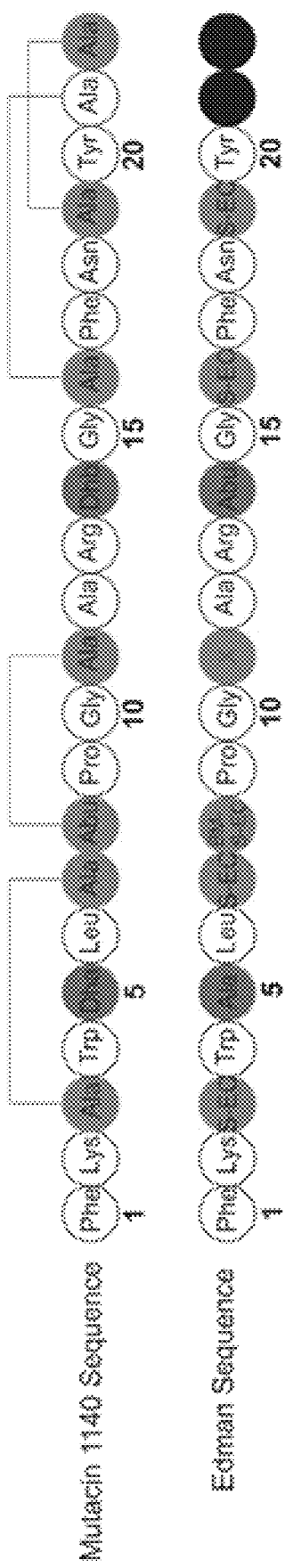
FIGS. 6A-6B. Edman sequencing of mutacin 1140-COOH. (A) After double labeling with sodium borohydride and ethanethiol, a thio-ethyl cysteine (S-EC) or beta-methyl thio-ethyl cysteine (BM-S-EC) is expected at sites of lanthionine ring formation in the Edman sequence compared to mutacin 1140 (SEQ ID NO: 37). Blue circles indicate residues expected to form lanthionine rings, and green circles indicate sites of dehydration. (B) Select Edman sequence (SEQ ID NO: 38) spectras for the modified residues indicate full modification of mu1140-COOH. The red X or black circles indicate residues with no signal acquired.
Figure 6B:
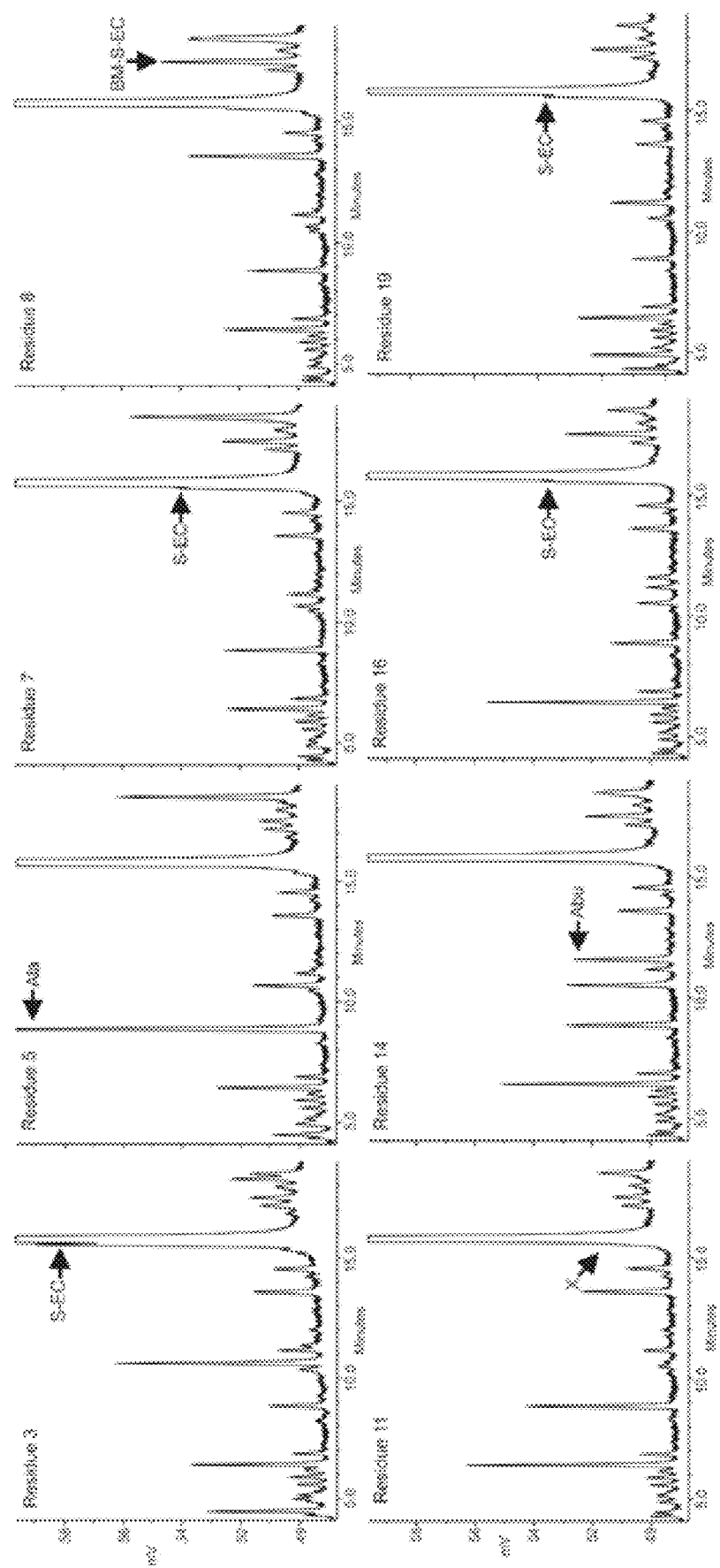

MALDI-TOF mass analysis can determine dehydrations due to an observable change in mass. It cannot determine the formation of a lanthionine ring after dehydration, since the PTM does not result in a change in mass of the peptide. Therefore, the formation of the lanthionine rings was assessed by another method. A rapid and straight forward Edman sequencing method has been developed to distinguish between dehydrated residues and dehydrated residues involved in lanthionine ring formation[32]. Dehydrated residues are first hydrated by sodium borohydride before lanthionine ring derivatization by an organothiol compound. This method can determine where the lanthionine rings are formed and the location of all the dehydrated residues, thus, elucidating the covalent structure of the lantibiotic peptide. Sodium borohydride reduction of Dha and Dhb residues result in the formation of alanine and 2-aminobutyric acid, respectively. Subsequent ethanethiol derivatization open the lanthionine rings, which form either thioethyl cysteines (S-EC) or β-methylthioethyl cysteines (β-M-S-EC). The presence of an S-EC or BM-S-EC residue at the amino acid positions 3, 8, 16, and 19 indicate that the free thiols of upstream cysteines had reacted with their downstream dehydrated residues to form a lanthionine ring. Alanine and 2-aminobutyric acid were observed in positions 5 and 14, respectively (FIG. 6). These correspond to the reduction of the Dha5 and Dhb14 residues. S-EC or BM-S-EC residues were observed in the expected amino acid positions 3, 8, 16, and 19 (FIG. 6), confirming that they are involved in lanthionine ring formations. These data suggest that the loss of activity is not due to disruptions to the other PTM's and that the observed loss in bioactivity of the mu1140-COOH analog is due to the presence of a C-terminal carboxyl group.

These results also demonstrate that the presence of the AviCys residue is not essential for the activity of a lantibiotic; however, the removal of the carboxyl group of the cysteine at the C-terminus is essential for the activity of a lantibiotic.

Example 2—Restoration of Bioactivity of the C-Terminal Carboxyl Analog of an Epidermin Group Lantibiotic Removal of the carboxyl group by MutD was attempted to confirm that the presence of the C-terminal carboxyl group is responsible for the loss in bioactivity. A C-terminal histidine tag of MutD was constructed and overexpressed in

*Escherichia coli*. The purified product on an SDS-PAGE gel had the expected monomer size of 25 kDa; however, subsequent purification through FPLC showed a product that was approximately 200 kDa. 200 kDa mass is consistent with the formation of a homododecamer, as was previously reported for the epidermin decarboxylase EpiD[23]. To determine if the enzyme was active, a reference peptide SFN-SYTC was incubated with MutD for one hour. A mass of 797.67 Da determined by MALDI-TOF was observed for the reference peptide compared to 843.69 Da for the unreacted peptide, indicating that the decarboxylase was active (Table 8). mu1140-COOH analog was incubated with MutD for one or ten hours and showed no indication of a mass change by MALDI-TOF (Table 8). MutD was not capable of decarboxylating the mu1140-COOH analog.

TABLE 8

Mass of mu1140-COOH and control peptide after in vitro decarboxylation with MutD.

| Substrate | Mass before reaction (Da) | Expected mass (Da) | Observed mass (Da) |
|---|---|---|---|
| SFNSYTC (1 hr) | 843.69 | 797.67 | 797.67 |
| Mu1140-COOH (1 hr) | 2310.37 | 2265.37 | 2310.63 |
| Mu1140-COOH (10 hr) | 2310.37 | 2265.37 | 2310.63 |

Figure 2:
FIG. 2. Scheme for chemical modification of mutacin 1140-COOH. Mu1140 COOH analog was coupled to various primary amines using HOAt/EDC coupling. Primary amines were chosen based on size and differences in physiochemical properties. Reaction conditions were constant for each substrate, and yields were greater than 80% for each substrate.

Given that MutD was not capable of removing the C-terminal carboxyl group, the C-terminal carboxyl group was chemically modified and tested to determine whether C-terminal substitutions could restore the bioactivity. EDC coupling of primary amines was used to cap the C-terminal carboxyl group (FIG. 2). None of the primary amines, tested on their own, had any activity against the indicator strains used in this study. EDC coupling with methylamine, the smallest primary amine, was first attempted. The conjugation with methylamine yielded a product with a mass of 2321 Da, indicating that the reaction occurred (Table 7). Based on the RP-HPLC spectra, the reaction did not yield any other side products and the methylamine product was greater than 95% of the material. There was a small amount of unreacted mu1140-COOH analog eluting before the conjugated methylamine product. The methylamine conjugated mutacin 1140 analog had an MIC of 0.125 µg/mL against *M. luteus*, and 0.5 µg/mL MIC against *S. pneumoniae*. These values were the same as the MIC values for native mutacin 1140. These results show that capping mu1140-COOH with a small primary amine restores activity to wild type levels. This data also supports the notion that the presence of a C-terminal carboxyl group is responsible for the reduction in mu1140 activity.

mu1140-COOH was then conjugated with diaminoheptane. The activity of the diaminoheptane conjugate was 0.5 µg/mL against *M. luteus* and 2.0 µg/mL against *S. pneumoniae*. The addition of two different chlorinated aromatic rings with mu1140-COOH was also tested. The activity of chlorophenylalanine conjugate was 1.0 µg/mL against *M. luteus* and 2.0 µg/mL against *S. pneumoniae*. For the dichlorophenylalanine conjugate, the activity was 1.0 µg/mL and 8.0 µg/mL against *M. luteus* and *S. pneumoniae*, respectively. All the conjugates restored the activity of the mu1140-COOH analog, supporting the synthesis of a library of analogs that can be screened for novel applications.

Figures 3A, 3B, 3C:
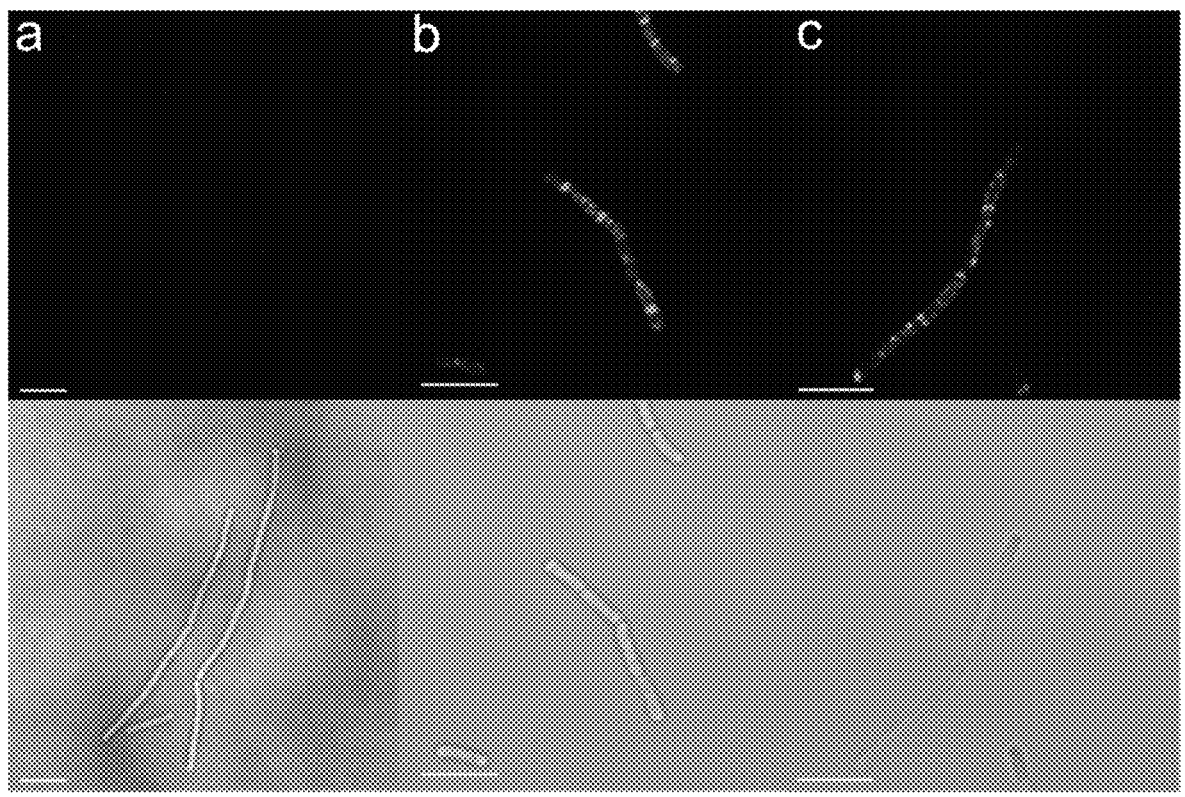
FIGS. 3A-3C. In vivo localization of mutacin 1140. *B. Subtilis* PY79 cells were incubated with various fluorescein conjugated lantibiotics. (A) A no antibiotic sample was used as negative control. (B) Fluorescein conjugated nisin binds and abducts lipid II to form patches as expected. (C) Fluorescein conjugated mutacin 1140 has a similar localization pattern as nisin. Images were taken using a confocal Olympus microscope using a 100× objective, or a 40× objective for the control.

Fluorescently labeled nisin, containing a C-terminal conjugate of fluorescein, has been shown to form lipid II patches on the surface *Bacillus subtilis* cells[16]. The binding of lipid II by an epidermin group of lantibiotics has been shown in various in vitro assays[33]; however, the bioactivity has never been visualized in vivo. This is due to the lack of amenable attachment site for a fluorophore. The free carboxyl group on the mu1140-COOH analog provides one such site. A C-terminal fluorescein conjugate of mutacin 1140 was evaluated. The product had the expected mass of 2623 Da and has the inhibitory activity in a deferred antagonism assay. For comparison, a C-terminal fluorescein conjugate of nisin was also made as previously described[16]. As shown by Hasper et al., *B. subtilis* cells incubated with fluorescein labeled nisin showed large green patches on the cell surface (FIG. 3). The green patches have been attributed to lipid II abduction and sequestration by nisin from its normal physiological location. The C-terminal fluorescein labeled mutacin 1140 produces a similar pattern of fluorescent patches as observed by nisin (FIG. 3). This data supports in vitro data from the epidermin group of lantibiotics for lipid II binding and sequestration and also demonstrates that this group of lantibiotics does sequester lipid II from its normal physiological location for cell wall synthesis.

Example 3—The Loss of Activity for the C-Terminal Carboxyl Analog Of Mutacin 1140

Figures 4A, 4B, 4C, 4D:
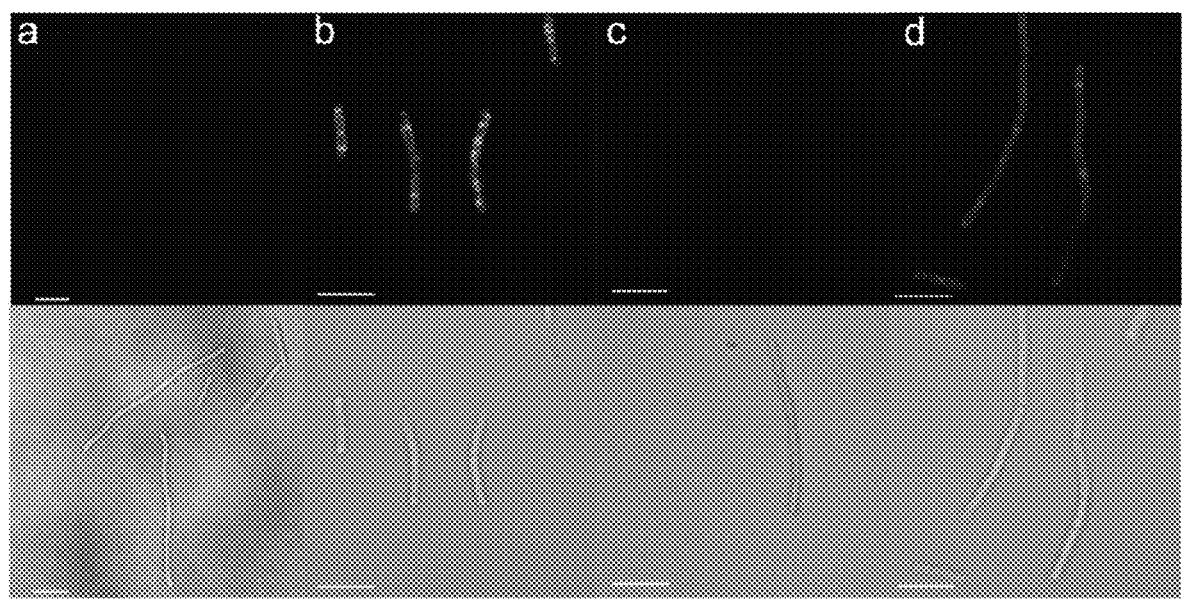
FIGS. 4A-4D. Lipid II competition assay of nisin and mu1140-COOH analog. *B. subtilis* cells were treated with mu1140-COOH to compete with nisin in binding to lipid II. (A) Solvent blank (no antibiotic) control. (B) Fluorescein labeled nisin binds tightly to lipid II to form patches. (C) Prior treatment of cells with mu1140 prevents binding of fluorescein labeled nisin. (D) Prior treatment of cells with mu1140-COOH drastically reduces binding of fluorescein labeled nisin. Images were taken using a confocal Olympus microscope using a 100× objective, or a 40× objective for the control.
Figure 7:
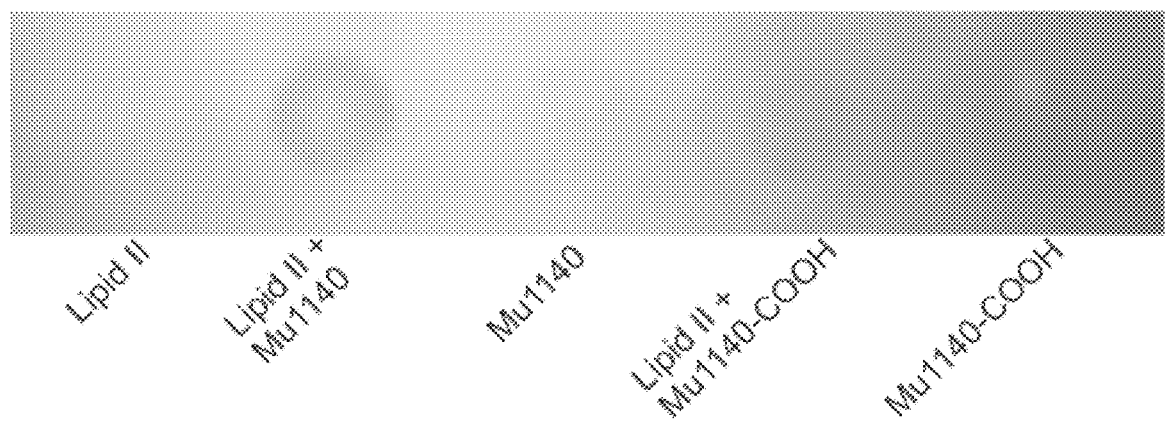
FIG. 7. In vitro lipid II binding assay. TLC plate assay of mutacin 1140 or mu1140-COOH mixed with lipid II. Binding of lipid II will keep lipid II at the origin. Lipid II or mu1140-COOH by itself was used as a negative control showing no staining. Lipid II and mutacin 1140 was used as a positive control for trapping lipid II at the origin.

With the loss of activity associated with a free carboxyl group in mu1140-COOH, the basis for the loss in activity was studied. The mechanism of action for class I lantibiotics has been determined to be due to lipid II binding[34-36]. In particular, rings A and B are believed to form a cage-like structure around the pyrophosphate moiety of lipid II[37]. The latter half of the peptide is predicted to enhance binding and recruit other lipid II-lantibiotic molecules into a large lipid II-lantibiotic complex[16]. Given that lipid II binding is done by the N-terminal rings A and B, it is likely that the loss of activity is due to a loss in the lateral assembly function of the latter half of the peptide. To test for this assumption, a series of experiments were performed to determine whether the mu1140-COOH would bind to lipid II or competitively block lipid II binding of nisin in vivo. A TLC plate assay was used to determine if mu1140-COOH could bind to lipid II, as has been previously reported for gallidermin[38]. If lipid II migration on the TLC plate is impeded by binding to mutacin 1140 or mu1140-COOH, an iodine stained spot is observed at the origin. No stain was visible for mutacin 1140, mu1140-COOH, and lipid II, when the compounds were spotted alone. A stained spot did appear at the origin when mutacin 1140 and mu1140-COOH were spotted with lipid II (FIG. 7). The mu1140-COOH analog mixed with lipid II showed a faint stain compared to lipid II mixed with wild-type mutacin 1140. The faint staining may be attributed to a weaker association of mu1140-COOH with lipid II than mutacin 1140. If mu1140-COOH is capable of binding to lipid II, but does not inhibit cell growth, it may provide resistance to a bacterium against mutacin 1140 or nisin. A competition MIC for mutacin 1140 and nisin was then performed against *B. subtilis* and *M. luteus* that were pretreated with mu1140-COOH. *B. subtilis* and *M. luteus* were pretreated with mu1140-COOH at 0.25 µg/mL and 0.125 µg/mL, respectively, before adding mutacin 1140. Mu1140-COOH competitively inhibited the activity of mutacin 1140 against *B. subtilis* and *M. luteus* by 4-fold (MIC 1.0 µg/mL and 0.5 µg/mL, respectively) (Table 9). When pretreated with 0.5 µg/mL of mu1140-COOH, the activity of nisin was competitively inhibited against *B. subtilis* and *M. luteus* by 4-fold and 2-fold, respectively (MIC 2.0 µg/mL and 1.0 µg/mL). To further clarify a mechanism of action for the loss of activity in the MIC competition assay, confocal microscopy was used to observe nisin binding as previously described[39]. If mu1140-COOH is still binding to lipid II in vivo, it should competitively inhibit the binding of fluorescein labeled nisin (FIG. 4). When the bacteria were pre-treated with wild-type mutacin 1140 or mu1140-COOH, no typical in vivo fluorescence pattern was observed for the fluorescein labeled nisin (FIG. 4). However, there was some association of fluorescein labeled nisin with the bacteria, but nothing remotely similar to fluorescein labeled nisin on its own. This may be due to the weaker association of mu1140-COOH to lipid II, which further corroborates the weak association with lipid II observed in the TLC assay. These results suggest that the loss in activity is not due to its inability to bind to the lipid II target, but due to its inability to form the large lantibiotic lipid II complexes.

TABLE 9

Competition MICs of mutacin 1140 or nisin against *B. subtilis* and *M. luteus* preincubated with mu1140-COOH.

| Antibiotic | B. subtilis MIC (µg/mL) | B. subtilis comp. MIC (µg/mL) | M. Luteus MIC (µg/mL) | M. Luteus comp. MIC (µg/mL) |
|---|---|---|---|---|
| Mutacin 1140 | 0.25 | 1.0 | 0.125 | 0.5 |
| Nisin | 0.5 | 2.0 | 0.5 | 1.0 |

Example 4—MUTACIN 1140 is Post-Translationally Modified Despite Decarboxylation at the C-Terminus Decarboxylation in mutacin 1140 is not needed for the other PTM modifications; a fully modified analog of mutacin 1140 with a C-terminal carboxyl group (mu1140-COOH) can be isolated and purified and the bactericidal activity can be restored by labeling the carboxyl group with a primary amine. Also, a fluorescein conjugated mutacin 1140 can be synthesized, enabling in vivo visualization of mutacin 1140 bound to lipid II target. Further, the loss of activity of the mu1140-COOH analog is likely due to the carboxyl group disrupting mutacin 1140 lipid II complex formation and not due to the complete loss of lipid II binding. A lateral assembly mechanism that traps lipid II into a complex for bactericidal activity may be necessary, which is distinct for other lipid II binding antibiotics, i.e. vancomycin[40]. Furthermore, at generating a C-terminal labeled library of mutacin 1140 analogs may expand the lantibiotics' application or therapeutic use.

A variant of the epidermin group of lantibiotics with a C-terminal carboxyl group is provided. Deletion of EpiD did not show activity; however, no discussion of an isolated product was mentioned[25]. This is presumably due to the lack of a product as was observed in the mutD deletion strain. Increasing activity or developing new uses for existing lantibiotics has been a goal of many researchers in the field. This has been achieved through a variety of methods, such as amino acid substitutions and the use of non-proteogenic amino acids[26, 41-42]. Semi-synthetic analogs of lantibiotics have been produced by chemically modifying lantibiotics[43-44]. The most common chemical modification of lantibiotics is through reactions with a free C-terminal carboxyl group. NVB302, is one such variant that has been chemically modified to have a diaminoheptane tail. This analog of actagardine has made it through phase I clinical trials[27]. Until the isolation of the mu1140-COOH analog, the presence of an AviCys residue on the epidermin group of lantibiotics prevented further development of novel analogs. The addition of a chlorinated aromatic ring may confer additional characteristics to mutacin 1140, as is seen in vancomycin analogs in which the vancomycin analog inhibited transglycosylase activity[45]. Additionally, a diaminoheptane tail was conjugated to mutacin 1140, similar to NVB302. All of these analogs were bioactive.

Visualization of the bioactivity by the epidermin group of lantibiotics was limited to in vitro assays due the inability to conjugate a detectable label, for example, a fluorescent probe, to the antibiotic[33]. The addition of a fluorescein label to mutacin 1140 allows the in vivo visualization of this class of lantibiotic in action. These data have provided new insights into the importance of decarboxylation for bioactivity of the epidermin group of lantibiotics. Class I lantibiotics are known to bind to lipid II by forming a cage around the pyrophosphate residue using rings A and B (the lipid II binding domain)[37, 46]. Furthermore, the latter half of the peptide is believed to help in the lateral assembly of the lantibiotic-lipid II complexes to form islands[16, 47]. In nisin, these islands form a pore complex; however, the epidermin group primarily sequesters lipid II without forming a pore, as has been reported in fluorescently labeled lipid II vesicle experiments16, 48. Decarboxylation has been thought to be primarily important for stability of the peptide by preventing carboxypeptidases from degrading the lantibiotic[49]. The loss of activity in the mu1140-COOH analog is intriguing and is likely to be the result of various factors; however, the data provided herein suggest that the loss in activity is primarily attributed to loss in lateral assembly function. Microscopy studies show that mu1140-COOH can competitively bind to lipid II against nisin. Nisin and mutacin 1140 have been shown not to interact with each other, indicating that the decrease in fluorescence by the fluorescein labeled nisin analog was due to competition with the lipid II target[33]. Additionally, the mu1140-COOH analog was shown to have a protective function against wild-type mutacin 1140 and nisin. This suggests that the lateral assembly activity is crucial for bactericidal activity and the presence of the C-terminal carboxyl group prevents mutacin 1140 forming a stable lipid II complex.

The influence of dehydrations and lanthionine ring formations on lantibiotic biosynthesis is well known[50-51]. Yet, little is known on how other PTMs influence the biosynthesis of a functional lantibiotic. Studies have suggested that other PTM modifications, such as the N-terminal lactate of epilancin 15x, act independently of the decarboxylation must occur before terminal ring formation due to a reactive ene-thiol intermediate that promotes terminal ring formation[24]. A crystal structure of MrsD has suggested that its active site cannot accommodate a lanthionine ring[23]. Furthermore, attempts at decarboxylation of a lanthionine mimic proved futile[21]. The lack of in vitro decarboxylation of mu1140-COOH shows that decarboxylation must occur before ring D formation suggesting that MutD cannot accommodate the terminal lanthionine ring into its active site. Additionally, the isolation of the fully modified mu1140-COOH analog demonstrates that terminal ring formation can occur regardless of the presence of a carboxyl group.

During in vivo synthesis of mutacin 1140, mutations that prevent ring formation or dehydrations within the lantibiotic may affect other PTMs within the peptide[29]. A better understanding of the role of each PTM would promote the synthesis of novel analogs. The bioactivity of the mu1140-

COOH variant can be restored by capping the C-terminus with an amine (Table 7). The chemical synthesis of the AviCys residue is cumbersome[55-56]. However, chemical synthesis of this residue is not necessary for the epidermin group of lantibiotics and that solid phase peptide synthesis (SPPS) with differentially protected lanthionine can be used to synthesize this class of lantibiotics. Thus, the invention described herein provides new possibilities for synthesizing novel analogs of the epidermin group of lantibiotics. Furthermore, the importance of decarboxylation for bioactivity is demonstrated.

Example 5—Site Directed Mutagenesis of Mutacin 1140 and its Effect on Bactericidal Activity

*Streptococcus mutans* ATCC 55676 (wild-type) and the mutants that were at an $OD_{600}$ of 0.2 were spotted in triplicates on a pre-warmed THyex agar plate (150×15 mm) and allowed to dry. This assay was performed in this manner to ensure that each sample had the same colony size for comparing zones of inhibition. The plate was incubated for 24 hours then placed in an oven at 50° C. for thirty minutes to kill the bacteria before the indicator strain was overlaid. Heat killing the bacteria prevents any further antimicrobial compound production so that results seen are from single day incubation. Zone diameter was measured in millimeters across the plate and compared to wild-type (i.e. zone I for ATCC compared to zone I of Trp4Ala, etc.).

Figure 8:
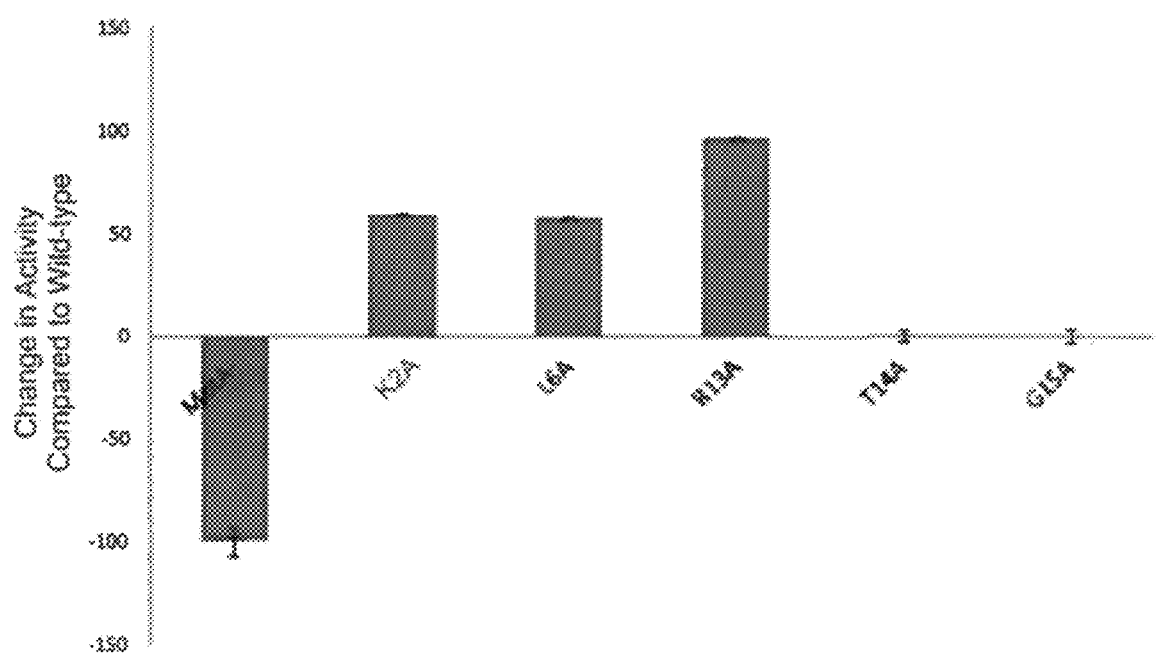
FIG. 8. Overlay assay comparing the zone of inhibitions for select mutations within the core peptide of mutacin 1140. The bioactivity is compared to the relative activity (zone of Inhibition) of the wild-type strain. The deletion strain of mutA is used as a negative control.
Figure 9:
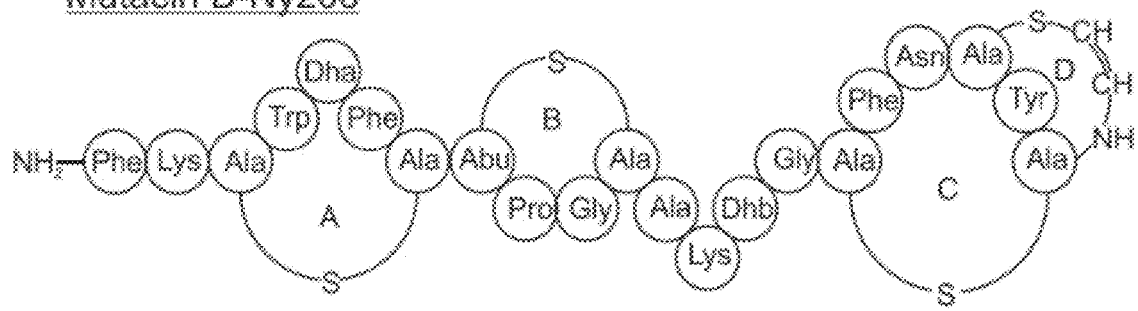
FIGS. 9-10. Mature forms of certain lantibiotics. Mutacin B-Ny266 (SEQ ID NO: 39); Mutacin 1140 (SEQ ID NO: 33); Microbisporicin (SEQ ID NO: 40); Mutacin I (SEQ ID NO: 41); Epidermin (SEQ ID NO: 34); Gallidermin (SEQ ID NO: 42); Mersacidin (SEQ ID NO: 43); Lichenicidin A2 (SEQ ID NO: 44); Lactocin S (SEQ ID NO: 45); Mutacin II (SEQ ID NO: 46); Epidermin (SEQ ID NO: 34); Gallidermin (SEQ ID NO: 42); Salivaricin (SEQ ID NO: 47); Lacticin 3147—A2 (SEQ ID NO: 48); Actagardine (SEQ ID NO: 49); Mersacidin (SEQ ID NO: 43); Mutacin B-hy266 (SEQ ID NO: 39); Mutacin 1140 (SEQ ID NO: 33); Ruminococcin A (SEQ ID NO: 50); and Microbisporicin (SEQ ID NO: 40).
Figure 9:
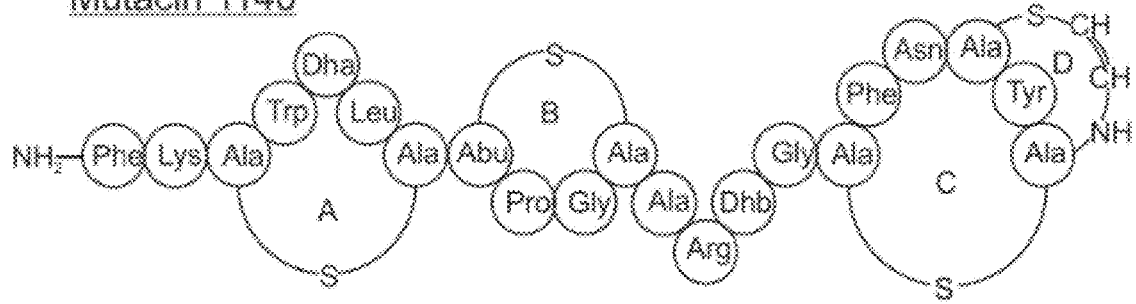
Figure 9:
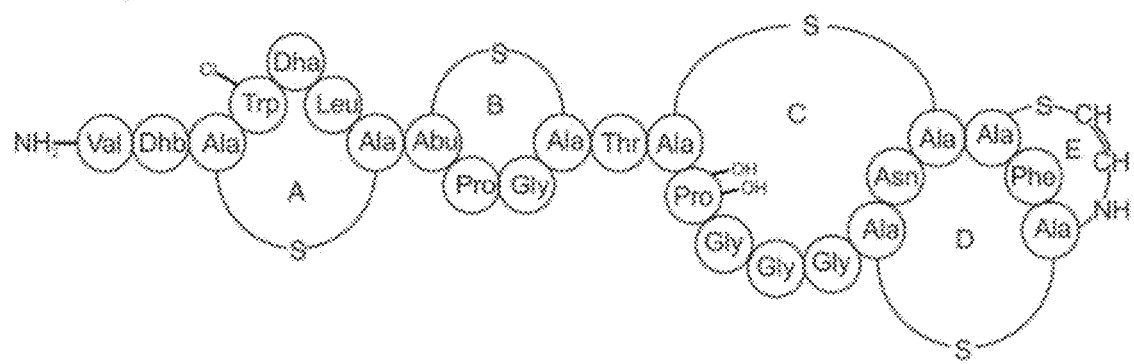
Figure 9:
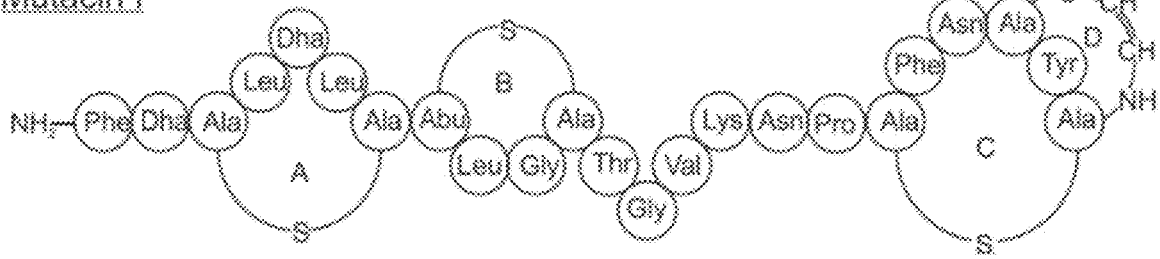
Figure 9:
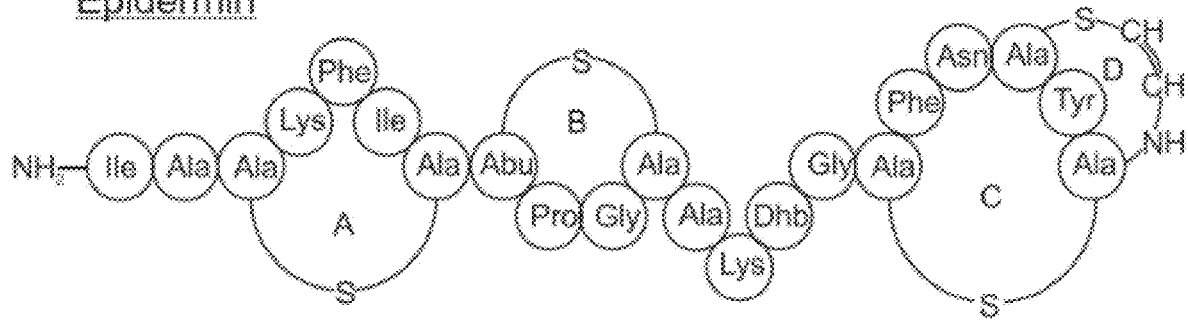
Figure 9:
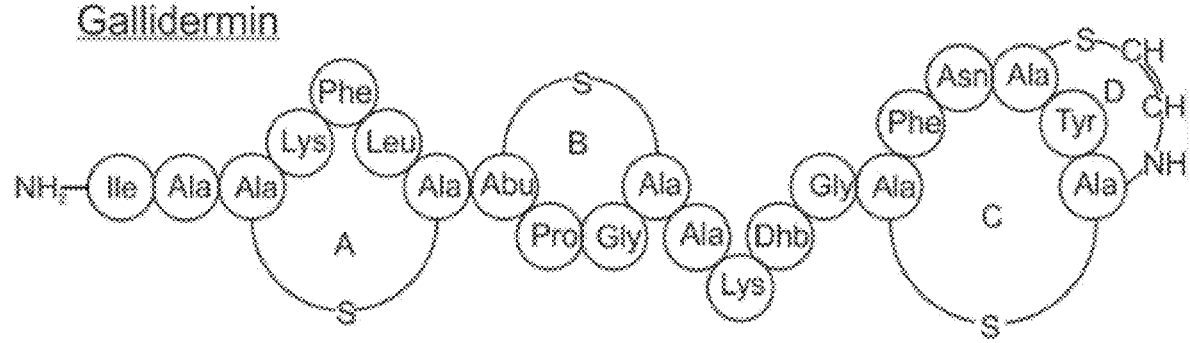
Figure 9:
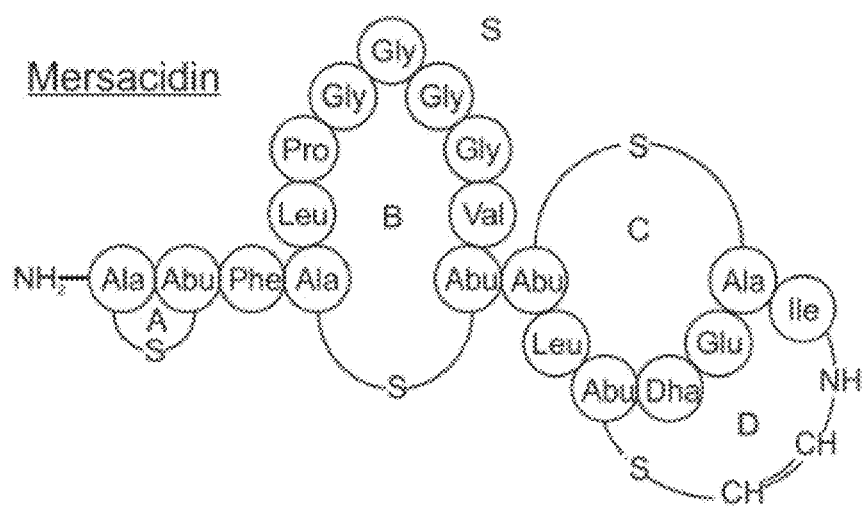
Figure 10:
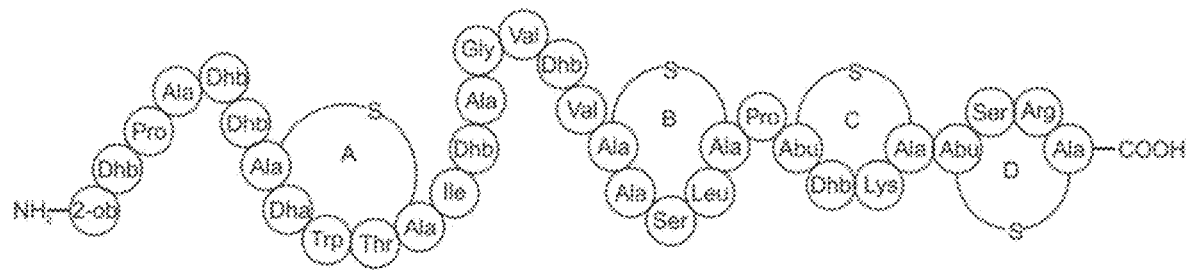
Figure 10:
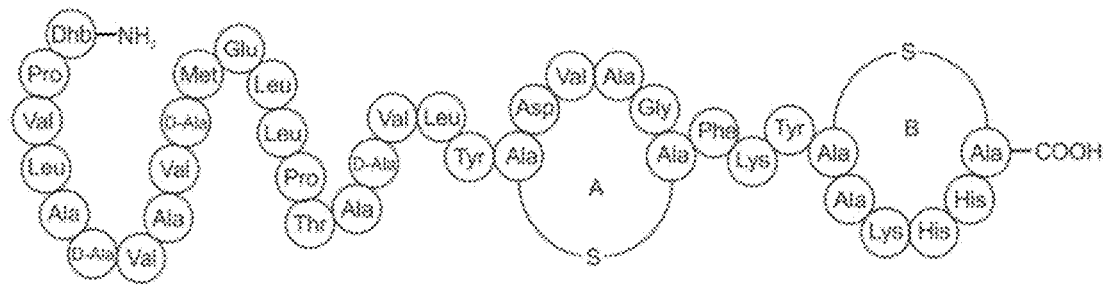
Figure 10:
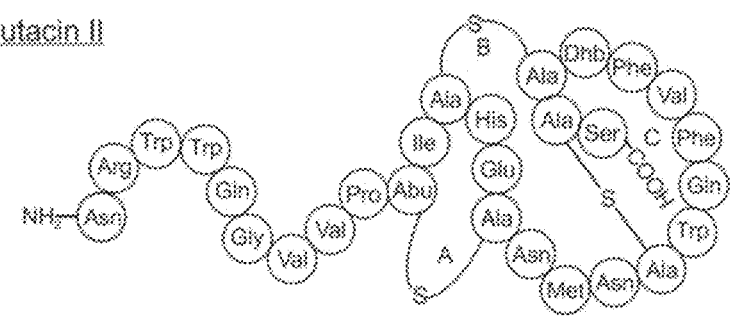
Figure 10:
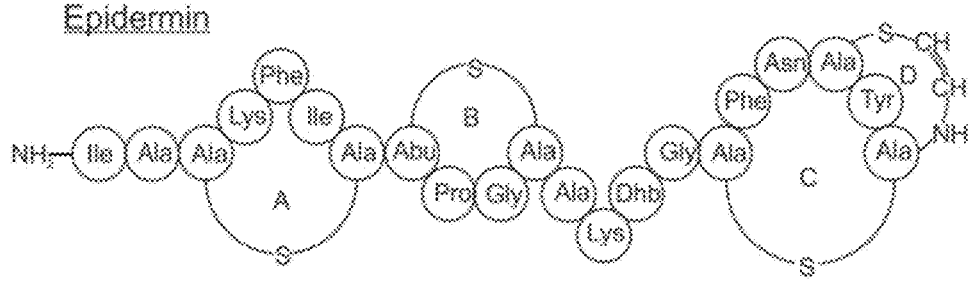
Figure 10:
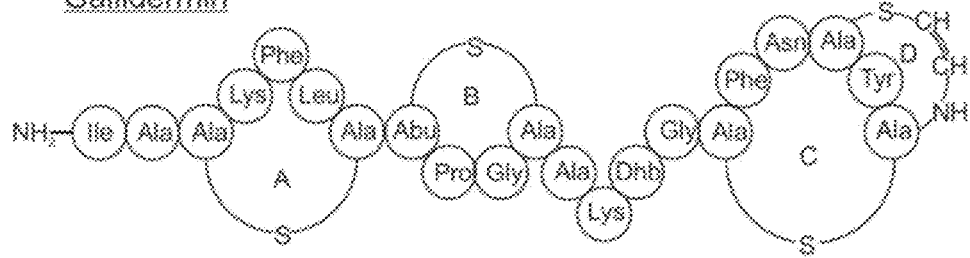
Figure 10:
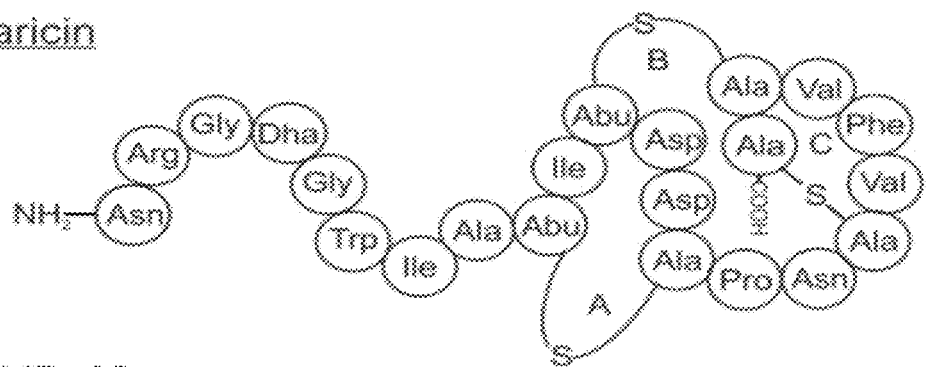
Figure 10:
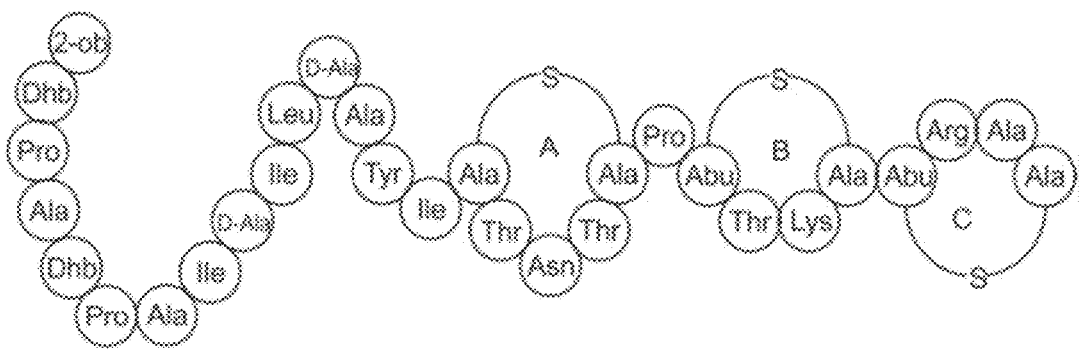
Figure 10:
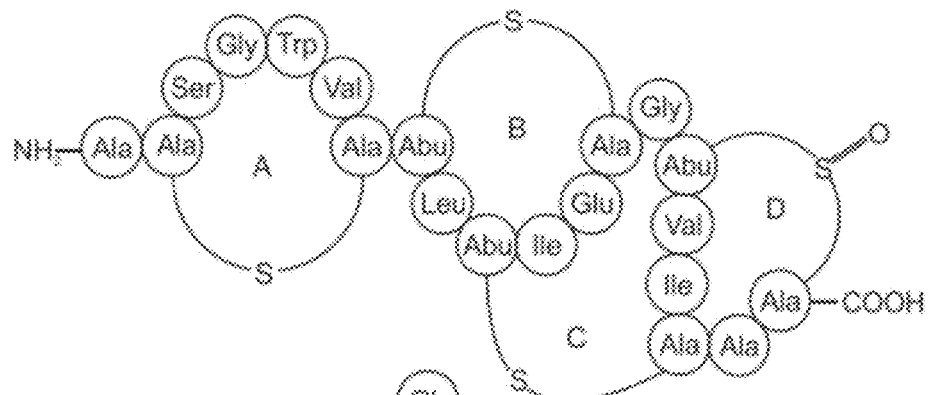
Figure 10:
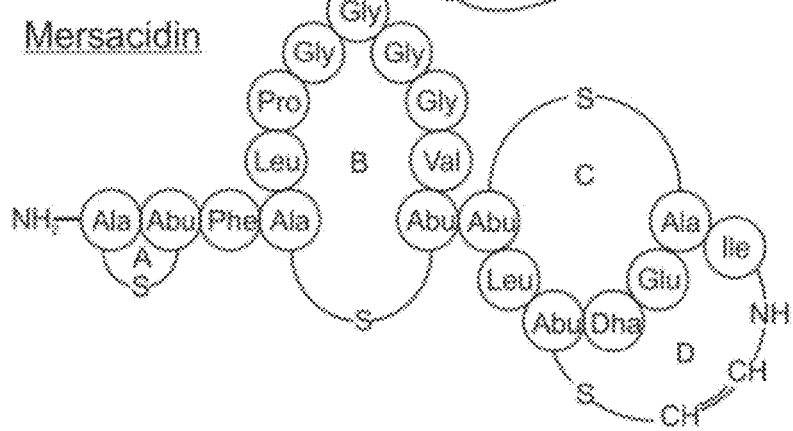
Figure 10:
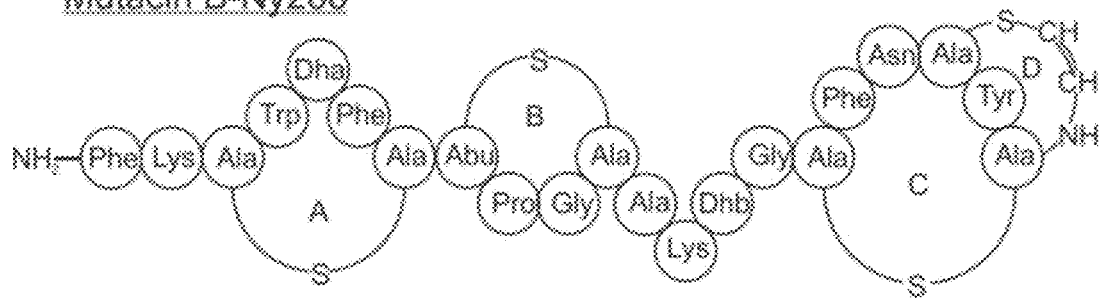
Figure 10:
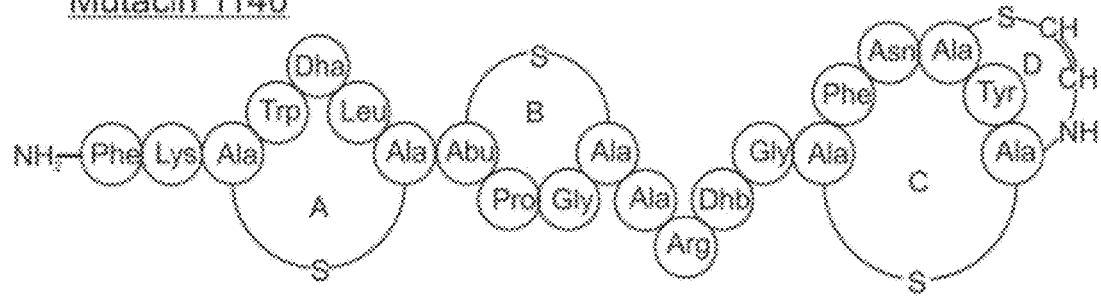
Figure 10:
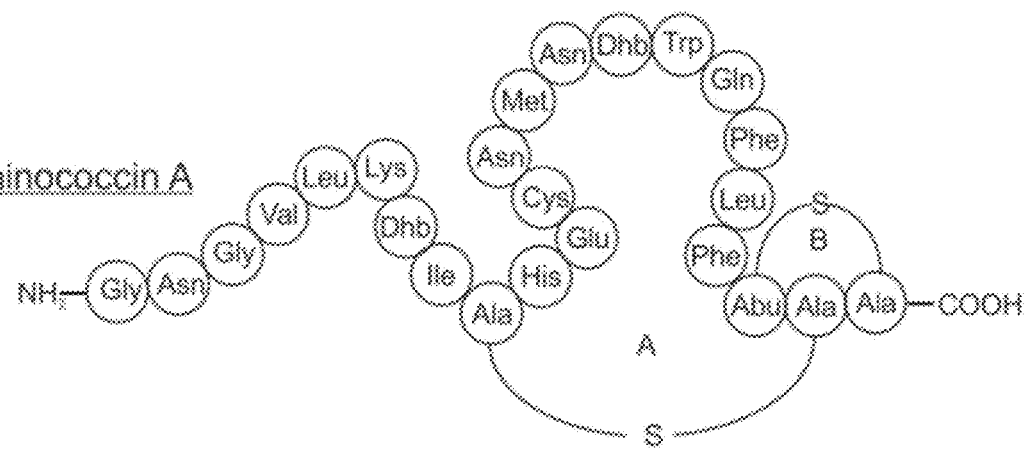
Figure 10:
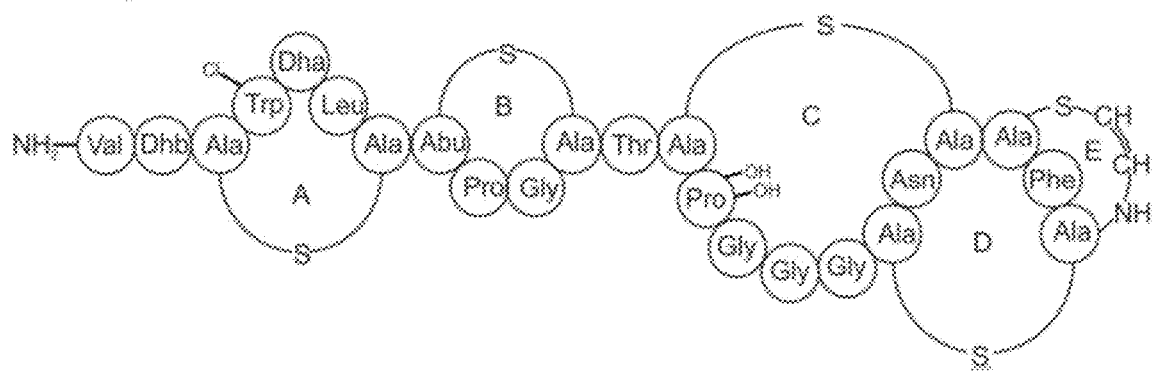

Lys2Ala, Leu6Ala, and Arg13Ala zones were statistically significantly from the wild-type mutacin 1140 producing strain (FIG. 8). These mutants led to a larger zone of inhibition and suggest that the bacterium is producing more of the product or the antibiotic is more active. The Thr(Dhb) 14Ala and Gly15Ala mutant had no change in activity relative to wild-type strain.

Mutacin 1140 variants Lys2Ala, Leu6Ala, and Arg13Ala were purified for comparing their bioactivity against wild-type mutacin 1140. Mutants Leu6Ala and Arg13Ala were two-fold more active against the indicator bacterium *Micrococcus lute us* (Table 10). These mutants prove to be beneficial in optimization of the antibacterial compound for the treatment of infectious diseases. These mutants also provide greater stability to the compound. For example, the Arg13Ala mutation makes the molecule less sensitive to gastric proteases.

The Lys2Ala mutant only had greater activity in the overlay assay, which suggests that this mutation leads to an increase in production of the compound. This mutant would be useful for using the bacterium or engineered bacterium as a probiotic.

TABLE 10

Minimum inhibitory activity of mutant mutacin 1140 against indicator strain *Micrococcus luteus*.

| Antibiotic | MIC (µg/ml) |
| --- | --- |
| Wild-type mutacin 1140 | 0.125 |
| Mutant Lys2Ala | 0.125 |
| Mutant Leu6Ala | 0.0625 |
| Mutant Arg13Ala | 0.0625 |

SEQ ID NO: 1
MKNSAAREAFKGANHPAGMVSEEELKALVGGNDVNPETTPATTSSWTCIT
AGVTVSASLCPTTKCTSRC

SEQ ID NO: 2
MKTEKKVLDELSLHASAKMGARDVESSMNADSTPVLASVAVSMELLPTAS
VLYSDVAGCFKYSAKHHC

SEQ ID NO: 3
MKNSKDILNNAIEEVSEKELMEVAGGKRGSGWIATITDDCPNSVFVCC

SEQ ID NO: 4
MNKLNSNAVVSLNEVSDSELDTILGGNRWWQGVVPTVSYECRMNSWQHVF
TCC

SEQ ID NO: 5
MKEKNMKKNDTIELQLGKYLEDDMIELAEGDESHGGTTPATPAISILSAY
ISTNTCPTTKCTRAC

SEQ ID NO: 6
MSALAIEKSWKDVDLRDGATSHPAGLGFGELTFEDLREDRTIYAASSGWV
CTLTIECGTVICAC

SEQ ID NO: 7
MSQEAIIRSWKDPFSRENSTQNPAGNPFSELKEAQMDKLVGAGDMEAACT
FTLPGGGGVCTLTSECIC

SEQ ID NO: 8
MEAVKEKNDLFNLDVKVNAKESNDSGAEPRIASKFICTPGCAKTGSFNSY
CC

SEQ ID NO: 9
MEAVKEKNELFDLDVKVNAKESNDSGAEPRIASKFLCTPGCAKTGSFNSY
CC

SEQ ID NO: 10
MSNTQLLEVLGTETFDVQENLFTFDTTDTIVAESNDDPDTRFKSWSFCTP
GCAKTGSFNSYCC

SEQ ID NO: 11
MSNTQLLEVLGTETFDVQEDLFAFDTTDTTIVASNDDPDTRFKSWSLCTP
GCARTGSFNSYCC

SEQ ID NO: 12
MRNDVLTLTNPMEEKELEQILGGGNGVLKTISHECNMNTWQFLFTCC

SEQ ID NO: 13
MPADILETRTSETEDLLDLDLSIGVEEITAGPAVTSWSLCTPGCTSPGGG
SNCSFCC

SEQ ID NO: 14
TTPATTSSWTCITAGVTVSASLCPTTKCTSRC

SEQ ID NO: 15
STPVLASVAVSMELLPTASVLYSDVAGCFKYSAKHHC

SEQ ID NO: 16
KRGSGWIATITDDCPNSVFVCC

SEQ ID NO: 17
NRWWQGVVPTVSYECRMNSWQHVFTCC

SEQ ID NO: 18
TTPATPAISILSAYISTNTCPTTKCTRAC

SEQ ID NO: 19
SSGWVCTLTIECGTVICAC

SEQ ID NO: 20
CTFTLPGGGGVCTLTSECIC

```
                                  SEQ ID NO: 21
IASKFICTPGCAKTGSFNSYCC

SEQ ID NO: 22
IASKFLCTPGCAKTGSFNSYCC

SEQ ID NO: 23
FKSWSFCTPGCAKTGSFNSYCC

SEQ ID NO: 24
FKSWSLCTPGCARTGSFNSYCC

SEQ ID NO: 25
GNGVLKTISHECNMNTWQFLFTCC

SEQ ID NO: 26
VTSWSLCTPGCTSPGGGSNCSFCC
```

Example 6—Core Peptide Mutants of Mutacin 1140 and its Effect on Bactericidal Activity Mutacin 1140 has demonstrated activity against several resistant strains of S. pneumoniae. Core peptide mutants of mutacin 1140 that have improved stability, superior pharmacokinetics, and higher activity against S. pneumoniae are provided. Particularly, core peptide mutant R13A of mutacin 1140 is provided as an alternative treatment option for an S. pneumoniae infection.

The formulations of the core peptide mutants, particularly, formulations suitable for intravenous administration, are also disclosed. Such formulations have improved toxicity profile and ability to treat an S. pneumoniae infection. Toxicological and pharmacokinetic evaluation of R13A core mutant of mutacin 1140 following intravenous route of administration are described. R13A core mutant of mutacin 1140 effectively treats a respiratory infection and bacteremia caused by S. pneumoniae.

The disruption of normal upper respiratory flora caused as a result of conventional antibiotic treatment is the basis for the rampant spread of S. pneumoniae. Conjugate vaccines protect against select serotypes, but the niches occupied by these are being filled by one of the other 92 serotypes of S. pneumoniae. The use of broad spectrum antibiotics actually increases the spread of antibiotic resistant S. pneumoniae infections in hospitals. Furthermore, the overuse of conventional antibiotics has led to an emergence of resistant organisms by creating reservoirs of resistant bacteria within the nasal passages that confer the resistance to S. pneumoniae. There are more than 4 million S. pneumoniae infections each year. Pneumococcal ear infections (otitis media) make up 1.5 million of these cases, and they are a direct result of conventional antibiotic use (CDC, Antibiotic Resistance Report 2013). At least 400,000 hospitalizations are estimated from pneumococcal pneumonia each year in the United States (CDC). Approximately thirty percent of S. pneumoniae infections are resistant to one or more antibiotics. These infections lead to excessive hospital stays and death. Patients with pneumococcal pneumonia have a high incidence of bacteremia (~30%) leading to death in about 6% of the cases. Despite the positive outcome of the conjugate vaccine, a need exists for developing alternative approaches to lessen the burden associated with pneumococcal pneumonia. The increasing tolerance of pneumococcal infections to penicillin and vancomycin is alarming. Certain embodiments of the invention provide new antibiotics with potent activity against S. pneumoniae that can be added to the dwindling arsenal of treatment options.

Mutacin is a peptide belonging to class I lantibiotics and is naturally produced by a strain of the common oral bacterium, Streptococcus mutans. This compound has demonstrated activity against several Gram-positive pathogens, including oxacillin- and vancomycin-resistant Staphylococcus aureus and vancomycin-resistant E. faecalis. The post-translational incorporation of lanthionine rings confers proteolytic stability, which should enhance its stability and use in animals. However, mutacin 1140 like other lantibiotics has a short half-life in animals. The invention provides core peptide mutants of mutacin 1140 that have potent activity against S. pneumoniae and have the pharmacokinetic and pharmacodynamic parameters supporting its potential usefulness in treating a pneumococcal infection in animals.

Mode of action of mutacin: Sequential subculturing of S. aureus and S. pneumoniae in sub-inhibitory concentrations of mutacin resulted in only a three-fold increase in the minimum inhibitory concentration, suggesting that this antibiotic is a good candidate as a therapeutic agent against infection. Mutacin functions, much like vancomycin, by binding to lipid II, which is essential for cell-wall formation. Although vancomycin shares the same target, it uses a different mechanism to inhibit cell wall synthesis. Vancomycin binds to a different region on lipid II, which are the terminal D-Ala-D-Ala residues of the peptide. This difference in activity possibly contributes to mutacin's impressive ability to kill vancomycin-resistant strains of bacteria. Mutacin kills bacteria by sequestering the essential cell wall biosynthetic molecule lipid II into domains away from the sites that are required for cell wall synthesis. Lipid II is essential for the transport of cell wall subunits across the bacterial cytoplasmic membrane. This highly dynamic molecule is present in all eubacteria in relatively small amounts. Lipid II is assembled on the cytoplasmic side of the bacterial membrane and carries one complete peptidoglycan subunit (GlcNAc-MurNAc-pentapeptide) across the plasma membrane. A novel lipid II-binding motif for mutacin-related lantibiotics has been characterized by NMR, in which the N-terminal portion of the lantibiotic, lanthionine rings A and B, interact with the pyrophosphate, peptidoglycan MurNAc, and first isoprene of lipid II. Mutacin activity is also attributed to bacterial membrane disruption. No protein receptor is required for the bactericidal activity of this class of antibiotics, and therefore, it cannot easily be overcome via genetic adaptation. This unique mechanism of action for mutacin and similar lantibiotics support the long-term value of a new antibiotic.

Therapeutic activity of mutacin: The solubility of pure native mutacin in aqueous saline solution exceeds 0.5 mg/mL, which is well above its low inhibitory concentration against Gram-positive bacteria. Mutacin has a broad spectrum of activity against Gram-positive bacteria. In particular, mutacin has a submicromolar activity against S. pneumoniae. Furthermore, mutacin has been shown to be active against oxacillin- and vancomycin-resistant S. aureus, as well as vancomycin-resistant E. faecalis. No activity was observed against Gram-negative bacteria or yeast consistent with previous lantibiotic studies. The level of activity varied by more than 128-fold between species of Gram-positive bacteria, which may promote its use for treating S. pneumoniae infections. Disease associated with S. pneumoniae is usually attributed to the disruption of host flora. The lack of activity against Gram-negative bacteria and the increased susceptibility of pneumococcal bacteria relative to other Gram-positive bacteria may promote the reestablishment of the host's protective flora during treatment. Results of acute toxicity studies in rodents support the further development of analogs of mutacin for the treatment of Gram-positive infections. Mouse and rat models were tested by bolus intravenous injection of mutacin in normal saline. Both models readily tolerated doses up to 25 mg/kg body weight. Time-kill studies have been performed by using strains of medically important Gram-positive species, S. aureus and E. faecalis. The results of time-kill investigations showed that mutacin exhibited a rapid initial killing against multidrug resistant S. aureus, whereas bacteriostatic activity was observed against a vancomycin resistant strain of E. faecalis. This is very similar to the activity seen with vancomycin. However, the native mutacin 1140 has a short half-life and is rapidly cleared from the blood, which prevents its use and development as an effective treatment option.

Several mutacin core peptide mutants were tested for their ability to inhibit several clinical strains of S. pneumoniae, while also having superior pharmacokinetic and stability properties. The pharmacokinetics and efficacy of certain mutacin core peptide mutants were tested to provide treatment options for an S. pneumoniae infection.

Example 7—Formulation, Toxicological, and Pharmacokinetic Evaluation of the R13A Core Peptide Mutant of Mutacin 1140 Following Intravenous Administration R13A core peptide mutant of mutacin 1140 was tested as a novel therapeutic for pneumococcal infections. As described above, native mutacin has several attributes to serve as a successful therapeutic agent, but its low peak plasma concentration and rapid clearance from blood prevents its development as an effective therapy. Core peptide mutants of mutacin 1140 that have superior properties compared to native mutacin are provided. Also, formulations of R13A that improves pharmacokinetic properties of R13A are also provided.

Figure 11:
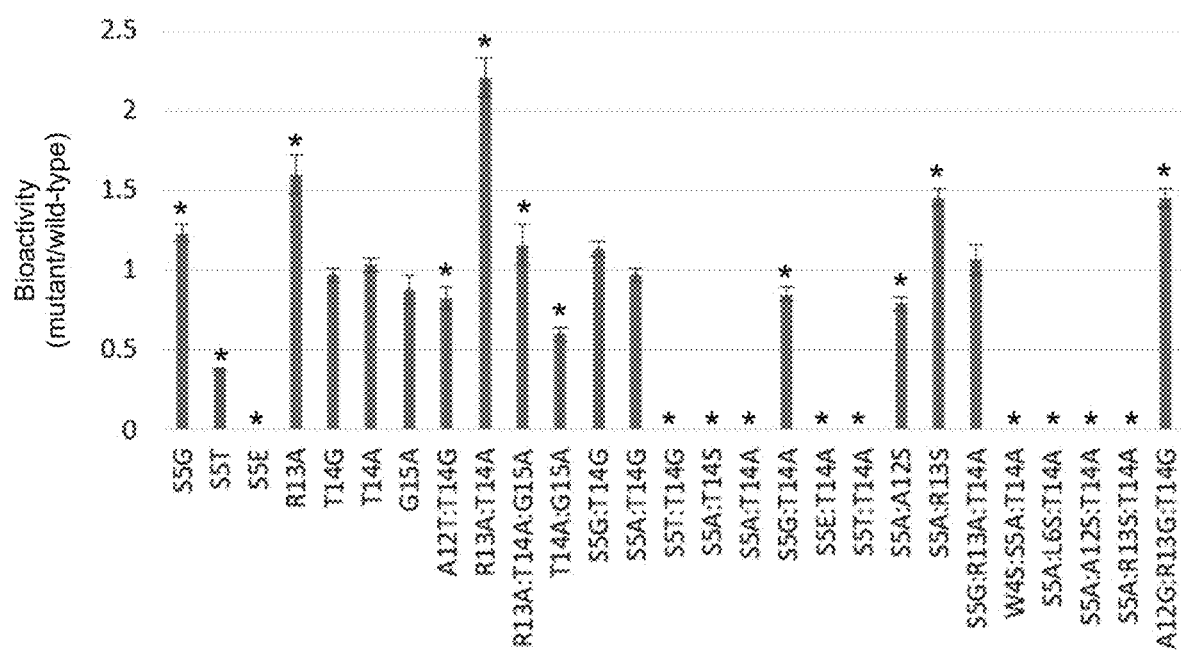
FIG. 11. Bioactivity of core peptide mutants compared to wild-type *S. mutans*. The bioactivity is represented as the ratio of the zone of inhibition of mutant to wild-type strain. * denotes statistical significance.

FIG. 11 illustrates the bioactivity of various core peptide mutants of mutacin 1130. The activity of the core mutant peptides is expressed as a ratio of the area of the zone of inhibition of each mutant strain to the area of the zone of inhibition of the wild-type strain against indicator strain of *Micrococcus luteus*. A value of one denotes similar activity to wild-type, but values greater than one shows higher activity for the mutants. The deferred antagonism assay is an overlay assay of the indicator strain onto plates containing heat killed colonies of the mutacin producer strain after growing overnight. Core peptide mutants having inhibitory activity were isolated and the purified products were further evaluated by a standard minimum inhibitory concentration (MIC) assay. MICs for some of the core peptide mutants of mutacin 1140 are provided in Table 11.

TABLE 11

Bioactivity of core peptide mutants of mutacin 1140. *C. accolens* KPL 1818 and *C. accolens* ATCC 49725 were cultured in THyex broth supplemented with 1% Tween 80 to promote the bacterial growth. MICs of wild-type mutacin 1140 were done against *M. luteus*, *S. aureus*, and *S. pneumoniae* with or without 1% Tween 80 at the same time and there was no difference in activities. MICs and MCLs are presented in micrograms per milliliter.

| Mutacin 1140 Analogs | *M. luteus* ATCC 10240 | | *S. aureus* ATCC 25923 | | *C. accolens* ATCC 49725 | | *C. accolens* KPL 1818 | | *S. pneumonia* ATCC 27336 | |
|---|---|---|---|---|---|---|---|---|---|---|
| | MIC | MLC | MIC | MLC | MIC | MLC | MIC | MLC | MIC | MLC |
| Wild-Type Mutacin | 0.0625 | 0.0625 | 8 | 8 | 0.125 | 0.125 | 1 | 2 | 0.5 | 0.5 |
| Mutations within ring A | | | | | | | | | | |
| S5T | 4 | 4 | >32 | >32 | >4 | >4 | >4 | >4 | 2 | 2 |
| S5G | 0.125 | 0.125 | 8 | 8 | 0.5 | 0.5 | 0.5 | 0.5 | 0.0078 | 0.0078 |
| Mutations within hinge region | | | | | | | | | | |
| R13A | 0.0625 | 0.0625 | 16 | 16 | 0.25 | 0.5 | 1 | 1 | 0.125 | 0.125 |
| T14G | 0.0625 | 0.0625 | >32 | >32 | 0.0625 | 0.0625 | 0.25 | 0.5 | 0.5 | 0.5 |
| T14A | 0.125 | 0.125 | 8 | 16 | 0.25 | 0.25 | 0.5 | 2 | 0.5 | 0.5 |
| G15A* | 0.125 | 0.125 | 16 | 16 | 1 | 1 | 1 | 2 | 0.5 | 0.5 |
| R13A: T14A | 0.25 | 0.5 | 32 | 32 | 0.5 | 0.5 | 0.5 | 0.5 | 2 | 2 |
| A12T: T14G | 0.25 | 0.25 | >32 | >32 | 0.125 | 0.25 | 0.5 | 1 | 2 | 2 |
| Mutations within both ring A and hinge region | | | | | | | | | | |
| S5G: T14A | 0.125 | 0.125 | >32 | >32 | 4 | 4 | — | — | 4 | 4 |
| S5A: T14G | 0.0625 | 0.125 | 32 | 32 | 0.25 | 0.25 | 0.5 | 1 | 0.25 | 0.25 |
| S5G: T14G | 0.5 | 0.5 | 8 | 16 | 1 | 1 | 0.5 | 1 | 2 | 2 |
| S5A: A12S dehydrated | 0.125 | 0.25 | 16 | 32 | 0.25 | 0.25 | 0.5 | 1 | 0.125 | 0.125 |
| S5A: A12S un-dehydrated | 0.125 | 0.25 | 16 | 16 | — | — | — | — | 0.125 | 0.125 |

TABLE 11-continued

Bioactivity of core peptide mutants of mutacin 1140. *C. accolens* KPL 1818 and *C. accolens* ATCC 49725 were cultured in THyex broth supplemented with 1% Tween 80 to promote the bacterial growth. MICs of wild-type mutacin 1140 were done against *M. luteus*, *S. aureus*, and *S. pneumoniae* with or without 1% Tween 80 at the same time and there was no difference in activities. MICs and MCLs are presented in micrograms per milliliter.

| Mutacin 1140 Analogs | *M. luteus* ATCC 10240 | | *S. aureus* ATCC 25923 | | *C. accolens* ATCC 49725 | | *C. accolens* KPL 1818 | | *S. pneumonia* ATCC 27336 | |
|---|---|---|---|---|---|---|---|---|---|---|
| | MIC | MLC | MIC | MLC | MIC | MLC | MIC | MLC | MIC | MLC |
| S5A: R13S | 0.125 | 0.25 | >32 | >32 | 2 | 2 | 2 | 4 | 0.5 | 0.5 |
| S5G: R13A: T14A | 2 | 16 | >32 | >32 | >4 | >4 | >4 | >4 | 8 | >16 |

Figure 13:
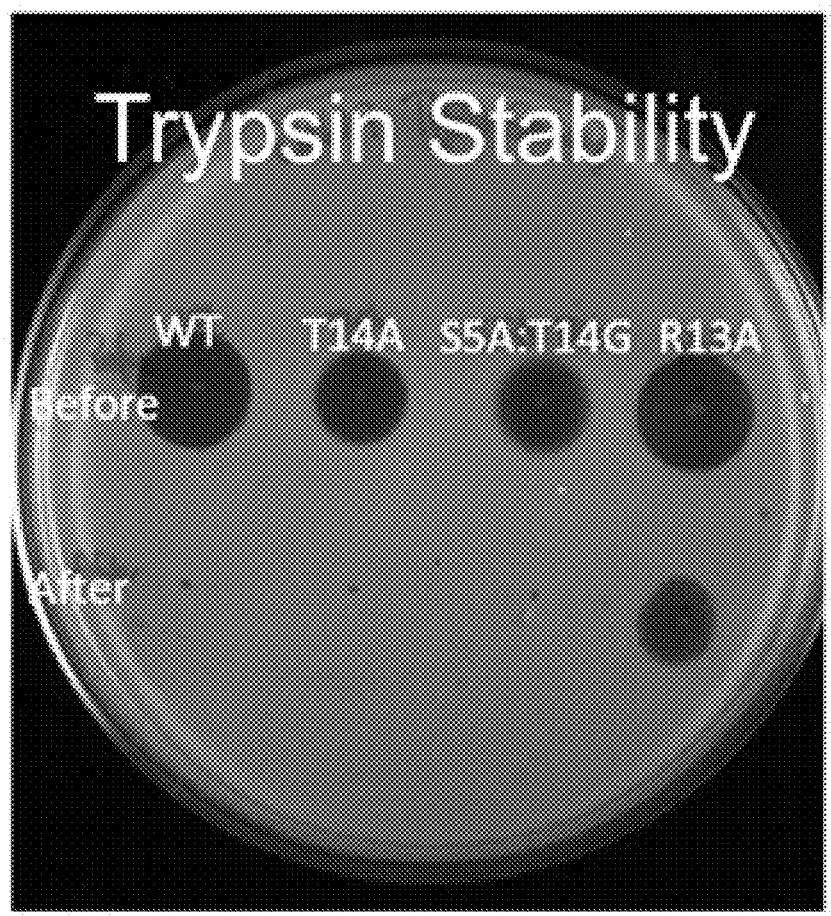
FIG. 13. Typsin stability of mutacin 1140 core peptide mutants. WT denotes wild-type mutacin 1140. Overlay assay was done using *M. luteus* as an indicator strain.

Selective activity and stability of analogs: Several core peptide mutants are provided that have improved activity against our ATCC strain of *S. pneumoniae*. These core peptide mutants were also selected based on the absence of a dehydrated residue Dha/Dhb or the proteolytically susceptible arginine residue. While the S5G, S5A:T14G, S5A, T14A, and T14G had low micromolar activity against one or more of the clinical *S. pneumoniae* isolates, the R13A analog had superior activity against most strains compared to wild-type mutacin (Table 12). Although the analog S5G had improved activity against *S. pneumoniae* ATCC 27336 compared to native mutacin and R13A, the S5G had less activity against all other tested strains of *S. pneumoniae*. Further supporting data for the development of the R13A analog are: 1) the activity of R13A was unchanged when tested in the presence of 50% serum, 2) In a trypsin stability screen (native mutacin and the analogs were spotted on a THyex plate overlayed with *M. luteus* before and after treatment with 0.5 mg/mL of trypsin at 37° C. for 30 minutes), R13A has improved stability compared to native mutacin, T14A, and S5A:T14G (FIG. 13) The solubility of the R13A analog in saline is greater than 2 mg/mL, which is a four-fold increase in solubility of native mutacin. 4) The R13A mutation prevents feedback inhibition of mutacin 1140 production, leading to a 100% increase in yield from the culture liquor. The improved stability of R13A in the presence of trypsin protease is encouraging when compared to native mutacin, since trypsin-like proteases are abundantly present in the blood. They are important for immunoregulation and blood coagulation. The observed increase in stability of the R13A analog will likely be advantageous in an animal model.

Pharmacokinetic comparison of native mutacin and analogs: Murine models of *S. pneumoniae* infection are easy to use and commonly employed to study efficacy of antibiotic treatments. Murine models of *S. pneumoniae* infection provide an easy and reliable platform to test the efficacy of candidate drugs for treatment. The efficacy of the novel formulation of R13A was evaluated in a mouse model of pneumococcal pneumonia.

Figure 12A:
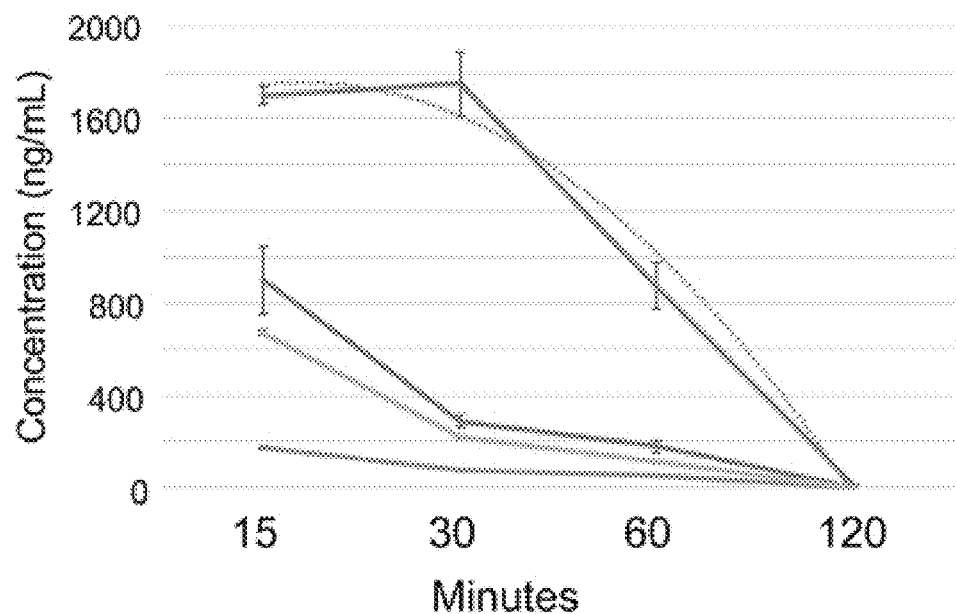
FIGS. 12A-12B. Pharmacokinetic and pharmacodynamic analysis of mutacin 1140 and mutacin 1140 core peptide mutants. A. Plasma concentrations of native mutacin 1140 (blue), R13A (orange), S5G (yellow), and S5A:T14G (grey) following an intravenous administration of a 2.5 mg/Kg dose. B. Kill kinetics of wild-type mutacin 1140 (blue; at 0.5 µg/ml) and R13A (orange; at 0.125 µg/ml) against *S. pneumoniae* ATCC 27336.
Figure 12B:
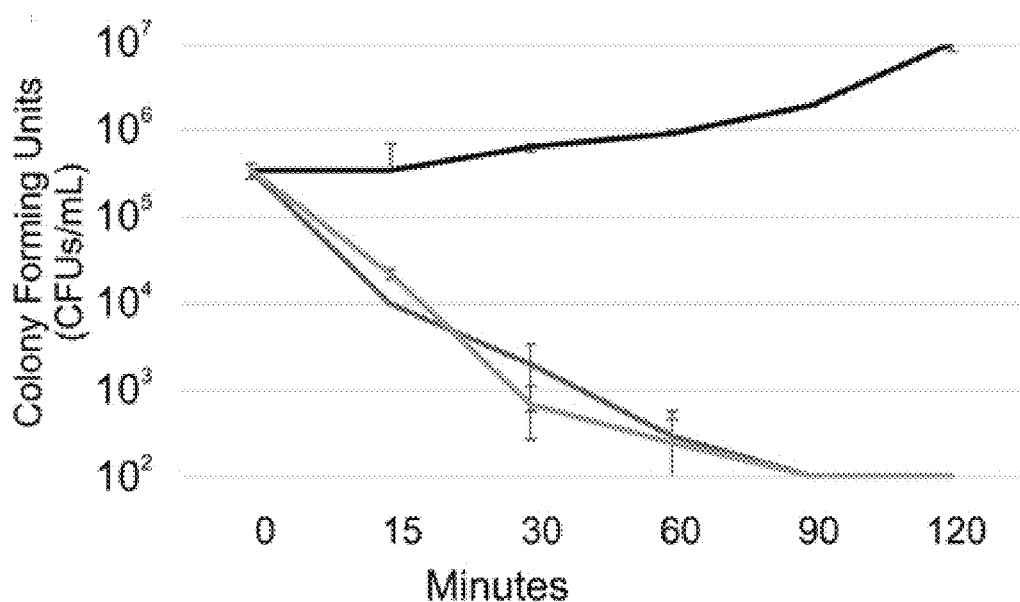

The compounds were dissolved in normal saline for all pharmacokinetic studies. An extraction protocol was developed in vitro by the addition of each compound to commercially bought BALB/c mouse serum. The compounds were extracted by the addition of 70% ACN containing 0.1% TFA/30% methanol containing 0.4% formic acid. The extract was then analyzed by LC-MS using a TSQ Vantage Triple Quad mass spectrometer. A standard curve was generated for each compound using known dilutions of the compounds in serum, which was then extracted. The R-squared values for each standard exceeded 0.98. BALB/c mice were used to evaluate pharmacokinetics of the compounds in vivo. A 2.5 mg/kg i. v. dose was evaluated for native mutacin, R13A, S5G, and double mutant S5A:T14G (FIG. 12A). A polynomial second order was used to estimate the peak plasma concentration and half-life of the R13A. The peak plasma concentration of R13A was 1700 ng/mL and the estimated half-life was 70 minutes. At 70 minutes, native mutacin and other mutant analogs were about to be cleared from the blood. Interestingly, the double mutant S5A:T14G performed the worst. This data in combination with the S5G data, suggests that the Dhb residue normally at position 14 is important for peptide stability. Possibly, the Dhb14 residue may protect the peptide from trypsin-like proteases in the blood. As seen in the in vitro studies, at 125 ng/mL, the R13A analog reduces the number of *S. pneumo-nia* by 2-logs (FIG. 12B). Thus, taking the dynamics of cell death into account and the pharmacokinetics of the R13A,

TABLE 12

MICs of mutacin analogs against clinical *S. pneumoniae* isolates. *S. pneumoniae* isolates required the addition of 50% blood for growth in the bioassay. MICs and MLCs are presented in micrograms per milliliter.

| | *S. pneumoniae* AI8 | *S. pneumoniae* AI11 | *S. pneumoniae* AI14 | *S. pneumoniae* AI16 | *S. pneumoniae* AI17 |
|---|---|---|---|---|---|
| Mutacin 1140 | 1 | 1 | 0.125 | 1 | 0.25 |
| R13A | 0.5 | 0.5 | 0.25 | 0.5 | 0.25 |
| S5G | >8 | 8 | >8 | >8 | 2 |
| S5A:T14G | >8 | >8 | >8 | >8 | 8 |
| S5A | 8 | 4 | >8 | 4 | 4 |
| T14A | 8 | 4 | 2 | 8 | 8 |
| T14G | 8 | 2 | 1 | 8 | 8 | the R13A in serum is above the inhibitory concentration for *S. pneumonia* long enough to kill the pathogen. R13A is more stable and more active against *S. pneumoniae* strains and is pharmacokinetically superior to native mutacin.

Example 8—Formulations of Antimicrobial Peptides

Antimicrobial peptides can have poor solubility. Solubilizing/surfactant agents are used to meet the strict USP requirements for purity and clarity of injectable formulations. R13A is soluble at 2 mg/ml in saline solution. To further improve the solubility, solubilizing agents can be used. The solid stock of R13A can be prepared by lyophilization, stored at 4° C., and reconstituted as needed. In certain embodiments, the formulation comprises 50 mg of R13A, 50 mg of fructose (stabilizer), 269 mg of mannitol (bulking agent), 125 mg of polysorbate-80 (solubilizing agent), and 6 mg of tartaric acid (buffer). 50 mg of solid stock can be reconstituted in 1-2 mL of water as needed (a 16-8 mg/mL of active agent stock). In further embodiments, the formulations of R13A further comprise excipients such as β-cyclodextrins, Tween 20, PEG 400, demethylacetamide. Such formulations can contain up to 8 mg/mL R13A. Also, 5-20% ethanol can be used to reconstitute the solid stock.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Guillemot D, Varon E, Bernède C, Weber P, Henriet L, Simon S, Laurent C, Lecoeur H, Carbon C. 2005. Reduction of antibiotic use in the community reduces the rate of colonization with penicillin G-nonsusceptible *Streptococcus pneumoniae*. Clin Infect Diseases 41:930-938.
2. Allgaier, H.; Jung, G.; Werner, R. G.; Schneider, U.; Zahner, H. Angew. Chem.-Int. Edit. Engl. 1985, 24, 1051-1053.
3. Bierbaum G, Sahl H G. 2009. Lantibiotics: mode of action, biosynthesis and bioengineering. Curr Pharm Biotechnol 10:2-18.
4. Bierbaum, G.; Sahl, H. G. Curr. Pharm. Biotechnol. 2009, 10, 2-18.
5. Birri, D. J., D. A. Brede, and I. F. Nes, Salivaricin D, a novel intrinsically trypsin-resistant lantibiotic from *Streptococcus salivarius* 5M6c isolated from a healthy infant. Applied And Environmental Microbiology, 2012. 78(2): p. 402-410.
6. Blaesse, M.; Kupke, T.; Huber, R.; Steinbacher, S. 2003, 59, 1414-1421.
7. Blaesse, M.; Kupke, T.; Huber, R.; Steinbacher, S. Embo J. 2000, 19, 6299-6310.
8. Boakes, S.; Cortes, J.; Appleyard, A. N.; Rudd, B. A. M.; Dawson, M. J. Mol. Microbiol. 2009, 72, 1126-1136.
9. Bomar, L., et al., *Corynebacterium* accolens Releases Antipneumococcal Free Fatty Acids from Human Nostril and Skin Surface Triacylglycerols. Mbio, 2016. 7(1): p. e01725-e01715.
10. Bonelli, R. R.; Schneider, T.; Sahl, H. G.; Wiedemann, I. Antimicrob Agents Chemother 2006, 50, 1449-57.
11. Breukink, E.; Wiedemann, I.; van Kraaij, C.; Kuipers, O. P.; Sahl, H. G.; de Kruijff, B., Use of the cell wall precursor lipid II by a pore-forming peptide antibiotic. Science 1999, 286, 2361-2364.
12. Carrillo, A. K.; VanNieuwenhze, M. S. Org. Lett. 2012, 14, 1034-1037.
13. Chatterjee C, Paul M, Xie L, van der Donk W A. 2005. Biosynthesis and mode of action of lantibiotics. Chem Rev 105:633-684.
14. Chen S, Wilson-Stanford S, Cromwell W, Hillman J D, Guerrero A, Allen C A, Sorg J A, Smith L. 2013. Site-directed mutations in the lanthipeptide mutacin 1140. Appl Environ Microbiol 79:4015-4023.
15. Chiavolini, D., G. Pozzi, and S. Ricci, Animal Models of *Streptococcus pneumoniae* Disease. Clinical Microbiology Reviews, 2008. 21(4): p. 666-685.
16. Claesen, J.; Bibb, M. Proc. Natl. Acad. Sci. U.S.A. 2010, 107, 16297-16302.
17. Craik, D. J.; Fairlie, D. P.; Liras, S.; Price, D. Chem. Biol. Drug Des. 2013, 81, 136-147.
18. Crowther, G. S.; Baines, S. D.; Todhunter, S. L.; Freeman, J.; Chilton, C. H.; Wilcox, M. H. J. Antimicrob. Chemother. 2013, 68, 168-176.
19. Dischinger, J.; Chipalu, S. B.; Bierbaum, G. Int. J. Med. Microbiol. 2014, 304, 51-62.
20. Eaton, D. L. and C. D. Klaassen, Principles of Toxicology. Casarett and Doull's Toxicology, ed. C. D. In: Klaassen. 1996: McGraw-Hill, New York.
21. Escano J, Smith L. 2015. Multipronged approach for engineering novel peptide analogues of existing lantibiotics. Expert Opin Drug Discov. 10:857-70.
22. Escano J, Stauffer B, Brennan J, Bullock M, Smith L. 2014. The leader peptide of mutacin 1140 has distinct structural components compared to related class I lantibiotics. Microbiol Open 3:961-972.
23. Escano J, Stauffer B, Brennan J, Bullock M, Smith L. 2015. Biosynthesis and transport of the lantibiotic mutacin 1140 produced by *Streptococcus mutans*. J Bacteriology 197:1173-1184.
24. Escano, J. and L. Smith, Multipronged approach for engineering novel peptide analogues of existing lantibiotics. Expert Opinion On Drug Discovery, 2015. Posted online on May 23, 2015.
25. Escano, J., et al., Biosynthesis and transport of the lantibiotic mutacin 1140 produced by *Streptococcus mutans*. Journal Of Bacteriology, 2015. 197(7): p. 1173-1184.
26. Foulston, L. C.; Bibb, M. J. Proc. Natl. Acad. Sci. U.S.A. 2010, 107, 13461-13466.
27. Foulston, L.; Bibb, M., Feed-Forward Regulation of Microbisporicin Biosynthesis in Microbispora corallina. J. Bacteriol. 2011, 193, 3064-3071.
28. Garcia-Reynaga, P.; Carrillo, A. K.; VanNieuwenhze, M. S. Org. Lett. 2012, 14, 1030-1033.
29. Ghobrial O, Derendorf H, Hillman J D. 2010. Human serum binding and its effect on the pharmacodynamics of the lantibiotic MU1140. Europ J Pharma Sci 41:658-664.
30. Ghobrial O, Derendorf H, Hillman J D. 2010. Pharmacokinetic and pharmacodynamic evaluation of the lantibiotic MU1140. J Pharm Sci 99:2521-2528.
31. Ghobrial O G, Derendorf H, Hillman J D. 2009. Pharmacodynamic activity of the lantibiotic MU1140. Int J Antimicrob Agents 33:70-74.
32. Ghobrial, O.; Derendorf, H.; Hillman, J. D. J. Pharm. Sci. 2010, 99, 2521-2528.

33. Goldman, R. C.; Baizman, E. R.; Longley, C. B.; Branstrom, A. A. FEMS Microbiol. Lett. 2000, 183, 209-214.
34. Goldsmith C E, Hara Y, Sato T, Nakajima T, Nakanishi S, Mason C, Moore J E, Matsuda M, Coulter W A. 2015. Comparison of antibiotic susceptibility in viridans group streptococci in low and high antibiotic-prescribing General Practices. J Clin Pharm Therap 40:204-207.
35. Guillemot, D., et al., Reduction of antibiotic use in the community reduces the rate of colonization with penicillin G-nonsusceptible *Streptococcus pneumoniae*. Clinical Infectious Diseases: An Official Publication Of The Infectious Diseases Society Of America, 2005. 41(7): p. 930-938.
36. Hart, P.; Oppedijk, S. F.; Breukink, E.; Martin, N. I. Biochemistry 2016, 55, 232-237.
37. Hasper H E, Kramer N E, Smith J L, Hillman J D, Zachariah C, Kuipers O P, de Kruijff B, Breukink E. 2006. An alternative bactericidal mechanism of action for lantibiotic peptides that target lipid II. Science 313:1636-1637.
38. Hasper, H. E.; de Kruijff, B.; Breukink, E. Biochemistry 2004, 43, 11567-11575.
39. Hathaway L J, Brugger S D, Morand B, Bangert M, Rotzetter J U, Hauser C, Graber W A, Gore S, Kadioglu A, Mühlemann K. 2012. Capsule type of *Streptococcus pneumoniae* determines growth phenotype. Plos Pathogens 8:e1002574-e1002574.
40. Hau, I., et al., Impact of pneumococcal conjugate vaccines on microbial epidemiology and clinical outcomes of acute otitis media. Paediatric Drugs, 2014. 16(1): p. 1-12.
41. Hayakawa, Y.; Sasaki, K.; Nagai, K.; Shin-ya, K.; Furihata, K. J. Antibiot. 2006, 59, 6-10.
42. Hillman J D, Novak J, Sagura E, Gutierrez J A, Brooks T A, Crowley P J, Hess M, Azizi A, Leung K P, Cvitkovitch D, Bleiweis A S. 1998. Genetic and biochemical analysis of mutacin 1140, a lantibiotic from *Streptococcus mutans*. Infect Immun 66:2743-2749.
43. Hillman, J. D. Antonie Van Leeuwenhoek 2002, 82, 361-366.
44. Hsu, S. T. D.; Breukink, E.; Tischenko, E.; Lutters, M. A. G.; de Kruijff, B.; Kaptein, R.; Bonvin, A.; van Nuland, N. A. J. Nat. Struct. Mol. Biol. 2004, 11, 963-967.
45. Hughes, J.; Smith, T. W.; Kosterlitz, H. W.; Fothergill, L. A.; Morgan, B. A.; Morris, H. R. Nature 1975, 258, 577-579.
46. Islam, M. R.; Nishie, M.; Nagao, J.; Zendo, T.; Keller, S.; Nakayama, J.; Kohda, D.; Sahl, H. G.; Sonomoto, K. J Am Chem Soc 2012, 134, 3687-90.
47. Joshi, P. R.; McGuire, J.; Neff, J. A. J. Biomed. Mater. Res. Part B 2009, 91B, 128-134.
48. Kaur, R., et al., Correlation of nasopharyngeal cultures prior to and at onset of acute otitis media with middle ear fluid cultures. BMC Infectious Diseases, 2014. 14: p. 640-640.
49. Kellner, R.; Jung, G.; Horner, T.; Zahner, H.; Schnell, N.; Entian, K. D.; Gotz, F. Eur. J. Biochem. 1988, 177, 53-59.
50. Konno M, Baba S, Mikawa H, Hara K, Matsumoto F, Kaga K, Nishimura T, Kobayashi T, Furuya N, Moriyama H, Okamoto Y, Furukawa M, Yamanaka N, Matsushima T, Yoshizawa Y, Kohno S, Kobayashi K, Morikawa A, Koizumi S, Sunakawa K, Inoue M, Ubukata K. 2006. Study of upper respiratory tract bacterial flora: first report. Variations in upper respiratory tract bacterial flora in patients with acute upper respiratory tract infection and healthy subjects and variations by subject age. J Infect Chemother 12:83-96.
51. Konno, M., et al., Study of nasopharyngeal bacterial flora. Variations in nasopharyngeal bacterial flora in schoolchildren and adults when administered antimicrobial agents. Journal Of Infection And Chemotherapy: Official Journal Of The Japan Society Of Chemotherapy, 2007. 13(4): p. 235-254.
52. Kupke, T.; Gotz, F. FEMS Microbiol. Lett. 1997, 153, 25-32.
53. Kupke, T.; Kempter, C.; Gnau, V.; Jung, G.; Gotz, F. J. Biol. Chem. 1994, 269, 5653-5659.
54. Kupke, T.; Kempter, C.; Jung, G.; Gotz, F. J. Biol. Chem. 1995, 270, 11282-11289.
55. Lepak, A. J., et al., In vivo pharmacokinetics and pharmacodynamics of the lantibiotic NAI-107 in a neutropenic murine thigh infection model. Antimicrobial Agents And Chemotherapy, 2015. 59(2): p. 1258-1264.
56. Levengood, M. R.; Knerr, P. J.; Oman, T. J.; van der Donk, W. A. J. Am. Chem. Soc. 2009, 131, 12024-12025.
57. Li, Y.-H.; Tang, N.; Aspiras, M. B.; Lau, P. C. Y.; Lee, J. H.; Ellen, R. P.; Cvitkovitch, D. G. J. Bacteriol. 2002, 184, 2699-2708.
58. Lubelski, J.; Khusainov, R.; Kuipers, 0. P. J Biol Chem 2009, 284, 25962-72.
59. Maher, S.; Vilk, G.; Kelleher, F.; Lajoie, G.; McClean, S. Int. J. Pept. Res. Ther. 2009, 15, 219-226.
60. Meyer, H. E.; Heber, M.; Eisermann, B.; Korte, H.; Metzger, J. W.; Jung, G. Anal. Biochem. 1994, 223, 185-190.
61. Moine, P., et al., In vivo efficacy of a broad-spectrum cephalosporin, ceftriaxone, against penicillin-susceptible and -resistant strains of *Streptococcus pneumoniae* in a mouse pneumonia model. Antimicrobial Agents and Chemotherapy, 1994. 38(9): p. 1953-1958.
62. Mota-Meira, M., H. Morency, and M. C. Lavoie, In vivo activity of mutacin B-Ny266. The Journal Of Antimicrobial Chemotherapy, 2005. 56(5): p. 869-871.
63. Mutagenesis of Lysine 12 Leads to the Identification of Derivatives of Nisin A with Enhanced Antimicrobial Activity. Plos One 2013, 8, e58530.
64. Novak, R., et al., Penicillin tolerance genes of *Streptococcus pneumoniae*: The ABC-type manganese complex Psa. Mol. Microbiol., 1998. 29: p. 1285-1296.
65. Okesli, A.; Cooper, L. E.; Fogle, E. J.; van der Donk, W. A. J. Am. Chem. Soc. 2011, 133, 13753-13760.
66. Olivares A, T. J., Arellano-Galindo J, Zuñiga G, Escalona G, Vigueras J C, Marin P, Xicohtencatl J, Valencia P, Velázquez-Guadarram N. 2011. pep27 and lytA in Vancomycin-Tolerant Pneumococci. J Microbiol Biotechnol. 21:1345-51.
67. Ortega, M. A.; Hao, Y.; Zhang, Q.; Walker, M. C.; van der Donk, W. A.; Nair, S. K. Nature 2015, 517, 509-512.
68. Paiva, A. D.; Breukink, E.; Mantovani, H. C. Antimicrob Agents Chemother 2011, 55, 5284-93.
69. Pettigrew, M. M., et al., Upper respiratory tract microbial communities, acute otitis media pathogens, and antibiotic use in healthy and sick children. Applied And Environmental Microbiology, 2012. 78(17): p. 6262-6270.
70. Qi, F. X.; Chen, P.; Caufield, P. W. Appl. Environ. Microbiol. 1999, 65, 652-658.
71. Ross, A. C.; Liu, H. Q.; Pattabiraman, V. R.; Vederas, J. C. J. Am. Chem. Soc. 2010, 132, 462-463.
72. Scherer, K. M.; Spille, J. H.; Sahl, H. G.; Grein, F.; Kubitscheck, U. Biophys. J. 2015, 108, 1114-1124.

73. Shi, Y. X.; Bueno, A.; van der Donk, W. A. Chem. Commun. 2012, 48 (89), 10966-10968.
74. Silhavy, T. J., D. Kahne, and S. Walker, The bacterial cell envelope. Cold Spring Harbor Perspectives In Biology, 2010. 2(5): p. a000414-a000414.
75. Sit, C. S.; Yoganathan, S.; Vederas, J. C. Accounts Chem. Res. 2011, 44, 261-268.
76. Smith L, Hasper H, Breukink E, Novak J, Cerkasov J, Hillman J D, Wilson-Stanford S, Orugunty R S. 2008. Elucidation of the Antimicrobial Mechanism of Mutacin 1140. Biochemistry. 47:3308-14.
77. Smith L, Novak J, Rocca J, McClung S, Hillman J D, Edison A S. 2000. Covalent structure of mutacin 1140 and a novel method for the rapid identification of lantibiotics. Eur J Biochem 267:6810-6816.
78. Smith, L. and J. D. Hillman, Therapeutic potential of type A (I) lantibiotics, a group of cationic peptide antibiotics. Current Opinion In Microbiology, 2008. 11(5): p. 401-408.
79. Smith, L., et al., Elucidation of the Antimicrobial Mechanism of Mutacin 1140. Biochemistry, 2008: p. accepted.
80. Smith, L.; Zachariah, C.; Thirumoorthy, R.; Rocca, J.; Novak, J.; Hillman, J. D.; Edison, A. S. Biochemistry 2003, 42, 10372-10384.
81. Steinhoff, M. C., Animal models for protein pneumococcal vaccine evaluation: A summary. Vaccine. 25(13): p. 2465-2470.
82. Strauss, E.; Zhai, H.; Brand, L. A.; McLafferty, F. W.; Begley, T. P. Biochemistry 2004, 43, 15520-15533.
83. Stubbendieck, R. M.; Straight, P. D. PLoS genetics 2015, 11, e1005722.
84. Suda, S.; Lawton, E. M.; Wistuba, D.; Cotter, P. D.; Hill, C.; Ross, R. P. J. Bacteriol. 2012, 194, 708-714.
85. Tabor, A. B. Bioorganic Chem. 2014, 55, 39-50.
86. Turner, R. D., et al., Peptidoglycan architecture can specify division planes in *Staphylococcus aureus*. Nature Communications, 2010. 1: p. 26-26.
87. van Heel, A. J., M. Montalban-Lopez, and O. P. Kuipers, Evaluating the feasibility of lantibiotics as an alternative therapy against bacterial infections in humans. Expert Opinion On Drug Metabolism & Toxicology, 2011. 7(6): p. 675-680.
88. van Heijenoort, J., Formation of the glycan chains in the synthesis of bacterial peptidoglycan. Glycobiology, 2001. 11(3): p. 25R-36R.
89. Velasquez, J. E.; Zhang, X. G.; van der Donk, W. A. Chem. Biol. 2011, 18, 857-867.
90. Vouillamoza J, Entenza J, Giddey M, Fischetti V, Moreillon P, Resch G. Bactericidal synergism between daptomycin and the phage lysin Cpl-1 in a mouse model of pneumococcal bacteraemia. 2013. Inter J Antimicrob Agents 42:416-421.
91. Wilson-Stanford, S.; Kalli, A.; Hakansson, K.; Kastrantas, J.; Orugunty, R. S.; Smith, L. Appl. Environ. Microbiol. 2009, 75, 1381-1387.
92. Xie, Z. J.; Okinaga, T.; Qi, F. X.; Zhang, Z. J.; Merritt, J. Appl. Environ. Microbiol. 2011, 77, 8025-8033.
93. Yamada, K., et al., In vivo efficacy of KRP-109, a novel elastase inhibitor, in a murine model of severe pneumococcal pneumonia. Pulmonary Pharmacology & Therapeutics, 2011. 24(6): p. 660-665.
94. Yeaman M R, Yount N Y. 2003. Mechanisms of antimicrobial peptide action and resistance. Pharmacol Rev 55:27-55.

We claim:

1. A modified lantibiotic selected from mutacin 1140 comprising SEQ ID NO: 24 and mutacin B-Ny266 comprising SEQ ID NO: 23, said modified lantibiotic having a free carboxy group at the C-terminus, wherein:
   a) mutacin 1140 has mutations at:
      i) one or more of Leu6 and Arg13 to an amino acid selected from alanine, glycine, valine, leucine or isoleucine,
      ii) one or more of Leu6 and Arg13 to alanine, or
      iii) Lys2 to an amino acid selected from alanine, glycine, valine, leucine or isoleucine, or
   b) mutacin B-Ny266 has mutations at:
      i) one or more of Phe6 and Lys13 to an amino acid selected from alanine, glycine, valine, leucine or isoleucine,
      ii) one or more of Phe6 and Lys13 to alanine, or
      iii) Lys2 to an amino acid selected from alanine, glycine, valine, leucine or isoleucine; or
   c) mutacin 1140 or mutacin B-Ny266 is mutated at the following amino acid positions:

| Amino acid position(s) | Original amino acid(s) (respectively) | Replacement amino acid(s), respectively |
|---|---|---|
| 5 | Serine | Glycine |
| 5 | Serine | Threonine |
| 5 | Serine | Glutamate |
| 5 | Serine | Alanine |
| 13 | Arginine | Alanine |
| 14 | Threonine | Glycine |
| 14 | Threonine | Alanine |
| 15 | Glycine | Alanine |
| 12 | Alanine | Threonine |
| 4 | Tryptophan | Serine |
| 6 | Leucine | Serine |
| 12, 14 | Alanine and Threonine | Threonine and Glycine |
| 13, 14 | Arginine and Threonine | Alanine and Alanine |
| 14, 15 | Threonine and Glycine | Alanine and Alanine |
| 5, 14 | Serine and Threonine | Glycine and Glycine |
| 5, 14 | Serine and Threonine | Alanine and Glycine |
| 5, 14 | Serine and Threonine | Threonine and Glycine |
| 5, 14 | Serine and Threonine | Alanine and Serine |
| 5, 14 | Serine and Threonine | Alanine and Alanine |
| 5, 14 | Serine and Threonine | Glycine and Alanine |
| 5, 14 | Serine and Threonine | Glutamate and Alanine |
| 5, 14 | Serine and Threonine | Threonine and Alanine |
| 5, 12 | Serine and Alanine | Alanine and Serine |
| 5, 13 | Serine and Arginine | Alanine and Serine |
| 13, 14 and 15 | Arginine, Threonine and Glycine | Alanine, Alanine and Alanine |
| 5, 13 and 14 | Serine, Arginine and Threonine | Glcyine, Alanine and Alanine |
| 4, 5 and 14 | Tryptophan, Serine and Threonine | Serine, Alanine and Alanine |
| 5, 6 and 14 | Serine, Leucine and Threonine | Alanine, Serine and Alanine |

-continued

| Amino acid position(s) | Original amino acid(s) (respectively) | Replacement amino acid(s), respectively |
|---|---|---|
| 5, 12 and 14 | Serine, Alanine and Threonine | Alanine, Serine and Alanine |
| 5, 13 and 14 | Serine, Arginine and Threonine | Alanine, Serine and Alanine |
| 12, 13 and 14 | Alanine, Arginine and Threonine | Glycine, Glycine and Glycine. |

2. The modified lantibiotic according to claim 1, wherein said modified lantibiotic is:
   a) mutacin 1140 having mutations at:
      i) one or more of Leu6 and Arg13 to an amino acid selected from alanine, glycine, valine, leucine or isoleucine,
      ii) one or more of Leu6 and Arg13 to alanine, or
      iii) Lys2 to an amino acid selected from alanine, glycine, valine, leucine or isoleucine, or
   b) mutacin B-Ny266 having mutations at:
      i) one or more of Phe6 and Lys13 to an amino acid selected from alanine, glycine, valine, leucine or isoleucine,
      ii) one or more of Phe6 and Lys13 to alanine, or
      iii) Lys2 to an amino acid selected from alanine, glycine, valine, leucine or isoleucine.

3. The modified lantibiotic according to claim 2, wherein the mutant mutacin 1140 has an amino acid mutation at position 2 or 13.

4. The modified lantibiotic according to claim 3, wherein mutacin 1140 has an amino acid mutation at position 2 selected from alanine, glycine, valine, leucine or isoleucine.

5. The modified lantibiotic according to claim 4, wherein mutacin 1140 is mutated to have an alanine at position 2.

6. The modified lantibiotic according to claim 3, wherein mutacin 1140 has an amino acid mutation at position 13 selected from alanine, glycine, valine, leucine or isoleucine.

7. The modified lantibiotic according to claim 6, wherein mutacin 1140 is mutated to have an alanine at position 13.

8. A pharmaceutical composition comprising mutacin modified lantibiotic according to claim 1 and pharmaceutically acceptable carrier or excipient.

9. A lantibiotic peptide comprising SEQ ID NO: 24 having an amino acid mutation at position 2 in which the lysine residue is substituted with an alanine and having free C-terminal carboxy group or a decarboxylated C-terminal amino acid.

10. The lantibiotic peptide according to claim 9, wherein the mutant mutated mutacin has a free C-terminal carboxy group.

11. The lantibiotic peptide according to claim 9, wherein the mutant mutated mutacin is decarboxylated at the C-terminal amino acid.

12. A pharmaceutical composition comprising mutacin lantibiotic peptide according to claim 9 and pharmaceutically acceptable carrier or excipient.

13. A mutated mutacin selected from mutacin 1140 comprising SEQ ID NO: 24 and mutacin B-Ny266 comprising SEQ ID NO: 23, said mutated mutacin being produced by a bacterium genetically modified to inactivate a gene that encodes a decarboxylase enzyme that decarboxylates the cysteine at the C-terminus of said mutant mutacin, wherein:
   a) mutacin 1140 has mutations at:
      i) one or more of Leu6 and Arg13 to an amino acid selected from alanine, glycine, valine, leucine or isoleucine,
      ii) one or more of Leu6 and Arg13 to alanine, or
      iii) Lys2 to an amino acid selected from alanine, glycine, valine, leucine or isoleucine, or
   b) mutacin B-Ny266 has mutations at:
      i) one or more of Phe6 and Lys13 to an amino acid selected from alanine, glycine, valine, leucine or isoleucine,
      ii) one or more of Phe6 and Lys13 to alanine, or
      iii) Lys2 to an amino acid selected from alanine, glycine, valine, leucine or isoleucine; or
   c) mutacin 1140 or mutacin B-Ny266 is mutated at the following amino acid positions:

| Amino acid position(s) | Original amino acid(s) (respectively) | Replacement amino acid(s), respectively |
|---|---|---|
| 5 | Serine | Glycine |
| 5 | Serine | Threonine |
| 5 | Serine | Glutamate |
| 5 | Serine | Alanine |
| 13 | Arginine | Alanine |
| 14 | Threonine | Glycine |
| 14 | Threonine | Alanine |
| 15 | Glycine | Alanine |
| 12 | Alanine | Threonine |
| 4 | Tryptophan | Serine |
| 6 | Leucine | Serine |
| 12, 14 | Alanine and Threonine | Threonine and Glycine |
| 13, 14 | Arginine and Threonine | Alanine and Alanine |
| 14, 15 | Threonine and Glycine | Alanine and Alanine |
| 5, 14 | Serine and Threonine | Glycine and Glycine |
| 5, 14 | Serine and Threonine | Alanine and Glycine |
| 5, 14 | Serine and Threonine | Threonine and Glycine |
| 5, 14 | Serine and Threonine | Alanine and Serine |
| 5, 14 | Serine and Threonine | Alanine and Alanine |
| 5, 14 | Serine and Threonine | Glycine and Alanine |
| 5, 14 | Serine and Threonine | Glutamate and Alanine |
| 5, 14 | Serine and Threonine | Threonine and Alanine |
| 5, 12 | Serine and Alanine | Alanine and Serine |
| 5, 13 | Serine and Arginine | Alanine and Serine |
| 13, 14 and 15 | Arginine, Threonine and Glycine | Alanine, Alanine and Alanine |
| 5, 13 and 14 | Serine, Arginine and Threonine | Glycine, Alanine and Alanine |
| 4, 5 and 14 | Tryptophan, Serine and Threonine | Serine, Alanine and Alanine |
| 5, 6 and 14 | Serine, Leucine and Threonine | Alanine, Serine and Alanine |
| 5, 12 and 14 | Serine, Alanine and Threonine | Alanine, Serine and Alanine |
| 5, 13 and 14 | Serine, Arginine and Threonine | Alanine, Serine and Alanine |
| 12, 13 and 14 | Alanine, Arginine and Threonine | Glycine, Glycine and Glycine. |

14. The mutated mutacin according to claim 13, wherein said mutant mutated mutacin is:
   a) mutacin 1140 having mutations at:
      i) one or more of Leu6 and Arg13 to an amino acid selected from alanine, glycine, valine, leucine or isoleucine,
      ii) one or more of Leu6 and Arg13 to alanine, or
      iii) Lys2 to an amino acid selected from alanine, glycine, valine, leucine or isoleucine, or
   b) a mutacin B-Ny266 having mutations at:
      i) one or more of Phe6 and Lys13 to an amino acid selected from alanine, glycine, valine, leucine or isoleucine,
      ii) one or more of Phe6 and Lys13 to alanine, or
      iii) Lys2 to an amino acid selected from alanine, glycine, valine, leucine or isoleucine.

15. The mutated mutacin according to claim 13, wherein the mutated mutacin 1140 has an amino acid mutation at position 2 or 13.

16. The mutated mutacin according to claim 15, wherein the mutated mutacin 1140 has an amino acid mutation at position 2 selected from alanine, glycine, valine, leucine or isoleucine.

17. The mutated mutacin according to claim 16, wherein the mutated mutacin 1140 is mutated to have an alanine at position 2.

18. The mutated mutacin according to claim 15, wherein the mutated mutacin 1140 has an amino acid mutation at position 13 selected from alanine, glycine, valine, leucine or isoleucine.

19. The mutated mutacin according to claim 18, wherein the mutated mutacin 1140 is mutated to have an alanine at position 13.

20. A pharmaceutical composition comprising a mutated mutacin according to claim 13 and pharmaceutically acceptable carrier or excipient.

* * * * *

UNITED STATES PATENT AND TRADEMARK OFFICE
CERTIFICATE OF CORRECTION

PATENT NO.         : 10,577,399 B2
APPLICATION NO.    : 15/797001
DATED              : March 3, 2020
INVENTOR(S)        : James L. Smith and Jerome Escano Page 1 of 1

It is certified that error appears in the above-identified patent and that said Letters Patent is hereby corrected as shown below:

In the Specification

Column 24,
Lines 49-50, "of the decarboxylation must occur" should read --of the dehydration and cyclase modifications found in lantibiotics[3, 52-54]. Previous data suggest that decarboxylation must occur--.

In the Claims

Column 67,
Lines 41-42, "comprising mutacin modified lantibiotic" should read --comprising a modified lantibiotic--.
Lines 55-56, "comprising mutacin lantibiotic peptide" should read --comprising a lantibiotic peptide--.

Signed and Sealed this
Thirteenth Day of October, 2020

Andrei Iancu
*Director of the United States Patent and Trademark Office*

SEQUENCE LISTING

<160> NUMBER OF SEQ ID NOS: 50

<210> SEQ ID NO 1
<211> LENGTH: 69
<212> TYPE: PRT
<213> ORGANISM: Bacillus licheniformis

<400> SEQUENCE: 1

Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys Pro Thr Thr Lys
    50                  55                  60

Cys Thr Ser Arg Cys
65

<210> SEQ ID NO 2
<211> LENGTH: 68
<212> TYPE: PRT
<213> ORGANISM: Lactobacillus sakei L45

<400> SEQUENCE: 2

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp Ser

```
                    20                  25                  30
Thr Pro Val Leu Ala Ser Val Ala Val Ser Met Glu Leu Leu Pro Thr
                35                  40                  45
Ala Ser Val Leu Tyr Ser Asp Val Ala Gly Cys Phe Lys Tyr Ser Ala
            50                  55                  60
Lys His His Cys
65

<210> SEQ ID NO 3
<211> LENGTH: 48
<212> TYPE: PRT
<213> ORGANISM: Streptococcus salivarius

<400> SEQUENCE: 3

Met Lys Asn Ser Lys Asp Ile Leu Asn Asn Ala Ile Glu Glu Val Ser
1               5                   10                  15
Glu Lys Glu Leu Met Glu Val Ala Gly Gly Lys Arg Gly Ser Gly Trp
                20                  25                  30
Ile Ala Thr Ile Thr Asp Asp Cys Pro Asn Ser Val Phe Val Cys Cys
            35                  40                  45

<210> SEQ ID NO 4
<211> LENGTH: 53
<212> TYPE: PRT
<213> ORGANISM: Streptococcus mutans

<400> SEQUENCE: 4

Met Asn Lys Leu Asn Ser Asn Ala Val Val Ser Leu Asn Glu Val Ser
1               5                   10                  15
Asp Ser Glu Leu Asp Thr Ile Leu Gly Gly Asn Arg Trp Trp Gln Gly
                20                  25                  30
Val Val Pro Thr Val Ser Tyr Glu Cys Arg Met Asn Ser Trp Gln His
            35                  40                  45
Val Phe Thr Cys Cys
        50

<210> SEQ ID NO 5
<211> LENGTH: 65
<212> TYPE: PRT
<213> ORGANISM: Lactococcus lactis

<400> SEQUENCE: 5

Met Lys Glu Lys Asn Met Lys Lys Asn Asp Thr Ile Glu Leu Gln Leu
1               5                   10                  15
Gly Lys Tyr Leu Glu Asp Asp Met Ile Glu Leu Ala Glu Gly Asp Glu
                20                  25                  30
Ser His Gly Gly Thr Thr Pro Ala Thr Pro Ala Ile Ser Ile Leu Ser
            35                  40                  45
Ala Tyr Ile Ser Thr Asn Thr Cys Pro Thr Thr Lys Cys Thr Arg Ala
        50                  55                  60
Cys
65

<210> SEQ ID NO 6
<211> LENGTH: 64
<212> TYPE: PRT
<213> ORGANISM: Actinoplanes liguriensis

<400> SEQUENCE: 6
```

```
Met Ser Ala Leu Ala Ile Glu Lys Ser Trp Lys Asp Val Asp Leu Arg
1               5                   10                  15

Asp Gly Ala Thr Ser His Pro Ala Gly Leu Phe Gly Glu Leu Thr
            20                  25                  30

Phe Glu Asp Leu Arg Glu Asp Arg Thr Ile Tyr Ala Ala Ser Ser Gly
            35                  40                  45

Trp Val Cys Thr Leu Thr Ile Glu Cys Gly Thr Val Ile Cys Ala Cys
50              55                  60
```

<210> SEQ ID NO 7
<211> LENGTH: 68
<212> TYPE: PRT
<213> ORGANISM: Bacillus sp.

<400> SEQUENCE: 7

```
Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
            35                  40                  45

Cys Thr Phe Thr Leu Pro Gly Gly Gly Val Cys Thr Leu Thr Ser
50              55                  60

Glu Cys Ile Cys
65
```

<210> SEQ ID NO 8
<211> LENGTH: 52
<212> TYPE: PRT
<213> ORGANISM: Staphylococcus epidermidis

<400> SEQUENCE: 8

```
Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
            35                  40                  45

Ser Tyr Cys Cys
    50
```

<210> SEQ ID NO 9
<211> LENGTH: 52
<212> TYPE: PRT
<213> ORGANISM: Staphylococcus gallinarum

<400> SEQUENCE: 9

```
Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
            35                  40                  45

Ser Tyr Cys Cys
    50
```

<210> SEQ ID NO 10
<211> LENGTH: 63
<212> TYPE: PRT

<213> ORGANISM: Streptococcus mutans

<400> SEQUENCE: 10

Met Ser Asn Thr Gln Leu Leu Glu Val Leu Gly Thr Glu Thr Phe Asp
1               5                   10                  15

Val Gln Glu Asn Leu Phe Thr Phe Asp Thr Thr Asp Thr Ile Val Ala
            20                  25                  30

Glu Ser Asn Asp Asp Pro Asp Thr Arg Phe Lys Ser Trp Ser Phe Cys
        35                  40                  45

Thr Pro Gly Cys Ala Lys Thr Gly Ser Phe Asn Ser Tyr Cys Cys
    50                  55                  60

<210> SEQ ID NO 11
<211> LENGTH: 63
<212> TYPE: PRT
<213> ORGANISM: Streptococcus mutans

<400> SEQUENCE: 11

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg Phe Lys Ser Trp Ser Leu Cys
        35                  40                  45

Thr Pro Gly Cys Ala Arg Thr Gly Ser Phe Asn Ser Tyr Cys Cys
    50                  55                  60

<210> SEQ ID NO 12
<211> LENGTH: 47
<212> TYPE: PRT
<213> ORGANISM: Ruminococcus gnavus

<400> SEQUENCE: 12

Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45

<210> SEQ ID NO 13
<211> LENGTH: 57
<212> TYPE: PRT
<213> ORGANISM: Microbispora corallina

<400> SEQUENCE: 13

Met Pro Ala Asp Ile Leu Glu Thr Arg Thr Ser Glu Thr Glu Asp Leu
1               5                   10                  15

Leu Asp Leu Asp Leu Ser Ile Gly Val Glu Glu Ile Thr Ala Gly Pro
            20                  25                  30

Ala Val Thr Ser Trp Ser Leu Cys Thr Pro Gly Cys Thr Ser Pro Gly
        35                  40                  45

Gly Gly Ser Asn Cys Ser Phe Cys Cys
    50                  55

<210> SEQ ID NO 14
<211> LENGTH: 32
<212> TYPE: PRT
<213> ORGANISM: Bacillus licheniformis

```
<400> SEQUENCE: 14

Thr Thr Pro Ala Thr Thr Ser Ser Trp Thr Cys Ile Thr Ala Gly Val
1               5                   10                  15

Thr Val Ser Ala Ser Leu Cys Pro Thr Thr Lys Cys Thr Ser Arg Cys
                20                  25                  30

<210> SEQ ID NO 15
<211> LENGTH: 37
<212> TYPE: PRT
<213> ORGANISM: Lactobacillus sakei L45

<400> SEQUENCE: 15

Ser Thr Pro Val Leu Ala Ser Val Ala Val Ser Met Glu Leu Leu Pro
1               5                   10                  15

Thr Ala Ser Val Leu Tyr Ser Asp Val Ala Gly Cys Phe Lys Tyr Ser
                20                  25                  30

Ala Lys His His Cys
            35

<210> SEQ ID NO 16
<211> LENGTH: 22
<212> TYPE: PRT
<213> ORGANISM: Streptococcus salivarius

<400> SEQUENCE: 16

Lys Arg Gly Ser Gly Trp Ile Ala Thr Ile Thr Asp Asp Cys Pro Asn
1               5                   10                  15

Ser Val Phe Val Cys Cys
            20

<210> SEQ ID NO 17
<211> LENGTH: 27
<212> TYPE: PRT
<213> ORGANISM: Streptococcus mutans

<400> SEQUENCE: 17

Asn Arg Trp Trp Gln Gly Val Val Pro Thr Val Ser Tyr Glu Cys Arg
1               5                   10                  15

Met Asn Ser Trp Gln His Val Phe Thr Cys Cys
                20                  25

<210> SEQ ID NO 18
<211> LENGTH: 29
<212> TYPE: PRT
<213> ORGANISM: Lactococcus lactis subsp. lactis (Streptococcus lactis)

<400> SEQUENCE: 18

Thr Thr Pro Ala Thr Pro Ala Ile Ser Ile Leu Ser Ala Tyr Ile Ser
1               5                   10                  15

Thr Asn Thr Cys Pro Thr Thr Lys Cys Thr Arg Ala Cys
                20                  25

<210> SEQ ID NO 19
<211> LENGTH: 19
<212> TYPE: PRT
<213> ORGANISM: Actinoplanes liguriensis

<400> SEQUENCE: 19

Ser Ser Gly Trp Val Cys Thr Leu Thr Ile Glu Cys Gly Thr Val Ile
1               5                   10                  15

Cys Ala Cys
```

<210> SEQ ID NO 20
<211> LENGTH: 20
<212> TYPE: PRT
<213> ORGANISM: Bacillus sp.

<400> SEQUENCE: 20

Cys Thr Phe Thr Leu Pro Gly Gly Gly Val Cys Thr Leu Thr Ser
1               5                   10                  15

Glu Cys Ile Cys
            20

<210> SEQ ID NO 21
<211> LENGTH: 22
<212> TYPE: PRT
<213> ORGANISM: Staphylococcus epidermidis

<400> SEQUENCE: 21

Ile Ala Ser Lys Phe Ile Cys Thr Pro Gly Cys Ala Lys Thr Gly Ser
1               5                   10                  15

Phe Asn Ser Tyr Cys Cys
            20

<210> SEQ ID NO 22
<211> LENGTH: 22
<212> TYPE: PRT
<213> ORGANISM: Staphylococcus gallinarum

<400> SEQUENCE: 22

Ile Ala Ser Lys Phe Leu Cys Thr Pro Gly Cys Ala Lys Thr Gly Ser
1               5                   10                  15

Phe Asn Ser Tyr Cys Cys
            20

<210> SEQ ID NO 23
<211> LENGTH: 22
<212> TYPE: PRT
<213> ORGANISM: Streptococcus mutans

<400> SEQUENCE: 23

Phe Lys Ser Trp Ser Phe Cys Thr Pro Gly Cys Ala Lys Thr Gly Ser
1               5                   10                  15

Phe Asn Ser Tyr Cys Cys
            20

<210> SEQ ID NO 24
<211> LENGTH: 22
<212> TYPE: PRT
<213> ORGANISM: Streptococcus mutans

<400> SEQUENCE: 24

Phe Lys Ser Trp Ser Leu Cys Thr Pro Gly Cys Ala Arg Thr Gly Ser
1               5                   10                  15

Phe Asn Ser Tyr Cys Cys
            20

<210> SEQ ID NO 25
<211> LENGTH: 24
<212> TYPE: PRT
<213> ORGANISM: Ruminococcus gnavus

<400> SEQUENCE: 25

```
Gly Asn Gly Val Leu Lys Thr Ile Ser His Glu Cys Asn Met Asn Thr
1               5                   10                  15

Trp Gln Phe Leu Phe Thr Cys Cys
            20
```

```
<210> SEQ ID NO 26
<211> LENGTH: 24
<212> TYPE: PRT
<213> ORGANISM: Microbispora corallina

<400> SEQUENCE: 26

Val Thr Ser Trp Ser Leu Cys Thr Pro Gly Cys Thr Ser Pro Gly Gly
1               5                   10                  15

Gly Ser Asn Cys Ser Phe Cys Cys
            20
```

```
<210> SEQ ID NO 27
<211> LENGTH: 23
<212> TYPE: DNA
<213> ORGANISM: Artificial Sequence
<220> FEATURE:
<223> OTHER INFORMATION: Forward primer

<400> SEQUENCE: 27
gatttgtttc gtaaagaggg ttc                                         23
```

```
<210> SEQ ID NO 28
<211> LENGTH: 22
<212> TYPE: DNA
<213> ORGANISM: Artificial Sequence
<220> FEATURE:
<223> OTHER INFORMATION: Reverse primer

<400> SEQUENCE: 28
ctacatcaat cccagaatca ac                                          22
```

```
<210> SEQ ID NO 29
<211> LENGTH: 42
<212> TYPE: DNA
<213> ORGANISM: Artificial Sequence
<220> FEATURE:
<223> OTHER INFORMATION: Forward primer

<400> SEQUENCE: 29
gagtgttatt gttgctcgga aattatttct ccgttcagtt aa                    42
```

```
<210> SEQ ID NO 30
<211> LENGTH: 41
<212> TYPE: DNA
<213> ORGANISM: Artificial Sequence
<220> FEATURE:
<223> OTHER INFORMATION: Reverse primer

<400> SEQUENCE: 30
ggtatactac tgacagcttc ggtaattgtt ggacaagaat c                     41
```

```
<210> SEQ ID NO 31
<211> LENGTH: 43
<212> TYPE: DNA
<213> ORGANISM: Artificial Sequence
<220> FEATURE:
<223> OTHER INFORMATION: Forward primer

<400> SEQUENCE: 31
ttaactgaac ggagaaataa ttggtaattg ttggacaaga atc                   43
```

<210> SEQ ID NO 32
<211> LENGTH: 43
<212> TYPE: DNA
<213> ORGANISM: Artificial Sequence
<220> FEATURE:
<223> OTHER INFORMATION: Reverse primer

<400> SEQUENCE: 32
gattcttgtc caacaattac caattatttc tccgttcagt taa                43

<210> SEQ ID NO 33
<211> LENGTH: 21
<212> TYPE: PRT
<213> ORGANISM: Artificial Sequence
<220> FEATURE:
<223> OTHER INFORMATION: Mutacin 1140
<220> FEATURE:
<221> NAME/KEY: MISC_FEATURE
<222> LOCATION: (5)..(5)
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
<222> LOCATION: (14)..(14)
<223> OTHER INFORMATION: Xaa = dehydroaminobutyric acid (Dhb)

<400> SEQUENCE: 33

Phe Lys Ala Trp Xaa Leu Ala Xaa Pro Gly Ala Ala Arg Xaa Gly Ala
1               5                   10                  15

Phe Asn Ala Tyr Ala
            20

<210> SEQ ID NO 34
<211> LENGTH: 21
<212> TYPE: PRT
<213> ORGANISM: Artificial Sequence
<220> FEATURE:
<223> OTHER INFORMATION: Epidermin
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
<222> LOCATION: (14)..(14)
<223> OTHER INFORMATION: Xaa = dehydroaminobutyric acid (Dhb)

<400> SEQUENCE: 34

Ile Ala Ala Lys Phe Ile Ala Xaa Pro Gly Ala Ala Lys Xaa Gly Ala
1               5                   10                  15

Phe Asn Ala Tyr Ala
            20

<210> SEQ ID NO 35
<211> LENGTH: 34
<212> TYPE: PRT
<213> ORGANISM: Artificial Sequence
<220> FEATURE:
<223> OTHER INFORMATION: Nisin
<220> FEATURE:
<221> NAME/KEY: MISC_FEATURE
<222> LOCATION: (2)..(2)
<223> OTHER INFORMATION: Xaa = dehydroaminobutyric acid (Dhb)
<220> FEATURE:
<221> NAME/KEY: MISC_FEATURE
<222> LOCATION: (5)..(5)

```
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
<222> LOCATION: (13)..(13)
<223> OTHER INFORMATION: Xaa = aminobutyric acid (Abu)
<220> FEATURE:
<221> NAME/KEY: MISC_FEATURE
<222> LOCATION: (23)..(23)
<223> OTHER INFORMATION: Xaa = aminobutyric acid (Abu)
<220> FEATURE:
<221> NAME/KEY: MISC_FEATURE
<222> LOCATION: (25)..(25)
<223> OTHER INFORMATION: Xaa = aminobutyric acid (Abu)
<220> FEATURE:
<221> NAME/KEY: MISC_FEATURE
<222> LOCATION: (33)..(33)
<223> OTHER INFORMATION: Xaa = dehydroalanine (Dha)

<400> SEQUENCE: 35

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys

<210> SEQ ID NO 36
<211> LENGTH: 19
<212> TYPE: PRT
<213> ORGANISM: Artificial Sequence
<220> FEATURE:
<223> OTHER INFORMATION: Mersacidin
<220> FEATURE:
<221> NAME/KEY: MISC_FEATURE
<222> LOCATION: (2)..(2)
<223> OTHER INFORMATION: Xaa = aminobutyric acid (Abu)
<220> FEATURE:
<221> NAME/KEY: MISC_FEATURE
<222> LOCATION: (12)..(13)
<223> OTHER INFORMATION: Xaa = aminobutyric acid (Abu)
<220> FEATURE:
<221> NAME/KEY: MISC_FEATURE
<222> LOCATION: (15)..(15)
<223> OTHER INFORMATION: Xaa = aminobutyric acid (Abu)
<220> FEATURE:
<221> NAME/KEY: MISC_FEATURE
<222> LOCATION: (16)..(16)
<223> OTHER INFORMATION: Xaa = dehydroalanine (Dha)

<400> SEQUENCE: 36

Ala Xaa Phe Ala Leu Pro Gly Gly Gly Gly Val Xaa Xaa Leu Xaa Xaa
1               5                   10                  15

Glu Ala Ile

<210> SEQ ID NO 37
<211> LENGTH: 22
<212> TYPE: PRT
<213> ORGANISM: Artificial Sequence
<220> FEATURE:
<223> OTHER INFORMATION: Mutacin 1140
<220> FEATURE:
<221> NAME/KEY: MISC_FEATURE
<222> LOCATION: (5)..(5)
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
```

-continued

```
<221> NAME/KEY: MISC_FEATURE
<222> LOCATION: (14)..(14)
<223> OTHER INFORMATION: Xaa = dehydroaminobutyric acid (Dhb)

<400> SEQUENCE: 37

Phe Lys Ala Trp Xaa Leu Ala Xaa Pro Gly Ala Ala Arg Xaa Gly Ala
1               5                   10                  15

Phe Asn Ala Tyr Ala Ala
            20

<210> SEQ ID NO 38
<211> LENGTH: 22
<212> TYPE: PRT
<213> ORGANISM: Artificial Sequence
<220> FEATURE:
<223> OTHER INFORMATION: Edman
<220> FEATURE:
<221> NAME/KEY: MISC_FEATURE
<222> LOCATION: (3)..(3)
<223> OTHER INFORMATION: Xaa = thio-ethyl cysteine (S-EC)
<220> FEATURE:
<221> NAME/KEY: MISC_FEATURE
<222> LOCATION: (7)..(7)
<223> OTHER INFORMATION: Xaa = thio-ethyl cysteine (S-EC)
<220> FEATURE:
<221> NAME/KEY: MISC_FEATURE
<222> LOCATION: (8)..(8)
<223> OTHER INFORMATION: Xaa = beta-methyl thio-ethyl cysteine (BM-S-EC)
<220> FEATURE:
<221> NAME/KEY: MISC_FEATURE
<222> LOCATION: (11)..(11)
<223> OTHER INFORMATION: Xaa = unknown
<220> FEATURE:
<221> NAME/KEY: MISC_FEATURE
<222> LOCATION: (14)..(14)
<223> OTHER INFORMATION: Xaa = aminobutyric acid (Abu)
<220> FEATURE:
<221> NAME/KEY: MISC_FEATURE
<222> LOCATION: (16)..(16)
<223> OTHER INFORMATION: Xaa = thio-ethyl cysteine (S-EC)
<220> FEATURE:
<221> NAME/KEY: MISC_FEATURE
<222> LOCATION: (19)..(19)
<223> OTHER INFORMATION: Xaa = thio-ethyl cysteine (S-EC)
<220> FEATURE:
<221> NAME/KEY: MISC_FEATURE
<222> LOCATION: (21)..(22)
<223> OTHER INFORMATION: Xaa = unknown

<400> SEQUENCE: 38

Phe Lys Xaa Trp Ala Leu Xaa Xaa Pro Gly Xaa Ala Arg Xaa Gly Xaa
1               5                   10                  15

Phe Asn Xaa Tyr Xaa Xaa
            20

<210> SEQ ID NO 39
<211> LENGTH: 21
<212> TYPE: PRT
<213> ORGANISM: Artificial Sequence
<220> FEATURE:
<223> OTHER INFORMATION: Mutacin B-Ny266
<220> FEATURE:
<221> NAME/KEY: MISC_FEATURE
<222> LOCATION: (5)..(5)
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
<222> LOCATION: (14)..(14)
<223> OTHER INFORMATION: Xaa = dehydroaminobutyric acid (Dhb)
```

<400> SEQUENCE: 39

Phe Lys Ala Trp Xaa Phe Ala Xaa Pro Gly Ala Ala Lys Xaa Gly Ala
1               5                   10                  15

Phe Asn Ala Tyr Ala
            20

<210> SEQ ID NO 40
<211> LENGTH: 23
<212> TYPE: PRT
<213> ORGANISM: Artificial Sequence
<220> FEATURE:
<223> OTHER INFORMATION: Microbisporicin
<220> FEATURE:
<221> NAME/KEY: MISC_FEATURE
<222> LOCATION: (2)..(2)
<223> OTHER INFORMATION: Xaa = dehydroaminobutyric acid (Dhb)
<220> FEATURE:
<221> NAME/KEY: MISC_FEATURE
<222> LOCATION: (5)..(5)
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)

<400> SEQUENCE: 40

Val Xaa Ala Trp Xaa Leu Ala Xaa Pro Gly Ala Thr Ala Pro Gly Gly
1               5                   10                  15

Gly Ala Asn Ala Ala Phe Ala
            20

<210> SEQ ID NO 41
<211> LENGTH: 23
<212> TYPE: PRT
<213> ORGANISM: Artificial Sequence
<220> FEATURE:
<223> OTHER INFORMATION: Mutacin I
<220> FEATURE:
<221> NAME/KEY: MISC_FEATURE
<222> LOCATION: (2)..(2)
<223> OTHER INFORMATION: Xaa = dehydroalanine (Dha)
<220> FEATURE:
<221> NAME/KEY: MISC_FEATURE
<222> LOCATION: (5)..(5)
<223> OTHER INFORMATION: Xaa = dehydroalanine (Dha)
<220> FEATURE:
<221> NAME/KEY: MISC_FEATURE
<222> LOCATION: (8)..(8)
<223> OTHER INFORMATION: Xaa = aminobutyric acid (Abu)

<400> SEQUENCE: 41

Phe Xaa Ala Leu Xaa Leu Ala Xaa Leu Gly Ala Thr Gly Val Lys Asn
1               5                   10                  15

Pro Ala Phe Asn Ala Tyr Ala
            20

<210> SEQ ID NO 42
<211> LENGTH: 21
<212> TYPE: PRT
<213> ORGANISM: Artificial Sequence
<220> FEATURE:
<223> OTHER INFORMATION: Gallidermin
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
<222> LOCATION: (14)..(14)

-continued

<223> OTHER INFORMATION: Xaa = dehydroaminobutyric acid (Dhb)

<400> SEQUENCE: 42

Ile Ala Ala Lys Phe Leu Ala Xaa Pro Gly Ala Ala Lys Xaa Gly Ala
1               5                   10                  15

Phe Asn Ala Tyr Ala
            20

<210> SEQ ID NO 43
<211> LENGTH: 19
<212> TYPE: PRT
<213> ORGANISM: Artificial Sequence
<220> FEATURE:
<223> OTHER INFORMATION: Mersacidin
<220> FEATURE:
<221> NAME/KEY: MISC_FEATURE
<222> LOCATION: (2)..(2)
<223> OTHER INFORMATION: Xaa = aminobutyric acid (Abu)
<220> FEATURE:
<221> NAME/KEY: MISC_FEATURE
<222> LOCATION: (12)..(13)
<223> OTHER INFORMATION: Xaa = aminobutyric acid (Abu)
<220> FEATURE:
<221> NAME/KEY: MISC_FEATURE
<222> LOCATION: (15)..(15)
<223> OTHER INFORMATION: Xaa = aminobutyric acid (Abu)
<220> FEATURE:
<221> NAME/KEY: MISC_FEATURE
<222> LOCATION: (16)..(16)
<223> OTHER INFORMATION: Xaa = dehydroalanine (Dha)

<400> SEQUENCE: 43

Ala Xaa Phe Ala Leu Pro Gly Gly Gly Gly Val Xaa Xaa Leu Xaa Xaa
1               5                   10                  15

Glu Ala Ile

<210> SEQ ID NO 44
<211> LENGTH: 32
<212> TYPE: PRT
<213> ORGANISM: Artificial Sequence
<220> FEATURE:
<223> OTHER INFORMATION: Lichenicidin A2
<220> FEATURE:
<221> NAME/KEY: MISC_FEATURE
<222> LOCATION: (1)..(1)
<223> OTHER INFORMATION: Xaa = 2-oxobutanoic acid (2-ob)
<220> FEATURE:
<221> NAME/KEY: MISC_FEATURE
<222> LOCATION: (2)..(2)
<223> OTHER INFORMATION: Xaa = dehydroaminobutyric acid (Dhb)
<220> FEATURE:
<221> NAME/KEY: MISC_FEATURE
<222> LOCATION: (5)..(6)
<223> OTHER INFORMATION: Xaa = dehydroaminobutyric acid (Dhb)
<220> FEATURE:
<221> NAME/KEY: MISC_FEATURE
<222> LOCATION: (8)..(8)
<223> OTHER INFORMATION: Xaa = dehydroalanine (Dha)
<220> FEATURE:
<221> NAME/KEY: MISC_FEATURE
<222> LOCATION: (13)..(13)
<223> OTHER INFORMATION: Xaa = dehydroaminobutyric acid (Dhb)
<220> FEATURE:
<221> NAME/KEY: MISC_FEATURE
<222> LOCATION: (17)..(17)
<223> OTHER INFORMATION: Xaa = dehydroaminobutyric acid (Dhb)
<220> FEATURE:
<221> NAME/KEY: MISC_FEATURE
<222> LOCATION: (25)..(25)
<223> OTHER INFORMATION: Xaa = aminobutyric acid (Abu)
<220> FEATURE:
<221> NAME/KEY: MISC_FEATURE
<222> LOCATION: (26)..(26)

<223> OTHER INFORMATION: Xaa = dehydroaminobutyric acid (Dhb)
<220> FEATURE:
<221> NAME/KEY: MISC_FEATURE
<222> LOCATION: (29)..(29)
<223> OTHER INFORMATION: Xaa = aminobutyric acid (Abu)

<400> SEQUENCE: 44

Xaa Xaa Pro Ala Xaa Xaa Ala Xaa Trp Thr Ala Ile Xaa Ala Gly Val
1               5                   10                  15

Xaa Val Ala Ala Ser Leu Ala Pro Xaa Xaa Lys Ala Xaa Ser Arg Ala
            20                  25                  30

<210> SEQ ID NO 45
<211> LENGTH: 36
<212> TYPE: PRT
<213> ORGANISM: Artificial Sequence
<220> FEATURE:
<223> OTHER INFORMATION: Lactocin S
<220> FEATURE:
<221> NAME/KEY: MISC_FEATURE
<222> LOCATION: (1)..(1)
<223> OTHER INFORMATION: Xaa = dehydroaminobutyric acid (Dhb)
<220> FEATURE:
<221> NAME/KEY: MISC_FEATURE
<222> LOCATION: (6)..(6)
<223> OTHER INFORMATION: Ala is in the D confirmation
<220> FEATURE:
<221> NAME/KEY: MISC_FEATURE
<222> LOCATION: (10)..(10)
<223> OTHER INFORMATION: Ala is in the D confirmation
<220> FEATURE:
<221> NAME/KEY: MISC_FEATURE
<222> LOCATION: (18)..(18)
<223> OTHER INFORMATION: Ala is in the D confirmation

<400> SEQUENCE: 45

Xaa Pro Val Leu Ala Ala Val Ala Val Ala Met Glu Leu Leu Pro Thr
1               5                   10                  15

Ala Ala Val Leu Tyr Ala Asp Val Ala Gly Ala Phe Lys Tyr Ala Ala
            20                  25                  30

Lys His His Ala
        35

<210> SEQ ID NO 46
<211> LENGTH: 28
<212> TYPE: PRT
<213> ORGANISM: Artificial Sequence
<220> FEATURE:
<223> OTHER INFORMATION: Mutacin II
<220> FEATURE:
<221> NAME/KEY: MISC_FEATURE
<222> LOCATION: (10)..(10)
<223> OTHER INFORMATION: Xaa = aminobutyric acid (Abu)
<220> FEATURE:
<221> NAME/KEY: MISC_FEATURE
<222> LOCATION: (25)..(25)
<223> OTHER INFORMATION: Xaa = dehydroaminobutyric acid (Dhb)

<400> SEQUENCE: 46

Asn Arg Trp Trp Gln Gly Val Val Pro Xaa Ile Ala His Glu Ala Asn
1               5                   10                  15

Met Asn Ala Trp Gln Phe Val Phe Xaa Ala Ala Ser
            20                  25

<210> SEQ ID NO 47
<211> LENGTH: 22
<212> TYPE: PRT
<213> ORGANISM: Artificial Sequence
<220> FEATURE:

```
<223> OTHER INFORMATION: Salivaricin
<220> FEATURE:
<221> NAME/KEY: MISC_FEATURE
<222> LOCATION: (4)..(4)
<223> OTHER INFORMATION: Xaa = dehydroalanine (Dha)
<220> FEATURE:
<221> NAME/KEY: MISC_FEATURE
<222> LOCATION: (9)..(9)
<223> OTHER INFORMATION: Xaa = aminobutyric acid (Abu)
<220> FEATURE:
<221> NAME/KEY: MISC_FEATURE
<222> LOCATION: (11)..(11)
<223> OTHER INFORMATION: Xaa = aminobutyric acid (Abu)

<400> SEQUENCE: 47

Asn Arg Gly Xaa Gly Trp Ile Ala Xaa Ile Xaa Asp Asp Ala Pro Asn
1               5                   10                  15

Ala Val Phe Val Ala Ala
            20

<210> SEQ ID NO 48
<211> LENGTH: 29
<212> TYPE: PRT
<213> ORGANISM: Artificial Sequence
<220> FEATURE:
<223> OTHER INFORMATION: Lacticin 3147 - A2
<220> FEATURE:
<221> NAME/KEY: MISC_FEATURE
<222> LOCATION: (1)..(1)
<223> OTHER INFORMATION: Xaa = 2-oxobutanoic acid (2-ob)
<220> FEATURE:
<221> NAME/KEY: MISC_FEATURE
<222> LOCATION: (2)..(2)
<223> OTHER INFORMATION: Xaa = dehydroaminobutyric acid (Dhb)
<220> FEATURE:
<221> NAME/KEY: MISC_FEATURE
<222> LOCATION: (5)..(5)
<223> OTHER INFORMATION: Xaa = dehydroaminobutyric acid (Dhb)
<220> FEATURE:
<221> NAME/KEY: MISC_FEATURE
<222> LOCATION: (9)..(9)
<223> OTHER INFORMATION: Ala is in the D confirmation
<220> FEATURE:
<221> NAME/KEY: MISC_FEATURE
<222> LOCATION: (12)..(12)
<223> OTHER INFORMATION: Ala is in the D confirmation
<220> FEATURE:
<221> NAME/KEY: MISC_FEATURE
<222> LOCATION: (22)..(22)
<223> OTHER INFORMATION: Xaa = aminobutyric acid (Abu)
<220> FEATURE:
<221> NAME/KEY: MISC_FEATURE
<222> LOCATION: (26)..(26)
<223> OTHER INFORMATION: Xaa = aminobutyric acid (Abu)

<400> SEQUENCE: 48

Xaa Xaa Pro Ala Xaa Pro Ala Ile Ala Ile Leu Ala Ala Tyr Ile Ala
1               5                   10                  15

Thr Asn Thr Ala Pro Xaa Thr Lys Ala Xaa Arg Ala Ala
            20                  25

<210> SEQ ID NO 49
<211> LENGTH: 20
<212> TYPE: PRT
<213> ORGANISM: Artificial Sequence
<220> FEATURE:
<223> OTHER INFORMATION: Actagardine
<220> FEATURE:
<221> NAME/KEY: MISC_FEATURE
<222> LOCATION: (8)..(8)
<223> OTHER INFORMATION: Xaa = aminobutyric acid (Abu)
<220> FEATURE:
<221> NAME/KEY: MISC_FEATURE
```

```
<222> LOCATION: (10)..(10)
<223> OTHER INFORMATION: Xaa = aminobutyric acid (Abu)
<220> FEATURE:
<221> NAME/KEY: MISC_FEATURE
<222> LOCATION: (15)..(15)
<223> OTHER INFORMATION: Xaa = aminobutyric acid (Abu)

<400> SEQUENCE: 49

Ala Ala Ser Gly Trp Val Ala Xaa Leu Xaa Ile Glu Ala Gly Xaa Val
1               5                   10                  15

Ile Ala Ala Ala
            20

<210> SEQ ID NO 50
<211> LENGTH: 24
<212> TYPE: PRT
<213> ORGANISM: Artificial Sequence
<220> FEATURE:
<223> OTHER INFORMATION: Ruminococcin A
<220> FEATURE:
<221> NAME/KEY: MISC_FEATURE
<222> LOCATION: (7)..(7)
<223> OTHER INFORMATION: Xaa = dehydroaminobutyric acid (Dhb)
<220> FEATURE:
<221> NAME/KEY: MISC_FEATURE
<222> LOCATION: (16)..(16)
<223> OTHER INFORMATION: Xaa = dehydroaminobutyric acid (Dhb)
<220> FEATURE:
<221> NAME/KEY: MISC_FEATURE
<222> LOCATION: (22)..(22)
<223> OTHER INFORMATION: Xaa = aminobutyric acid (Abu)

<400> SEQUENCE: 50

Gly Asn Gly Val Leu Lys Xaa Ile Ala His Glu Cys Asn Met Asn Xaa
1               5                   10                  15

Trp Gln Phe Leu Phe Xaa Ala Ala
            20
```